United States Patent [19]

Funk et al.

[11] Patent Number: 4,496,907

[45] Date of Patent: Jan. 29, 1985

[54] METHOD AND APPARATUS FOR NON-DESTRUCTIVELY DETERMINING INGREDIENTS OF A SAMPLE

[75] Inventors: David B. Funk, Auburn; James D. Kallmeyer, Glenarm, both of Ill.; Wesley H. Harker, Scottsdale, Ariz.

[73] Assignee: Dickey-John Corporation, Auburn, Ill.

[21] Appl. No.: 375,552

[22] Filed: May 6, 1982

[51] Int. Cl.³ .......... G01N 27/02

[52] U.S. Cl. .......... 324/445; 324/226; 324/228; 324/442

[58] Field of Search .......... 324/226, 228, 234, 236, 324/442, 445

[56] References Cited

U.S. PATENT DOCUMENTS

| | | | |
|---|---|---|---|
| 1,793,970 | 2/1931 | Simon et al. | 324/236 |
| 2,948,847 | 8/1960 | Bravenec et al. | 324/445 |
| 3,735,247 | 5/1973 | Harker | 324/226 |

FOREIGN PATENT DOCUMENTS

| | | |
|---|---|---|
| 1135332 | 12/1968 | United Kingdom . |
| 1197852 | 7/1970 | United Kingdom . |
| 1286150 | 8/1972 | United Kingdom . |
| 1398735 | 6/1975 | United Kingdom . |
| 1461077 | 1/1977 | United Kingdom . |
| 1480478 | 7/1977 | United Kingdom . |
| 81WO03226 | 11/1981 | PCT Int'l. Appl. . |

*Primary Examiner*—Michael J. Tokar
*Assistant Examiner*—Kevin D. O'Shea
*Attorney, Agent, or Firm*—Trexler, Bushnell & Wolters, Ltd.

[57] ABSTRACT

A test apparatus is provided for measuring the proportion of at least one constituent in a sample of material, which constituent bears a known relationship to the electrical conductivity of the sample. The test apparatus comprises a sensor including both a receptacle for receiving a sample of material and a field producing coil for producing an electromagnetic field within the receptacle. The coil is also designed confining said electromagnetic field to a predetermined, fixed volume within the receptacle and for producing a substantially constant magnitude electromagnetic field throughout this predetermined, fixed volume. A monitoring circuit is coupled with the sensor and is responsive thereto for producing an output signal which bears a predetermined relationship with the real impedance of the sensor and therefore with the conductivity of the sample.

40 Claims, 13 Drawing Figures

Vcc
+10V UNREG
MODULATOR 170
OSC
488Hz
REFR
Z cos φ
+V
-V

METHOD AND APPARATUS FOR NON-DESTRUCTIVELY DETERMINING INGREDIENTS OF A SAMPLE

BACKGROUND OF THE INVENTION

The present invention is directed generally to nondestructive analysis of materials and more particularly to an analysis method and apparatus which utilizes electromagnetic radiation to measure one or more constituents of a sample of material, for example, the fat content of a sample of meat.

While the non-destructive test method and apparatus of the invention is useful for determining constituent content of various constituents of many materials, the disclosure will be facilitated by addressing the problem of determining the fat to lean ratio in a meat product.

Many meats and meat products are generally evaluated nutritionally on the basis of the ratio of lean meat to fat in the product. Additionally, the prices at which such products are sold are often based at least in part on this ratio. Hence, an accurate determination of the percentage fat or alternatively, the percentage lean in a given meat product assume some economic importance for both the processor and the retailer.

Heretofore, the only reliable method of accurately determining fat or lean content of a sample has been by destructive testing. That is, a sample of the product must be fully cooked and the rendered fat product assayed to determine its percentage as a constituent of the product. Quite apparently, this destructive method of testing is not suitable for relatively frequent tests of relatively large numbers of samples of meat products. The prior art has developed an alternative, electromagnetic test method and apparatus for non-destructively performing such a measurement. One such apparatus is shown for example in U.S. Pat. No. 3,735,247 to Harker. While the method and apparatus disclosed therein has proven useful in many applications, there remains room for yet further improvement.

For example, some problems have arisen with respect to proper sample preparation to ensure both accuracy and repeatability of the measurements obtained by prior art devices. In this regard, it is important to accurately weigh each sample and accurately position the weighed sample in the prior art measurement apparatus.

Additionally, the fundamental measurement technique involved in the prior art apparatus involves inserting a sample into an electromagnetic coil which is shielded against extraneous influence. However, the shield must be open at least at one end thereof to allow entrance and egress of a sample. Such shielding has proven difficult to achieve. Moreover, for accurate operation, the measurement coil must extend well beyond the ends of the sample and the shield must extend well beyond the ends of the coil. While the latter requirement is easy to achieve, it is sometimes difficult to assure that an operator will properly position a sample within the coil.

The foregoing prior art electromagnetic test apparatus and method is based upon the differing electrical properties of lean and fat animal tissue. In this regard, primarily of interest is the relatively large ratio of conductivity between fat and lean tissues which may vary between 5 and 100. However, a ratio of between 1.1 and 10 has also been found between typical lean and fat dielectric constants. Heretofore, it has been proven difficult to separate the electrical effects upon the measurement coil of the conductivity of a sample on the one hand and the dielectric constant on the other hand. Since the relative magnitudes of these two electrical properties may vary considerably in a given sample, it is important to adequately isolate but one of these properties for measurement purposes. Since the conductivity ratio of fat to lean is typically considerably higher than the dielectric constant ratio, it is preferably to isolate the former for measurement purposes. In the prior art apparatus it has proven difficult to eliminate the effects of dielectric constant and assure measurement of substantially only the conductivity of a sample.

The prior art method and apparatus is also based primarily upon power losses and phase shifts in the sample which are reflected back to the field source in the measurement coil. It will be recognized that the power loss is related to conductivity while the phase shift is related to dielectric constant. In order to accurately measure conductivity, then, relatively small incremental power losses must be accurately measured. To ensure accuracy of the power loss measurement, the prior art apparatus required a considerable power input to the measurement coil and hence relatively bulky and expensive high-power electrical and electronic components.

When utilizing a coil as the primary measurement apparatus, additional problems are encountered with the known variations in magnetic and electric field components produced by a coil over the radius or along the axis of a sample of material placed in the coil. For example, it is known that the transverse magnetic (TM) component of the electromagnetic field is advantageous in that the electric field remains constant with changing radius. However, in the prior art apparatus it has been found that at the frequencies required for measurement (100 kHz to 10 MHz), and with the dimensions of a coil necessary to accommodate an adequate sample, it is difficult or impossible to generate a uniform TM mode. Hence, the above-mentioned prior art apparats utilizes primarily the transverse electric (TE) mode for obtaining measurements. Unfortunately, the TE mode field lines run parallel to the axis of the coil and hence the field varies considerably over the radius of a sample within the coil. Since the fat or lean content can also be fairly assumed to vary within a given sample either axially or radially, the foregoing factors present some difficulty in obtaining accurate and repeatable measurements.

OBJECTS AND SUMMARY OF THE INVENTION

Accordingly, it is a general object of the present invention to provide a method and apparatus for non-destructively determining the fat content of a sample of a meat product which substantially avoids the problems of the prior art.

A more specific object is to provide a method and apparatus for measuring fat content in meat products by providing an electromagnetic field and measuring the conductivity of a sample of a meat product introduced into the electromagnetic field.

A related object is to provide a test apparatus in accordance with the foregoing objects which provides a substantially continuous and uniform electromagnetic field throughout a volume into which a sample is introduced.

Another object is to provide a test apparatus in accordance with the foregoing objects which is responsive substantially only to the real power loss within the electromagnetic field.

Yet another object is to provide a test apparatus in accordance with the foregoing objects wherein the electromagnetic field contains substantially no net axial electric field components.

A related object is to provide a test apparatus in accordance with the foregoing objects which is relatively simple and inexpensive and yet highly reliable in operation.

In accordance with one aspect of the invention, a test apparatus is provided for measuring the proportion of at least one constituent in a sample of material, which constituent bears a known relationship to the electrical conductivity of the sample. The test apparatus comprises a sensor including receptacle means for receiving a sample of material therein and field producing means for producing an electromagnetic field within said receptacle, for substantially confining said electromagnetic field to a predetermined, fixed volume within said receptacle means, and for producing a substantially constant magnitude electromagnetic field throughout said predetermined, fixed volume.

In accordance with another aspect of the invention, the foregoing test apparatus is further provided with monitoring circuit means coupled with said sensor and responsive thereto for producing an output signal which bears a predetermined relationship with the real impedance of said sensor both when empty and when the sample is received therein, said output signal thereby bearing a predetermined relationship with the conductivity of said sample, when present, said monitoring circuit means being further substantially unresponsive to the dielectric constant of either or both of said sensor or said sample.

BRIEF DESCRIPTION OF THE DRAWINGS

The foregoing as well as other objects, features and advantages of the invention will be more readily understood upon reading the following detailed description of the illustrated embodiment together with reference to the drawings, wherein.

DETAILED DESCRIPTION OF THE ILLUSTRATED EMBODIMENT

Figure 1:
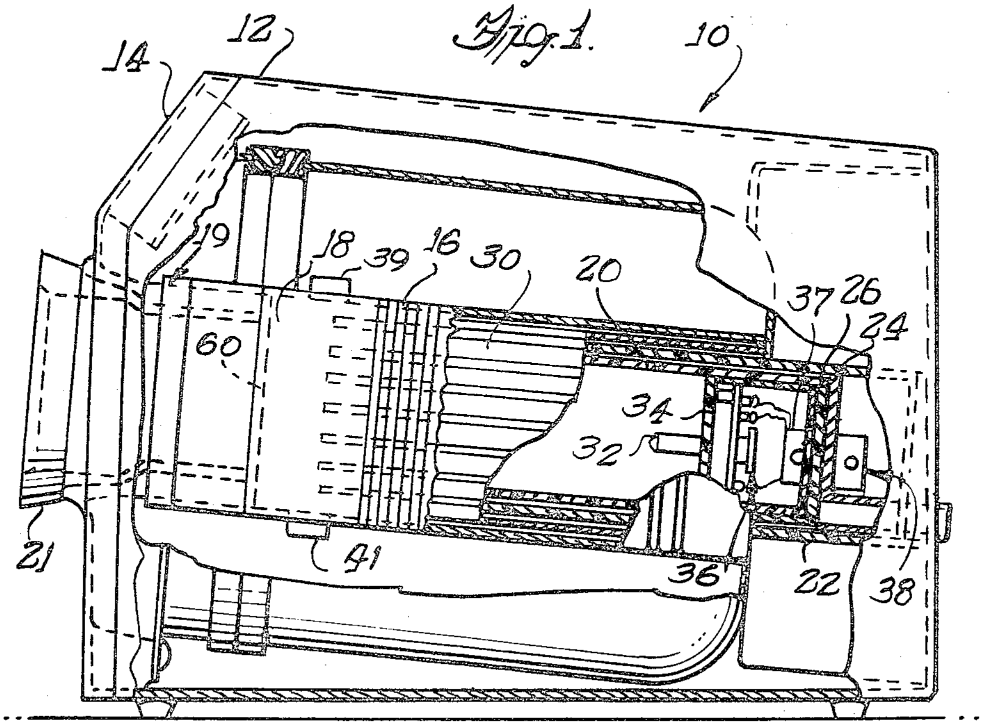
FIG. 1 is a side elevation, partially broken away and partially in section of a test apparatus in accordance with the invention.

Referring to the drawings, and initially to FIG. 1, a preferred form of a test apparatus in accordance with the invention is designated generally by the reference numeral 10. This test apparatus 10 includes a case or housing 12 which conveniently houses all of the components thereof. In this regard, a suitable display of panel 14 may be conveniently mounted on a front side of the casing or housing 12.

In accordance with the principles of the invention, an electromagnetic field is produced in a fixed and preferably cylindrical volume within the housing 12. In the illustrated embodiment, a field producing component or coil 16 is mounted within the housing 12 for this purpose. In the illustrated embodiment, this field producing component or coil 16 is mounted to a cylinder 18, preferably of a transparent non-conductive plastics material, having an open outer end 19 for the ingress and egress of a sample of material to be placed within the electromagnetic field produced thereby for testing purposes. In this regard, a separate, transparent sample container 20 is also preferably of a non-conductive plastics material and a right circular cylinder and preferably is removable with respect to the coil 16. In FIG. 1, the sample container or cylinder 20 is shown fully inserted with respect to the coil 16, whereby it assumes a position substantially concentrically or coaxially aligned within the coil 16. Preferably, a suitable removable cap 21 is also provided for the sample cylinder 20.

In the illustrated embodiment, a sample receiving chamber or receptacle is defined concentrically or coaxially within the coil 16 by a further, fixed transparent and non-conductive plastics material cylinder or tube 22 which slidably receives the sample cylinder 20. In this regard, an end wall 24 is defined within the receptacle 20 and thereby defining a fully inserted or test position thereof within the test apparatus 10. Preferably this end wall 24 is provided with a drain tube or channel 25 to facilitate cleaning of the interior of the fixed cylinder or tube 22.

In order to further control the field produced by the coil 16, as will be more fully described later, a further cylindrical member 30 is concentrically or coaxially mounted therewith. In the illustrated embodiment, this further cylinder 30 is coaxially mounted intermdiate the coil 16 and receptacle 22.

In accordance with a preferred feature of the invention, the sample cylinder 20 also mounts a temperature probe 32 which protrudes upwardly from an enclosure 34 therefor which is placed just above the bottom wall 26. Within this enclosure 34 a plurality of electrical and electronic circuit components, designated generally by the reference numeral 36, are mounted. Briefly, these circuit components 36 accomplish temperature measurment of the sample received in the cylinder 20 in response to the temperature probe 32 and deliver an output signal by way of mating components 37.

Preferably, the enclosure 34 and the walls 24 and 26 are of a transparent and electrically non-conductive material, whereby both light impulses and electromechanical impulses may readily pass therethrough. As will be described more fully later herein, the temperature measurement probe 32 and related circuitry 36 may therefore be isolated within the sample cylinder 20, having no direct mechanical contact between the mating electrical components 37 and cooperating mating compontents, designated generally by the reference numeral 38, within the test apparatus 10. Consequently, the temperature measurement apparatus including the probe 32 and circuitry 34 is carried completely within the sample cylinder 20 for intimate contact with the sample contained therein. However, suitable electrical power for the circuit 34 as well as a signal path for the temperature signals developed thereby are passed to monitoring circuitry carried within the housing 10 by way of the respective mating components 38 and 37.

Additionally, a sensory arrangement comprising a light emitting diode (LED) 39 and a light responsive transistor 41 are mounted on the tube 16 at opposite sides of the tube 22. This sensor arrangement serves to verify proper fitting of the tube 20 with a sample of material, as will be more fully described later.

Figure 2:
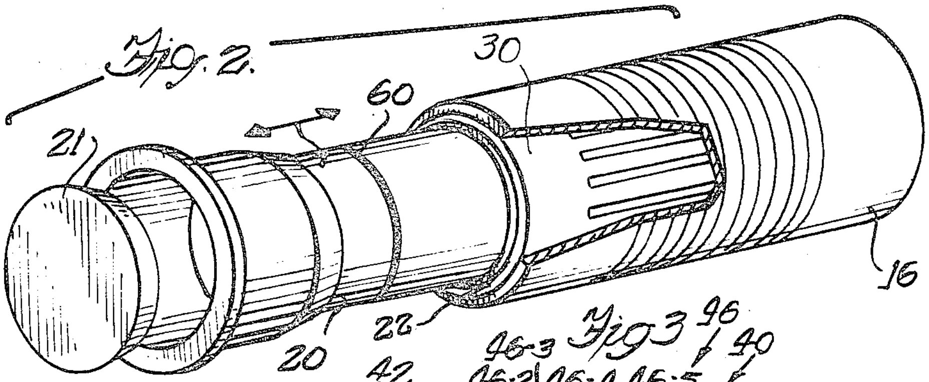
FIG. 2 is a perspective view, partially broken away, of components of the test apparatus of FIG. 1.

With respect to the foregoing description, reference is also invited to FIG. 2, wherein the concentric mounting of the cylinders 18, 22 and 30 and the slidable insertion therein of the cylinder 20 is illustrated.

Figure 3:
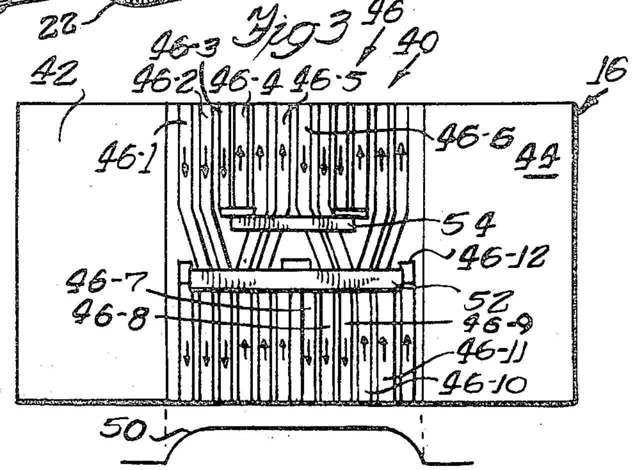
FIG. 3 is a side elevation of a field producing component of the test apparatus of FIG. 1.

As best viewed in FIG. 3, the field producing component or coil 16 comprises an elongate, right cylindrical tube, preferably of a transparent, non-conductive plastics material which carries a plurality of generally circular windings designated generally by the reference numeral 40. In accordance with a feature of the invention, these windings 40 are respectively located and electrically interconnected so as to produce a substantially uniform and continuous electromagnetic field over a predetermined volume within the coil 16. In this regard, the electromagnetic field strength along the axial length of the coil 16 is approximated by the diagram 50 therebelow.

In order to maintain this field 50, a pair of relatively broad end windings or shorting coils 42 and 44 are provided and, as will be seen later, are electrically connected with ground potential to provide well-defined zero field points at either end of the field 50. Intermediate these two end windings 42 and 44 a plurality of intermediate windings or field coils 46 are arranged to produce the substantially uniform and continuous field 50. In the illustrated embodiment these windings 46 each comprise a thin trip of electrically conductive material, preferably copper, wound substantially concentrically about the cylinder 18. These copper strips 46 are substantially evenly spaced along the axial-length of the coil 16 intermediate the end windings 42 and 44, which are preferably considerably broader copper strips also concentrically wound about the cylinder 18. Advantageously, sample measurement is therefore confined to a fixed measurement volume collectively defined by the windings 46 and the field 50 produced thereby.

In the illustrated embodiment, the field windings 46 are twelve in number and are arranged in four groups of three along the axial length of the cylinder 18.

Figure 4:
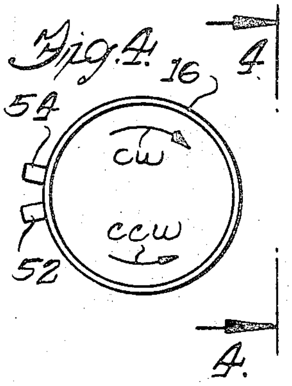
FIG. 4 is an end view of the field producing component of FIG. 3.

Advantageously, these groups of three windings 46 are arranged to direct current flow in alternating clockwise and counterclockwise directions, respectively, about the cylinder 16, these clockwise and counterclockwise directions being indicated in the end view of FIG. 4, to which reference is also invited. In this regard, a first three windings 46-1, 46-2 and 46-3 direct current flow in the clockwise direction, and the winding 46-3 is coupled in series with the next succeeding winding 46-4 so as to reverse the current flow to the counter-clockwise direction. Hence, the succeeding three windings 46-4, 46-5 and 46-6 direct current in a counterclockwise direction, whereupon the windings 46-6 passes current to the next winding 46-7 to be directed in the clockwise direction to and through winding 46-9. Similarly, current flow is again reversed through the remaining three windings 46-10, 46-11 and 46-12. Accordingly, a substantially zero net current flow is accomplished along the axial length of the coil 16.

The axially outermost ends of the respective first and last windings 46-1 and 46-12 are both coupled to circuit ground. Similarly, a midpoint of the windings 46 comprising the axially innermost ends of windings 46-6 and 46-7 is also coupled to circuit ground. In this regard, a suitable grounding strap 52 is provided to tie together these three grounded points of the windings 46.

In accordance with a further feature of the invention, suitable alternating current is fed to the coil 16 at points intermediate the above-described grounded points of the windings 46. In this regard, respective adjacent ends of the windings 46-4 and 46-5 receive an alternating electrical signal and similarly, adjacent ends of windings 46-9 and 46-10 receive the same alternating electrical signal through a common signal strap 54. Hence, it will be seen that net current flow throughout the windings 46 is substantially zero. The foregoing electrical interconnections are also indicated in circuit schematic form in FIG. 7, as will be seen hereinbelow.

In order to render the coil 16 responsive substantially only to the conductivity or real impedance component of the measurement volume defined by the field windings 46, and hence of the portion of a sample of material introduced into this measurement volume, the net axial electric field is also held at a substantially zero value. In addtion to the coil configuration described above, the field control cylinder 22 aids in achieving this reduction of axial electrical field components. In this regard, the cylinder 22 is also preferably of a transparent, non-conductive plastics material and carried a plurality of axially extending field shorting strips radially spaced about its circumference, as indicated generally by the reference numeral 56. In the illustrated embodiment, these shorting strips 56 comprise elongate strips of electrically conductive material such as copper foil, similar to the material utilized to form the field windings 46 of coil 16 as described above. In the illustrated embodiment, these axial strips 56 are sixteen in number and are evenly spaced about the circumference of the cylinder 22. Moreover, the axial length and axial location of each of these strips 56 is such that when the cylinder 22 is coaxially mounted within the coil cylinder 16, each of the axial strips 56 extends at least from one end coil 42 to the other end coil 44, and hence throughout the entire magnetic field produced in the volume surrounded by the field windings 46. In order to ensure shorting out of substantially all electric axial field components these strips 56 preferably extend somewhat into the volume enclosed by the respective end shorting windings 42 and 44.

The foregoing components advantageously produce a well-defined electromagnetic field containing substantially no axial electric field components. Hence, the signal lead or strap 54 will experience a net power consumption which varies substantially only in response to the real power loss or conductivity of the volume defined within the field windings 46. Advantageously, the conductivity of meat products is known to vary considerably with the fat content thereof. Hence, measurement of real power absorption which is directly proportional to electrical conductivity, that is, the real part of impedance, provides a good measure of the fat content of a sample of a meat product. In this regard, a sample of a meat product may readily be placed within the controlled field volume by the simple expedient of providing a suitable filling marking or line about the exterior of the sample cylinder 21, as designated by reference numeral 60 in FIG. 2. Hence, since the bottom wall of the sample cylinder 20 extends somewhat into the area of the end shorting coil 44, and the top marker 60 extends somewhat into the volume within the opposite end shorting coil 42, filling of the sample cylinder 21 from the bottom wall 34 up to at least the marking 60 will assure the placement of a portion of the sample within and completely filling the field 50 in the volume defined by the field coils or windings 46. In this regard, it is preferable to uniformly pack the sample of product into the sample cylinder 21. Sample preparation of this type is most readily carried out with ground meat products. Advantageously, in view of the uniform field provided as described above, having substantially zero axial electric components, the weight of the sample introduced into the sample cylinder 21 has no effect upon the measurement of fat content thereof. Hence, the weight of a sample need not be carefully controlled as with many prior art measuring devices.

Figures 5, 6B, 7A:
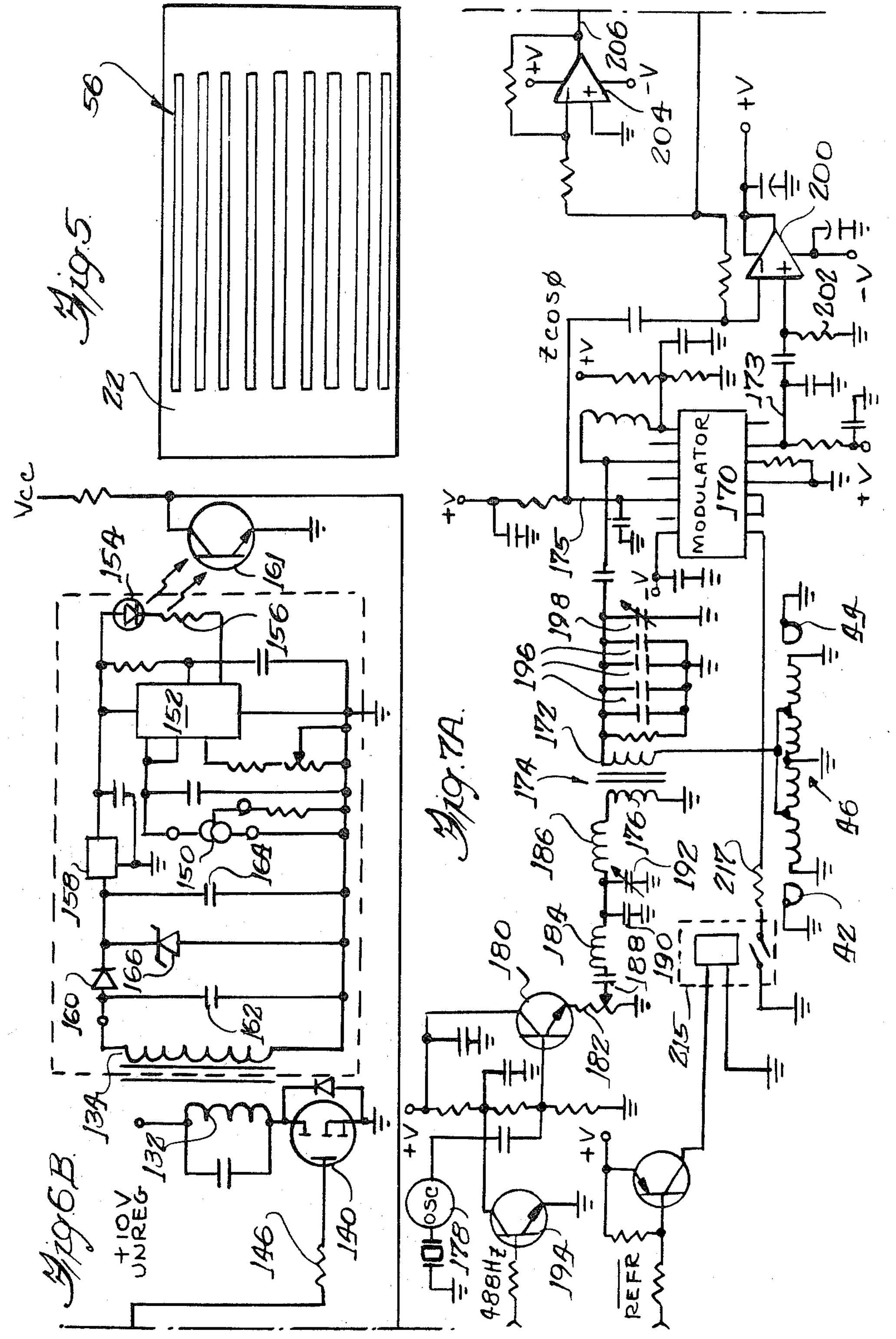
FIG. 5 is a side elevation of a field control component of the apparatus of FIG. 1.
FIGS. 6A and 6B, taken together, form a schematic circuit diagram of one portion of a test circuit useful with the test apparatus of FIG. 1.
FIGS. 7A and 7B, taken together, form a schematic circuit diagram of a further portion of a test circuit useful with the test appartus of FIG. 1.
Figure 6A:
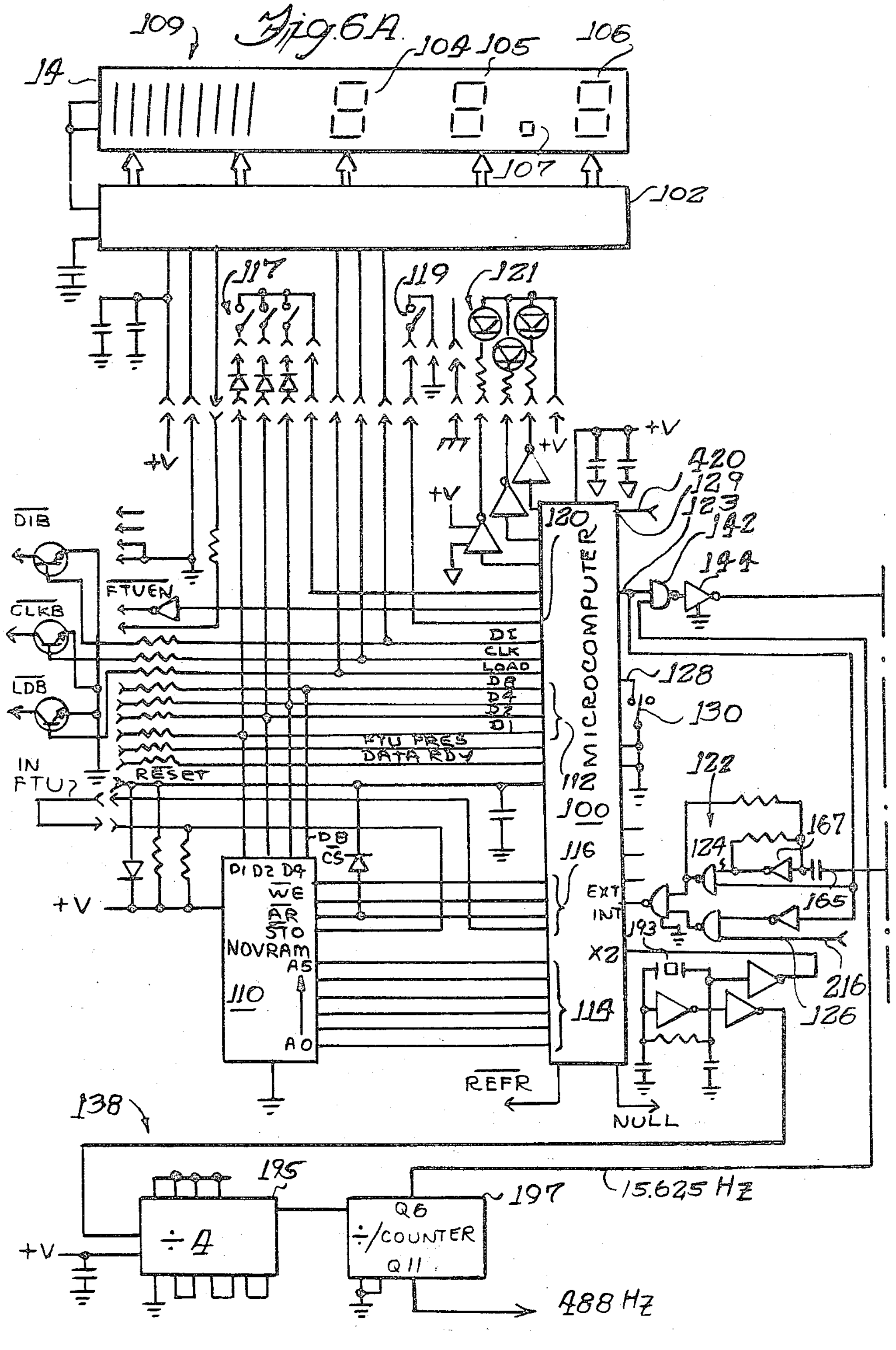

Reference is next invited to FIGS. 6A and 6B wherein a first portion of a novel monitoring circuit for use with the test instrument of FIG. 1 is illustrated in circuit schematic form.

Referring initially to FIG. 6A, in the illustrated embodiment the measurement and display circuitry is microcomputer-based. In this regard, a microcomputer 100 is provided, and is preferably of the type generally designated MK38P70/02 (MOSTEK).

This microcomputer 100 drives the display 14 by way of a suitable display driver integrated circuit 102. In the illustrated embodiment, the display 14 comprises a liquid crystal display panel including three sevensegment alphanumeric characters 104, 105 and 106 and a decimal point 107 for displaying three significant digits to the nearest tenth. Also included are a plurality of selectively energizable message characters 109 for indicating various test functions. The display driver 102 preferably comprises a component of the type generally designated HLCD438.

Additionally three switches 117 and three corresponding LED display elements 121 are provided in the illustrated embodiment for selecting and indicating selection of one of three different products or materials for testing. The microcomputer 100 responds to each switch 117 by selecting appropriate data from a memory 110, as will be shortly described, for the testing of a corresponding product or material.

The microcomputer 100 is programmed to operate upon data received from the measurement coil 16 by way of related circuitry illustrated in FIG. 7, and also to receive temperature data from the probe 32 and related circuits 34, 40 and 38.

A plurality of predetermined empirical constants for calculating percentage fat or lean content of a sample of one or more materials are provided in an electronic memory unit 110. In the illustrated embodiment this memory unit 110 comprises a non-volatile array random access memory (NOVRAM). Preferably this NOVRAM 110 comprises a 64×4-bit memory of the type generally designated XC2210(XICOR). The empirical data is arranged in 64, 4-bit words therein. Hence, 4-bit data transfer but (Cl, D2, D4, D8) is coupled to input ports 112 of the microcomputer 100 and 6-bit address bus $A_0$–$A_5$ is coupled to output ports 114 of the microcomputer 100. A chip select line $\overline{CS}$ and other control inputs $\overline{WE}$, $\overline{AR}$ and $\overline{STO}$ of the NOVRAM 110 are coupled to a suitable output porst 116 of the microcomputer 100. Briefly, in operation, calibration and other empirical data for use in testing a plurality of different products is stored in the NOVRAM 100, where it is accessible for modification in the field, if desired. This NOVRAM 110 normally operates to bidirectionally communicate this data from its RAM portion to the microcomputer 100. However the non-volatile (an $E^2$-PROM) portion of the NOVRAM 110 is also automatically energized to hold the data from the RAM in non-volatile form when power is switched off or otherwise lost to the NOVRAM 110. Upon "power up" the data is then automatically shifted back to the RAM portion. The microcomputer 100 is programmed to accomplish this data shifting by way of its connections to control terminals $\overline{CS}$, $\overline{WE}$, $\overline{AR}$ and $\overline{STO}$ of the NOVRAM 110. Additionally, a field test unit (FTU) to be described later with reference to FIG. 10 may be utilized to verify or change the data in the NOVRAM 110. When this FTU is coupled in circuit with the microcomputer 100, it completes the circuit therefrom to the $\overline{STO}$ input of the NOVRAM. Data may then be shifted to the RAM portion for verification and/or modification, and then shifted back to the PROM portion in similar fashion by the microcomputer 100 upon command from the FTU of FIG. 10. Hence, suitable empirical data for testing any desired product may be placed in the NOVRAM 110.

Input data from one of the temperature probe 32 or the field measurement coil 16 is selected by the microcomputer in response to operator selection by a "temp/data" control switch 119 which feeds an input 120 of the microcomputer 100. In response thereto, the microcomputer issues a control signal on a port 121 thereof. This control signal from the port 121 drives a logic network 122 which receives the temperature data at a first input 124 and the measurement coil data at a second input 126. The output of this logic network 122 feeds an external interrupt (EXT. INT.) port of the microcomputer 100. Hence, the data entering the external interrupt port corresponds to either temperature data or coil measurement data as selected by the switch 119.

Additional control ports of the microprocessor function to select a reference element for calibration purposes ($\overline{REFR}$) and to effect automatic zeroing calibration (NULL). Additionally, a control port 128 of the microcomputer 100 may be left open circuited or tied to ground by manipulation of a switch 130. When the port 128 is left in open circuit condition, the microcomputer 100 functions to calculate and display the percentage fat content of the sample. Conversely, when the switch 130 is closed, grounding the port 128, the microcomputer 100 responds by "inverting∞ the readout to display the lean content of the sample. The remaining ports of the microcomputer 100 interface with the above-mentioned field test unit (FTU) to be described later with reference to FIG. 10.

In accordance with a preferred form of the invention and referring also to FIG. 6B, the temperature measurement circuitry 36 which is carried within the removable enclosure 34 is coupled with the microcomputer 100 by a novel, non-contact arrangement. In this regard, suitable electrical power for energizing the circuitry 36 is provided by an inductive link-up including a coil 132 which is in alignment with a complementary secondary coil 134 forming a part of the circuit 36. The first coil 132 is driven by an oscillating signal provided by a divider circuit 138 and selectively gated by the control terminal 120 at a gate 142. This divider circuit 138 is described later herein.

When a temperature measurement is to be taken, the signal at the port 120 also causes the temperature data from the line 124 to be fed to the EXT. INT. port of the processor, by way of the logic switching circuit 122. A suitable drive transistor 140 (e.g. Vn88AF) is provided for driving the coil 132 with the signals provided at the gate 142. Further in this regard a conventional buffer component 144 and a suitable current limiting resistor 146 are provided in series between the gate 142 and the base electrode of the transistor 140.

The temperature circuit 36 is electrically coupled with a temperature sensing element 150 carried in the temperature probe 32. In the illustrated embodiment, this temperature sensing element 150 comprises a temperature responsive adjustable current source of the type generally designated LM334Z. This temperature responsive element 150 is tied to the input of a voltage-to-frequency converter 152 which in the illustrated embodiment comprises an integrated circuit V-F converter of the type generally designated LM331AN. The output of this voltage-to-frequency converter provides a temperature-dependent variable frequency drive to an LED 154 coupled to a suitable output terminal thereof and provided with a suitable current limiting resistor 156. Suitable passive RC components are coupled with other electrodes of the voltage-to-frequency converter 152 in conventional fashion to result in excitation of the LED 154 at a frequency correlative with the temperature sensed at the temperature sensor element 150.

Suitable DC power is provided to the voltage-to-frequency converter 152 from the secondary coil 134 by way of a conventional integrated circuit voltage regulator component 158, which in the illustrated embodiment comprises a voltage regulator of the type generally designated 7805. A suitable rectifying diode 160 zener reference 166, and smooting capacitors 162, 164 are provided at the input of the voltage regulator 158 from the secondary coil 134. The frequency-temperature analog represented by the periodic flashing of the LED 154 is sensed by a light responsive transistor 161 which forms a part of the circuit 38 mounted at the wall 24 of the cylinder 22 as described above with reference to FIG. 1. This light sensitive transistor 161 is wired as a switching transistor receiving a suitable positive voltage bias through a current limiting resistor 163 at its collector electrode while the emitter electrode thereof is tied to ground. The collector electrode thus comprises the signal output and feeds the temperature related frequency signal back to the input 124 of the logic signal selection circuit 122 by way of a suitable series coupled capacitor 165 buffer component 167.

Figure 8:
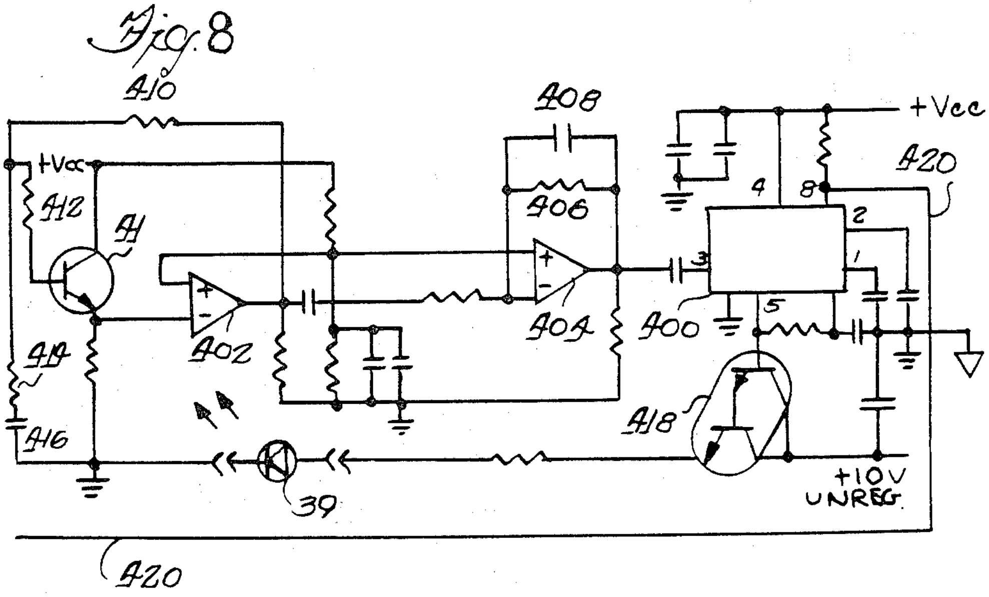
FIG. 8 is a schematic circuit diagram of another portion of a test circuit useful with the test apparatus of FIG. 1.

In accordance with a preferred form of the invention, the microcomputer 100 also receives a signal at a port 129 thereof indicating whether the sample cylinder 20 is properly filled with a sample of material. In this regard, a suitable circuit to be described later with reference to FIG. 8 is utilized to monitor the condition (properly filled or not) of the cylinder 20 and to provide a corresponding signal at the port 129.

referring now to FIG. 7A, a circuit for measuring the real power loss and hence conductivity of a sample placed within the measurement volume defined by the measurement coil 46 is illustrated. The electromagnetic field producing coil 16 and in particular the respective windings 42, 44 and 46 thereof described above with reference to FIG. 3 are here illustrated in circuit schematic form. As mentioned in the above description thereof, the end windings 42 and 44 are tied to circuit ground, as are the axially outermost ends of the windings comprising the measurement coil 46 and the centermost point thereof. The signal points are tied to points in the coil 46 equidistant between the grounded end and the center point and are fed to one input 171 of an integrated circuit modulator component 170.

In the illustrated embodiment the integrated circuit modulator 170 comprises a balanced modulator of the type generally designated MC1496 (MOTOROLA). This same input is also fed a suitable alternating signal from a secondary winding 172 of a transformer 174 whose primary winding 176 receives a suitable high frequency energizing current from a conventional crystal oscillator circuit 178.

In the illustrated embodiment, the oscillator circuit 178 includes an 10 MHz crystal coupled to an oscillator integrated circuit of the type generally designated SL1680C wired with together with suitable capacitors (now shown) wired to produce a signal at a 10 MHz frequency. This 10 MHz signal is fed through a suitable buffer circuit including a transistor 180 wired as an emitter-follower and the amplitude of the resultant signal is adjusted by a suitable potentiometer 182. This 10 MHz signal is fed through a tuned filter circuit comprising a pair of fixed inductors 184, 186, a pair of fixed capacitors 188, 190 and an adjustable tuning capacitor 192 for tuning the filter circuit. The signal from the tuned filter circuit feeds the primary coil 176 mentioned above.

The foregoing circuit is driven by a 488 Hz signal which feeds the base electrode of a transistor 194. The collector electrode of this transistor 194 is coupled in circuit with the buffer circuit including the transistor 180 for "chopping" the signal from oscillator 178 at a 488 Hz rate in response to the 488 Hz signal at the base electrode of the transistor 194.

The foregoing 488 Hz signal is derived from the microprocessor 100 of FIG. 6A by the divider network 138 mentioned above. Briefly, the divider network 138 comprises a first divider component 195 and a second divider component 197 wired essentially in series circuit. The first divider component 195 is divide-by-four counter/divider of the type generally designated 74LS74, while the second divider component 197 is a 14-stage binary counter/divider of the type generally designated CD4020. In this regard the 15.625 KHz signal fed to the gate 142 of FIG. 6A is derived from the Q6 output of the divider 197 while the 488 Hz signal is taken from the Q11 output thereof. The divider network 138 receives a suitably buffered input from a 4 MHz crystal 193 which also provides the crystal input to the microcomputer 100 for deriving a suitable internal master oscillator frequency.

The modulator 170 also receives the signal from the transformer secondary 172, but from the end thereof opposite its connection to the signal points of the measurement coil 46. A 90° fixed phase difference is introduced into this latter signal to the modulator 170 by the inclusion of a plurality of in-parallel fixed capacitors 196. The phase difference is further adjusted to substantially exactly 90°, to compensate for any circuit tolerances, by an adjustable capacitor 198 also wired in parallel with the fixed capacitors 196. Remaining terminals of the modulator integrated circuit component 170 are coupled with suitable DC voltage levels and passive components to produce a modulated output signal across outputs 171 and 173 which is proportionate to $Z\cos\theta$ where Z is the real impedance at the sample coil and 46 and $\theta$ is the 90° phase difference set in by the capacitors 196 and 198.

Figure 7B:
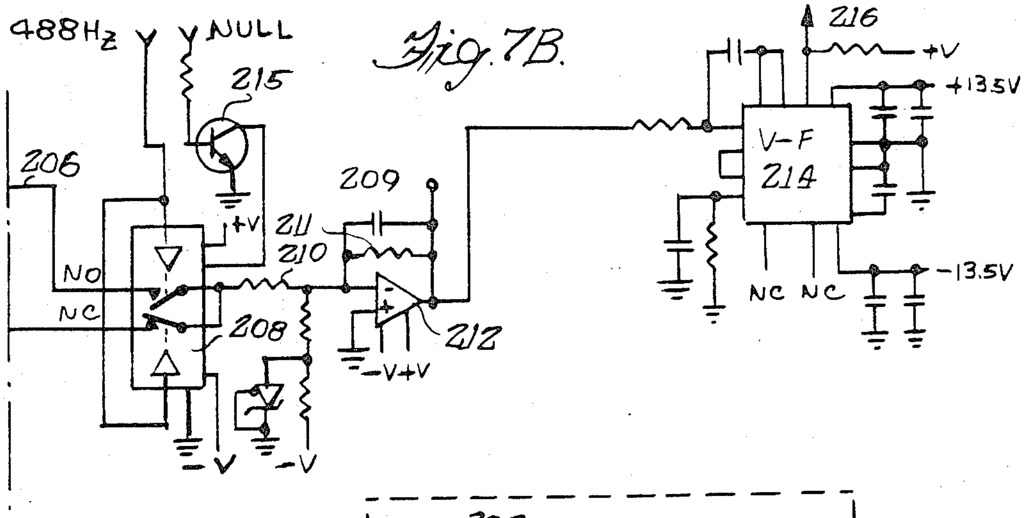

These outputs 171 and 173 are AC coupled to the respective inverting and non-inverting inputs of a differential AC amplifier comprising an operational amplifier 200 which is also provided with an offset reference voltage at its inverting input from a suitable resistor 202. The output of this operational amplifier 200 feeds the inverting input of a further operational amplifier 204 whose non-inverting input is tied to ground and whose output 206 feeds a suitably amplified signal $nZ\cos\theta$, to the like-numbered input 206 of the portion of the circuit shown in FIG. 7B. Referring now to FIG. 7B, input 206 feeds the normally open (NO) terminal of a dual analog switch component 208. In the illustrated embodiment, this analog switch 208 comprises one-half of an analog switch component of the type generally designated LF13333 (National Semi-Conductor). This analog switch 208 also has a normally closed (NC) portion which is fed directly from the output of the operational amplifier 200 of FIG. 7A. The normally closed and normally open portions of the analog switch 208 are driven synchronously by the 488 Hz signal from the divider chain 138 of FIG. 6A mentioned above. This is the same 488 Hz signal feeding the input of the transistor 194 to chop the input signal to the balanced modulator circuit of FIG. 7A. The outputs of the normally closed and normally open contacts of the analog switch 208 are fen in common through a suitable resistor 210 to the inverting input of an operational amplifier 212 which is provided with suitable feedback by way of a capacitor 209 and a resistor 211. The non-inverting input of the op amp 212 is tied to circuit ground. Suitable additional components are illustrated with the operational amplifier 212 whereby this circuit acts as a low pass filter.

Advantageously, the use of the same synchronized 488 Hz signal at the input of the circuit of FIG. 7A and again to drive the analog switch component 208 of FIG. 7B permits this circuit to operate in a synchronous modulated fashion. That is, the switch 208 is driven as a synchronous detector for the signals fed thereto from the circuit of FIG. 7A. Advantageously, the scheme of synchronous modulation and detection substantially eliminates the requirement for precise gain and offset error control and adjustment throughout the circuit of FIG. 7A and 7B. For example, the balanced modulator 170 of FIG. 7A exhibits a significant, though usually stable DC offset voltage. However, it is not possible to predict the DC offset from component to component. This problem is substantially solved, however, by modulating the signal with the 488 Hz "chopper" effect described above and thus coupling only the AC components of the outputs of the modulator 170 to the following circuits. Moreover, by AC coupling the signal and thus eliminating DC components, the output of the balanced modulator tends to closely track the inputs without regard for temperature or voltage supply drift effects, thus greatly improving the signal-to-noise ratio of the downstream signal. Additionally, the use of the lowpass filter circuit including the op-amp 212 permits the circuit to act essentially as a high Q filter substantially rejecting DC errors and noise. In this regard, the operational amplifier 212 and associated circuitry is set for a bandpass of substantially 1 Hz centered on the 488 Hz signal.

In this regard, operation of the synchronous detector comprising the analog switch 208 may be disabled selectively in accordance with the program of microprocessor 100 by way of the NULL output thereof. This NULL output feeds the base electrode of a suitable switching transistor 215 whose emitter electrode is grounded and whose collector electrode feeds the disable terminal of the analog switch component 208. Referring again to FIG. 7A, the reference control output $\overline{REFR}$ from the microcomputer 100 is coupled in circuit with a switching transistor 213 which selectively energizes a switching component 215 to switch the reference resistor 217 into parallel circuit with the coil 46 at its input 171 to the balanced modulator 170. In accordance with the operation of the invention, the microcomputer is programmed to switch this reference resistor into circuit during the measurement cycle both when the sample is absent from the receptacle 22 and again when the filled sample cylinder 20 has been introduced into the sample receptacle 22. This then allows the microcomputer 100 to operate by taking difference readings, that is by noting not only the difference between the "sample present" and "sample absent" signals developed by the circuit of FIG. 7B, but also to note the difference in readings obtained both with a sample present and a sample absent as the reference resistor is switched in and out of the circuit. Since the value of this reference resistor 217 is carefully selected and known and programmed into the microcomputer 100, the sample present and sample absent readings can further be advantageously more accurately determined by calculating them as a difference from the known value of the sample resistor as well as noting their absolute values with the sample resistor not in circuit.

The use of the synchronous modulation and dectection substantially eliminates any necessary gain adjustments in the circuits of FIGS. 7A and 7B. This is true because the chopped output signal essentially represents a chopped input signal, that is to say the measurement signal alternating in a substantially 50% duty cycle with a no signal input. Moreover, since the reference element 217 is switched into circuit both when the sample cell is empty and the sample cell is filled with material, a second difference value is introduced into the modulated signal, that is the difference in signal level with the reference resistor in circuit and out of circuit. Hence, the modulated or chopped output signal of the modulator represents a "difference of differences", that is the difference between no signal and measurement signal present in a substantially 50% duty cycle and the superimposed difference of the reference resistor in and out of circuit, respectively. Hence, the synchronous detector continuously gives a signal which is in effect analagous only to the difference in gains between these levels, whereby any drifts in the absolute values of the gains provided by the various components in the circuits of FIGS. 7A and 7B does not effect the accuracy of the measurement.

Referring again to FIG. 7B, the output of the lowpass filter at the output of the op amp 212 feeds on input of a voltage-to-frequency converter circuit (V-F)214. In the illustrated embodiment, this V-F converter 214 comprises a component of the type generally designated RC4153 (RAYTHEON). The V-F converter 214 is provided with suitable passive components as illustrated to achieve the desired voltage-to-frequency conversion ratio, as is known in the art. The resultant frequency signal is fed out at an output 216 to the like numbered input of the circuit of FIG. 6A. Referring briefly again to FIG. 6A, it wll be seen that this output 216 feeds a remaining input of the selection logic circuit 122 for selection thereof as an input to the microcomputer 100. As described previously, the output of the V-F converter comprises the "data" input selected by manipulation of the switch 119. Reference is next invited to FIG. 8 wherein a sensor circuit associated with the LED and phototransistor 39, 41 described above with reference to FIG. 1 is illustrated. It will be remembered that the LED 39 and photosensitive transistor 41 are positioned at opposite sides of the cylinder 16 to detect the presence of a sample in the sample cylidner 20 to a proper or suitable level to assure accurate measurement. This system acts as an automatic backup on the operator's proper filling of the sample tube with reference to the fill line 60 as also mentioned above.

The LED 39 and photosensitive transistor 41 are again shown in circuit schematic form in FIG. 8. The remainder of the circuit comprises a phase locked loop component (PLL) 400 which receives the output of the photosensitive transistor 41 by way of intervening amplification stages comprising operational amplifiers (op amp) 402 and 404. In the illustrated embodiment, the PLL 400 comprises an integrated circuit component of the type generally designated NE567 (SIGNETICS).

The photosensitive transistor 41 is wired as an emitter follower and feeds its output to the inverting input of the first op amp 402. The output of the op amp 402 is AC coupled to the inverting input of the op amp 404 which is provided with suitable feedback by way of a resistor 406 and a capacitor 408. The output of the second op amp 404 is then AC coupled to the input of the Pll 400. The collector electrode of the transistor 41 together with the non-inverting inputs of the op amps 402 and 404 are biased from a suitable source of DC potential. The output of the op amp 402 also feeds the base electrode of the transistor 41 by way of suitable resistors 410 and 412 and the junction of these two resistors 410, 412 is tied to ground by the series combination of a further resistor 414 and a capacitor 416. The oscillator output of the Pll 400 drives the LED 39 by way of a drive transistor 418 which in the illustrated embodiment comprises a darlington pair component of the type generally designated MPSA18.

From the foregoing it will be seen that the phase lock loop 400 thus locks into its own oscillator frequency which is utilized to drive the LED 39. That is, the photosensitive transistor 41 is energized in response to the frequency of the LED 39 and the output of this phototransistor forms the input to the PLL 400. Hence, the circuit of FIG. 8 forms a very sensitive and stable LED sensor circuit for detecting interruptions in the beam between the LED 39 and the phototransistor 41. In this regard the output of the phase lock loop 400 feeds a line 420 which forms the input to the port 129 of the microcomputer 100 of FIG. 6A.

Figure 9:
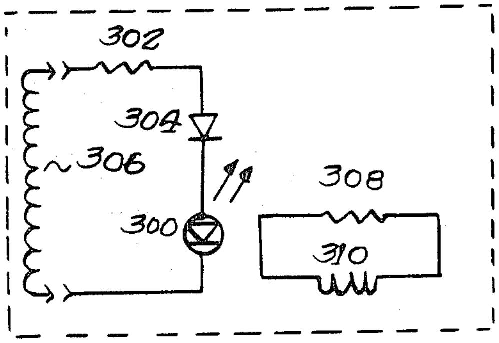
FIG. 9 is a schematic circuit diagram of the circuits of a reference element useful in verifying accurate operation of the test apparatus of the invention.

Referring now to FIG. 9, a reference tube is also provided which is substantially identical in configuration to the sample tube 20 defined above. However, the circuit contents of this reference tube provide reference temperature and data (i.e., sample data) output signals by means of the circuit components contained therein and illustrated in FIG. 9 in circuit schematic form.

The reference temperature output is provided by means of an LED 300 which is coupled in series with a suitable current limiting resistor 302 and a diode 304 across a suitable secondary coil 306. This secondary coil is positioned in the sample tube so as to be in registry with the primary coil 132 described above with reference to FIG. 6B. Hence, this reference temperature circuit provides a predetermined output by way of the light responsive transistor 161 described above with reference to FIG. 6B, with which the LED 300 is positioned in alignment.

The sample data reference circuits comprises the parallel combintaion of a resistance 308 of known value and an inductance 310, which represent the resistance and inductance of a single turn of one-quarter inch copper foil to provide a referencce coil element. This reference element is carried on a reference tube so as to be inserted within the sample volume defined by the coil 16 described above. Hence, the reference tube may be inserted in the same fashion as the sample receiving cylinder or tube 20 to produce a reading to the microprocessor 100 by way of the circuit of FIG. 7A and 7B so as to verify the proper operation of the circuits of the invention.

Figure 10:
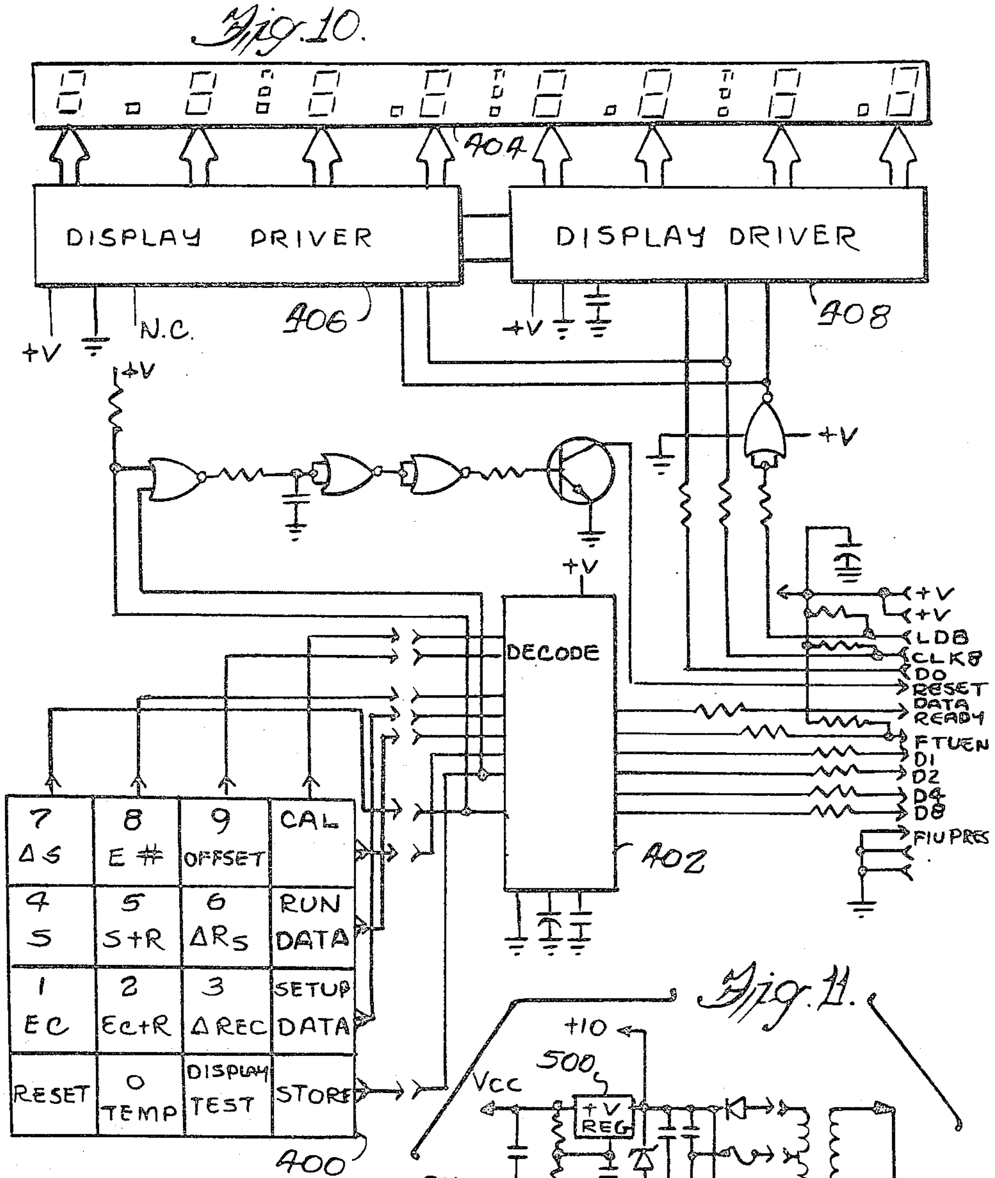
FIG. 10 is a schematic circuit diagram of an auxiliary unit useful in making field modifications in the operation of the apparatus of the invention.

Referring briefly to FIG. 10, the field test unit (FTU) comprises a separate unit which is here illustrated in circit schematic form. Briefly, this field test unit may be coupled with the microprocessor 100 of FIG. 6A by way of the like-designated terminals illustrated in FIG. 10 and in FIG. 6A.

Briefly, the field test unit is operative for selectively reviewing and reprogramming as desired the contents of the NOVRAM 110 of FIG. 6A. It will be remembered that these contents relate primarily to empriical data utilized by the microprocessor 100 in calculating the fat content of each of a plurality of different products or materials.

In this regard, the FTU of FIG. 10 includes a conventional four-by-four keboard 400 which is coupled in an X-Y matrix to a suitable decoder integrated circuit 402. In the illustrated embodiment this decoder circuit 402 comprises an integrated circuit component of the type designated 74C922. Appropriate control and data outputs of the decoder 402 are fed to the like-designated terminals of the microcomputer 100 as indicated in FIG. 10 and FIG. 6A. Additionally, a suitable liquid crystal display element 404 is driven by a pair of suitable liquid crystal display driver components 406 and 408, which in the illustrated embodiment comprise components of the type generally designated HLCD438A. In the illustrated embodiment, the display 404 comprises an eight-digit display with decimal points and colons. The data and other control inputs of the two display driver components 406 and 408 are driven from the like-designated terminals of the microcomputer 100 as indicated in FIG. 10 and FIG. 6A.

Figure 11:
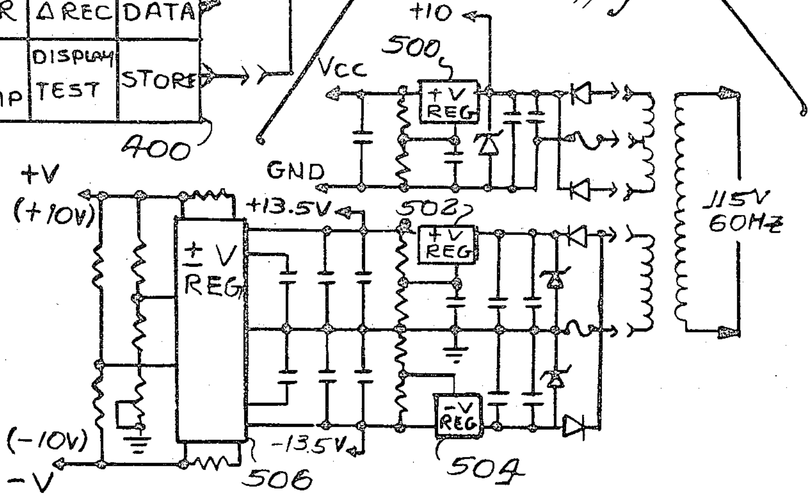
FIG. 11 is a schematic circuit diagram of a power supply circuit for the foregoing circuits.

Referring briefly to FIG. 11 a suitable voltage supply circuit for providing regulated DC voltages at desired levels to the various circuit components thus far described is illustrated. Briefly, the power supply includes variable voltage regulators 500, 502 and 504. In the illustrated embodiment the regulators 500 and 502 are each of the type generally designated 317 and are positive voltage regulators providing respectively +5 and +13.5 volt regulated DC outputs. Regulator 504 is a negative voltage regulator of the type generally designated 337 and provides a −13.5 volt regulated DC output. Additionally, the positive and negative 13.5 volt regulated outputs of the components 502 and 504 are fed to a further voltage regulator component 506. In the illustrated embodiment this latter regulator 506 comprises an integrated circuit component of the type generally designated MC1468L and provides regulated positive and negative 10 volt DC outputs.

In operation, the microcomputer 100 is programmed to control a predetermined sequence of operation to receive the various signals produced by the circuit of FIGS. 7A and 7B. Initially, when the test operation is begun by an operator, the product to be tested is indicated by selection of one of the "product" switches 117 and this selection is indicated by the energization of the corresponding one of the product selection indicator LED's 119. Thereupon, the microcomputer 100 receives the output signal from the circuit of FIGS. 7A and 7B before a sample of material has been introduced into the apparatus. This output signal from the circuit of FIGS. 7A and 7B is received both with the reference resistor 217 switched into the circuit and switched out of the circuit, under the control of the $\overline{\text{REFR}}$ output of the microcomputer 100. Following reception of these signals, the microcomputer 100 causes an appropriate "insert sample" message to be displayed in the characters 109 of the display 14.

Thereupon, the sample cylinder 20 filled with a sample of material to be tested is inserted into the apparatus as described above. The sensor circuit of FIG. 8 verifies that the sample container or cylinder is properly filled to the desired level (at or sufficiently near the line 60 thereon as described above). If the container is not properly filled a suitable error signal is given on the display characters 109 of the display panel 14. When a properly filled sample tube has been inserted in the machine, the temperature reading is initially taken by manipulation of the data temperature switch 119 to the temperature position. Thereafter, the microcomputer 100 again receives the signals provided from the output of the circuit of FIGS. 7A and 7B with the sample present in the apparatus. Once again, these signals are received both with the reference resistor 217 switched into the circuit and switched out of the circuit.

From the foregoing, it will be seen that the microcomputer obtains readings with the sample both present and absent and the reference element or resistor 217 both in circuit and out of circuit. Hence, the microcomputer 100 is programmed to calculate the fat content of the sample based upon all of the readings, by taking appropriate difference values. It will be appreciated that this process substantially eliminates many sources of errors such as gain errors, drift, etc., throughout the circuitry illustrated and described hereinabove.

In order to provide a complete disclosure of a preferred embodiment of the invention, an exemplary program for the microprocessor 100 is produced on the following pages.

```
EMME SMT FILE 1   REV 13 APR 82   JAK/DICKEY JOHN
ERRS LOC OBJECT ADDR LINE              SOURCE STATEMENT

             0001  * EMM1
             0002  *1111111111111111111111111111111111111111111111111111111111111111
             0003  *
             0004  *****************************************************************
             0005  *
             0006  *
             0007  *      EMME SMT       APRIL 7 1981 REV 1.0
             0008  *      5-16-81        J.A. KENNEDY
             0009  *
             0010  *
             0011  *****************************************************************
             0012  *
             0013  * REV 13 OCT 81 JAK
             0014  * ADDED LINEAR EQUATION TO MATH
             0015  * IF KD IS NOT = 0 THEN LINEAR PATH IS USED
             0016  *
             0017  *****************************************************************
             0018  *****************************************************************
             0019  *
             0020  * MAJOR REV 25 JAN 82
             0021  * FOR ALL NEW SMT AND FTU
             0022  *
             0023  *****************************************************************
             0024  *
             0025           TITLE 'EMME SMT  FILE 1  REV 13 APR 82  JAK/DICKEY-JOHN'
             0026  *        A
```

```
EMME SMT  FILE 1  REV 13 APR 82  JAK/DICKEY-JOHN
ERRS  LOC OBJECT ADDR LINE           SOURCE STATEMENT

                      0027  *
                      0028  *
                      0029  *
                      0030  *
                      0031  *
                 0000 0032  ORGIN    RORG  0
                      0033           ENTRY EMPTY,SAMPLE,PREM,WRMUP,WRMDN,DISPT,SAME
                      0034           EXTRN DIRT,EVCLR,CELL,ERROR,MATH,SMISW,TCELL
                      0035           EXTRN BSUB,ERCLR,TD5,TD1S,DIVBIN,MULBIN,KFECH
                      0036           EXTRN BSUB3,NRMLZ,SHRES,SUBEXP,ADDEXP,NRM14
                      0037           EXTRN DCLR,DSP,TD250,TD10MS,TK5
                      0038  *
                      0039  *
                      0040  *
                      0041  *
                      0042  *
                      0043  *  INITIALIZE PORTS
                      0044  *
      0000 1A         0045           DI
      0001 2070       0046           LI    H'70'
      0003 B0         0047           OUTS  0
      0004 2010       0048           LI    H'10'
      0006 B1         0049           OUTS  1
      0007 207F       0050           LI    H'7F'
      0009 B5         0051           OUTS  5
                      0052  *
      000A 280314 0314 0053 P1       PI    DISPT     DISPLAY TEST.
                      0054  *
      000D 2A0000 0000 0055          DCI   0         COMPUTE CHECKSUM ON PROGRAM.
      0010 2010       0056           LI    16
      0012 52         0057           LR    2,A
      0013 20C0       0058           LI    H'C0'
      0015 51         0059           LR    1,A
      0016 70         0060           CLR
      0017 88         0061           AM
      0018 31         0062           DS    1
      0019 94FD   0017 0063          BNZ   *-2
      001B 32         0064           DS    2
      001C 94FA   0017 0065          BNZ   *-5
      001E 2555       0066           CI    H'55'
      0020 8404   0025 0067          BZ    P2        BR IF CKSM PASSED.
      0022 A5         0068           INS   5
      0023 81E6   000A 0069          BP    P1        BR IF EMME SW NOT DEPRESSED.
                      0070  *
                      0071  *  CKSM PASSED, INITIALIZE ALL REGISTERS
                      0072  *
      0025 203F       0073  P2       LI    63
      0027 50         0074           LR    0,A
      0028 40         0075  P3       LR    A,0
      0029 0B         0076           LR    IS,A
      002A 70         0077           CLR
      002B 5C         0078           LR    S,A
      002C 30         0079           DS    0
      002D 94FA   0028 0080          BNZ   P3
                      0081  *
```

```
EMME SMT FILE 1  REV 13 APR 82  JAK/DICKEY-JOHN
ERRS LOC OBJECT ADDR LINE            SOURCE STATEMENT

                      0082  * PERFORM ARRAY RECALL ON ROM/RAM
                      0083  *
     002F 2072        0084         LI    H'72'
     0031 B4          0085         OUTS  4        ARRAY RECALL LO
     0032 2070        0086         LI    H'70'
     0034 B4          0087         OUTS  4        ARRAY RECALL HI.
                      0088  *
                      0089  * INITIALIZE PRODUCT SELECT
                      0090  *
     0035 2010        0091         LI    H'10'
     0037 5A          0092         LR    10,A
     0038 2060        0093         LI    H'60'
     003A B4          0094         OUTS  4        LED ON.
                      0095  *
                      0096  * INITIALIZE EVENT COUNTER.
                      0097  *
     003B 78          0098         LIS   8
     003C B6          0099         OUTS  6
     003D 70          0100         CLR
     003E B7          0101         OUTS  7
                      0102  *
                      0103  *
                      0104  ****************************************************
                      0105  *
                      0106  *             WARM UP
                      0107  *
                      0108  ****************************************************
                      0109  *
                      0110  *
     003F 66          0111  WRMUP  LISU  6
     0040 6C          0112         LISL  4
     0041 70          0113         CLR
     0042 5D          0114         LR    I,A
     0043 5C          0115         LR    S,A      CLR 30 SECOND EC READING.
     0044 47          0116         LR    A,7      SET WAIT AND WARMUP FLAGS.
     0045 2248        0117         OI    H'48'
     0047 57          0118         LR    7,A
     0048 7F          0119         LIS   H'F'
     0049 F8          0120         NS    8
     004A 22C0        0121         OI    H'C0'
     004C 58          0122         LR    8,A      SET EMPTY FLAGS, CLR EMPTY DONE FLAG.
                      0123  *
     004D 2011        0124         LI    H'11'
     004F B1          0125         OUTS  1        SETUP FOR EC DATA.
     0050 280000 0000 0126         PI    TD5      DELAY .5 SECONDS.
     0053 4A          0127  WR4    LR    A,10     SET 30 SECOND FLAG.
     0054 2201        0128         OI    1
     0056 5A          0129         LR    10,A
                      0130  *
     0057 280000 0000 0131  WR3    PI    DIRT     UPDATE DISPLAY.
     005A 64          0132         LISU  4
     005B 68          0133         LISL  0
     005C 280000 0000 0134         PI    CELL     COLLECT EC DATA.
     005F 71          0135         LIS   1
     0060 FA          0136         NS    10
```

```
EMME SMT  FILE 1  REV 13 APR 82  JAK/DICKEY-JOHN
ERRS  LOC OBJECT ADDR LINE          SOURCE STATEMENT

    0061 9408    006A 0137          BNZ   WR1       BR IF 30 SEC FLAG IS SET.
                      0138  *
    0063 65           0139          LISU  5         DECREMENT TIMEOUT COUNTER.
    0064 6A           0140          LISL  2
    0065 3C           0141          DS    S
    0066 94F0    0057 0142          BNZ   WR3       BR IF 30 SECONDS NOT UP.
    0068 90EA    0053 0143          BR    WR4
                      0144  *
    006A 2802F1  02F1 0145  WR1     PI    RANG1     GO CHECK RANGE OF EC DATA.
    006D 70           0146          CLR
    006E C0           0147          AS    0
    006F 8411    0081 0148          BZ    WR2       BR IF DATA IN RANGE.
                      0149  *
    0071 65           0150  WRER1   LISU  5         EC DATA OUT OF RANGE.
    0072 6A           0151          LISL  2         LOAD TIMEOUT COUNTER
    0073 201A         0152          LI    26
    0075 5C           0153          LR    S,A
    0076 66           0154          LISU  6
    0077 6C           0155          LISL  4
    0078 280000  0000 0156          PI    CELL      COLLECT EC DATA FOR 30 SEC COMPARISON.
                      0157  *
    007B 20FE         0158          LI    H'FE'     CLEAR 30 SEC FLAG
    007D FA           0159          NS    10
    007E 5A           0160          LR    10,A
    007F 90D7    0057 0161          BR    WR3
                      0162  *
    0081 2020         0163  WR2     LI    O'40'
    0083 50           0164          LR    0,A
    0084 203D         0165          LI    O'75'
    0086 51           0166          LR    1,A
    0087 66           0167          LISU  6
    0088 6C           0168          LISL  4
                      0169  *
    0089 280000  0000 0170          PI    BSUB      SUBTRACT NEW DATA FROM OLD.
    008C 70           0171          CLR
    008D CF           0172          AS    D
    008E 94E2    0071 0173          BNZ   WRER1     BR IF EXCESSIVE DRIFT (HI BYTE CHK).
    0090 4C           0174          LR    A,S
    0091 250A         0175          CI    10
    0093 92DD    0071 0176          BNC   WRER1     BR IF EXCESSIVE DRIFT (LO BYTE CHK).
                      0177  * CLEAR WARMUP FLAG
    0095 74           0178  WRMDN   LIS   4
    0096 F7           0179          NS    7
    0097 57           0180          LR    7,A
    0098 74           0181          LIS   4
    0099 50           0182          LR    0,A
    009A 280000  0000 0183          PI    ERCLR     CLR RANGE ERROR IF IT WAS SET.
    009D 900C    00AA 0184          BR    EMPTY
                      0185  *
                      0186  *
                      0187  *
                      0188  *
                      0189  ***************************************************
                      0190  *
```

EMME SMT FILE 1 REV 13 APR 82  JAK/DICKEY-JOHN
ERRS LOC OBJECT ADDR LINE          SOURCE STATEMENT

```
                        0191  * CALIBRATION OF EMPTY CELL : DATA,REFR
                        0192  *
                        0193  *****************************************************
                        0194  *
                        0195  *
009F 280000 0000 0196  PREM   PI    DIRT     UPDATE DISPLAY.
00A2 73          0197         LIS   3        DELAY TO ALLOW REMOVAL OF SAMPLE.
00A3 53          0198         LR    3,A      3 SECONDS.
00A4 280000 0000 0199         PI    TDIS
00A7 33          0200         DS    3
00A8 94FB   00A4 0201         BNZ   *-4
                        0202  *
00AA 75          0203  EMPTY  LIS   5
00AB 50          0204         LR    0,A
00AC 280000 0000 0205         PI    ERCLR    CLR ERRORS 5,6,7 IF SET.
00AF 20CF        0206         LI    H'CF'    CLR EMPTY DONE FLAG.
00B1 F8          0207         NS    8
00B2 22C0        0208         OI    H'C0'    SET EC FLAGS.
00B4 58          0209         LR    8,A
00B5 47          0210         LR    A,7
00B6 2240        0211         OI    H'40'
00B8 57          0212         LR    7,A      SET WAIT FLAG
00B9 280000 0000 0213         PI    DIRT     UPDATE DISPLAY.
                        0214  * COLLECT INITIALIZING DATA
00BC 2011        0215         LI    H'11'
00BE B1          0216         OUTS  1        SETUP FOR EC.
00BF 280000 0000 0217         PI    TD5      DELAY .5 SECONDS.
00C2 64          0218         LISU  4
00C3 68          0219         LISL  0
00C4 280000 0000 0220         PI    CELL     COLLECT EC COUNTS.
00C7 280000 0000 0221         PI    DIRT     UPDATE DISPLAY.
00CA 2051        0222         LI    H'51'
00CC B1          0223         OUTS  1        SETUP FOR REFR EC.
00CD 280000 0000 0224         PI    TD5      DELAY .5 SECONDS.
00D0 64          0225         LISU  4
00D1 6A          0226         LISL  2
00D2 280000 0000 0227         PI    CELL     COLLECT REFR COUNTS.
                        0228  *
00D5 64          0229         LISU  4
00D6 6C          0230         LISL  4
00D7 70          0231         CLR            CLEAR SAMPLE DATA:
00D8 5D          0232         LR    I,A         FULL CELL
00D9 8FFE   00D8 0233         BR7   *-1         FULL CELL + REFR
00DB 5E          0234         LR    D,A         TEMPERATURE
00DC 63          0235         LISU  3           EMME#.
00DD 5D          0236         LR    I,A
00DE 5D          0237         LR    I,A
00DF 65          0238         LISU  5
00E0 5D          0239         LR    I,A
00E1 5C          0240         LR    S,A
00E2 6C          0241         LISL  4
00E3 5D          0242         LR    I,A
00E4 5D          0243         LR    I,A
00E5 5D          0244         LR    I,A
00E6 5C          0245         LR    S,A
                        0246  *
```

```
EMME SMT  FILE 1  REV 13 APR 82  JAK/DICKEY-JOHN
ERRS  LOC OBJECT ADDR LINE          SOURCE STATEMENT

      00E7 64            0247  EMP2    LISU  4
      00E8 68            0248          LISL  0
      00E9 4D            0249          LR    A,I      MOVE: R40 -> R64    SAVE EC READING.
      00EA 50            0250          LR    0,A            R41 -> R65.
      00EB 4C            0251          LR    A,S
      00EC 66            0252          LISU  6
      00ED 6D            0253          LISL  5
      00EE 5E            0254          LR    D,A
      00EF 40            0255          LR    A,0
      00F0 5C            0256          LR    S,A
                         0257  *
      00F1 64            0258          LISU  4
      00F2 6A            0259          LISL  2
      00F3 4D            0260          LR    A,I      MOVE: R42 -> R66    SAVE EC REFR.
      00F4 50            0261          LR    0,A            R43 -> R67.
      00F5 4C            0262          LR    A,S
      00F6 66            0263          LISU  6
      00F7 6F            0264          LISL  7
      00F8 5E            0265          LR    D,A
      00F9 40            0266          LR    A,0
      00FA 5C            0267          LR    S,A
      00FB 280000 0000   0268          PI    DIRT     UPDATE DISPLAY.
      00FE 2011          0269          LI    H'11'    SET UP FOR EC DATA.
      0100 B1            0270          OUTS  1
      0101 280000 0000   0271          PI    TD5      DELAY .5 SECONDS.
      0104 64            0272          LISU  4
      0105 68            0273          LISL  0
      0106 280000 0000   0274          PI    CELL     COLLECT EC DATA.
      0109 2802F1 02F1   0275          PI    RANG1    CHECK RANGE OF EC DATA
      010C 70            0276          CLR
      010D C0            0277          AS    0
      010E 8409     0118 0278          BZ    EMP1     BR IF WITHIN RANGE.
                         0279  *
      0110 74            0280          LIS   4
      0111 50            0281          LR    0,A
      0112 280000 0000   0282          PI    ERROR    SET ERROR 4
      0115 29003F 003F   0283          JMP   WRMUP    AND GOTO WARMUP.
                         0284  *
      0118 2034          0285  EMP1    LI    O'64'
      011A 50            0286          LR    0,A
      011B 203D          0287          LI    O'75'
      011D 51            0288          LR    1,A
      011F 64            0289          LISU  4
      011F 68            0290          LISL  0
      0120 28014A 014A   0291          PI    PHAS     COMPARE NEW EC WITH OLD.
                         0292  *                    RETURN IF READINGS WITHIN 10 COUNTS.
                         0293  *
      0123 280000 0000   0294          PI    DIRT     UPDATE DISPLAY.
      0126 2051          0295          LI    H'51'
      0128 B1            0296          OUTS  1        SET UP FOR REFR.
      0129 280000 0000   0297          PI    TD1S     DELAY 1 SECOND.
      012C 280000 0000   0298          PI    DIRT     UPDATE DISPLAY.
      012F 64            0299          LISU  4
      0130 6A            0300          LISL  2
      0131 280000 0000   0301          PI    CELL     COLLECT REFR DATA.
                         0302  *
```

```
EMME SMT  FILE 1  REV 13 APR 82  JAK/DICKEY-JOHN
ERRS  LOC OBJECT ADDR LINE          SOURCE STATEMENT

    0134 2036          0303          LI    0'66'
    0136 50            0304          LR    0,A
    0137 203D          0305          LI    0'75'
    0139 51            0306          LR    1,A
    013A 64            0307          LISU  4
    013B 6A            0308          LISL  2
    013C 28014A 014A  0309           PI    PHAS      COMPARE NEW REFR TO OLD.
                       0310 *                          RETURN IF NEW WITHIN 10 COUNTS OF OLD.
                       0311 *
    013F 48            0312          LR    A,8
    0140 2210          0313          OI    H'10'
    0142 58            0314          LR    8,A       SET EMPTY DONE FLAG
    0143 74            0315          LIS   4
    0144 F7            0316          NS    7         CLR WAIT FLAG.
    0145 2220          0317          OI    H'20'     SET INSERT FLAG.
    0147 57            0318          LR    7,A
    0148 909E    00E7  0319          BR    EMP2
                       0320 *
                       0321 *
                       0322 ***********************************************************
                       0323 *
                       0324 *  CHECK CELL FOR INSERTION OF CLEAR CELL
                       0325 *
                       0326 ***********************************************************
                       0327 *
                       0328 *
    014A 08            0329 PHAS     LR    K,P
    014B 0A            0330          LR    A,IS
    014C 65            0331          LISU  5
    014D 6A            0332          LISL  2
    014E 5C            0333          LR    S,A       SAVE ADDRESS OF NEW DATA.
    014F 0B            0334          LR    IS,A
    0150 280000 0000  0335           PI    BSUB      SUBTRAT NEW - OLD DATA.
    0153 70            0336          CLR
    0154 CE            0337          AS    D
    0155 9407    015D  0338          BNZ   PH1       BR IF OBJECT IN CELL.
    0157 4C            0339          LR    A,S
    0158 250A          0340          CI    10
    015A 9202    015D  0341          BNC   PH1       BR IF OBJECT IN CELL.
    015C 0C            0342          PK              ELSE RETURN.
                       0343 *
    015D 2010          0344 PH1      LI    H'10'
    015F F8            0345          NS    8
    0160 9404    0165  0346          BNZ   PH2       BR IF EMPTY IS DONE.
    0162 2900AA 00AA  0347           JMP   EMPTY     ELSE REPEAT EMPTY SEQUENCE.
                       0348 *
    0165 40            0349 PH2      LR    A,0       RESTORE OLD DATA FOR CALCULATIONS.
    0166 0B            0350          LR    IS,A
    0167 4D            0351          LR    A,I
    0168 50            0352          LR    0,A
    0169 4C            0353          LR    A,S
    016A 51            0354          LR    1,A
    016B 65            0355          LISU  5
    016C 6A            0356          LISL  2
    016D 4C            0357          LR    A,S
    016E 0B            0358          LR    IS,A
```

```
EMME SMT  FILE 1  REV 13 APR 82  JAK/DICKEY-JOHN
ERRS  LOC OBJECT ADDR LINE            SOURCE STATEMENT

     016F 40            0359           LR    A,0
     0170 50            0360           LR    I,A
     0171 41            0361           LR    A,1
     0172 5C            0362           LR    S,A
                        0363  *
                        0364  *
                        0365  *************************************************************
                        0366  *
                        0367  * SAMPLE DATA COLLECTION
                        0368  *
                        0369  *************************************************************
                        0370  *
                        0371  *
     0173 280000 0000   0372  SAMPLE   PI    DIRT
     0176 73            0373           LIS   3
     0177 53            0374           LR    3,A
     0178 280000 0000   0375           PI    TD1S
     017B 33            0376           DS    3
     017C 94FB     0178 0377           BNZ   *-4
                        0378  *
     017E 77            0379           LIS   7          SET WAIT FLAG.
     017F F7            0380           NS    7
     0180 2240          0381           OI    H'40'
     0182 57            0382           LR    7,A
     0183 203F          0383           LI    H'3F'      SET FULL CELL FLAGS.
     0185 F8            0384           NS    8
     0186 58            0385           LR    8,A
     0187 280000 0000   0386           PI    DIRT       UPDATE DISPLAY.
                        0387  *
     018A 67            0388           LISU  7
     018B 68            0389           LISL  0
     018C 280000 0000   0390           PI    TCELL      FIRST TEMPERATURE         TIME = 0.
     018F 280000 0000   0391           PI    TK5
                        0392  *
     0192 2011          0393           LI    H'11'                                TIME = 1.
     0194 B1            0394           OUTS  1          SETUP FOR SAMPLE DATA.
     0195 280000 0000   0395           PI    DIRT
     0198 280000 0000   0396           PI    TD1S
     019B 64            0397           LISU  4                                    TIME = 2.
     019C 6C            0398           LISL  4
     019D 280000 0000   0399           PI    CELL       COLLECT SAMPLE DATA.
                        0400  *
     01A0 2051          0401           LI    H'51'                                TIME = 3.
     01A2 B1            0402           OUTS  1          SETUP FOR FC REFR.
     01A3 280000 0000   0403           PI    TD1S
     01A6 64            0404           LISU  4                                    TIME = 4.
     01A7 6E            0405           LISL  6
     01A8 280000 0000   0406           PI    CELL       COLLECT FC REFR DATA.
                        0407  *
     01AB 280000 0000   0408           PI    DIRT                                 TIME = 5.
     01AE 280000 0000   0409           PI    TD1S
                        0410  *
                        0411  *  REFR DRIFT CHECK
                        0412  *
     01B1 2022          0413           LI    0'42'
     01B3 50            0414           LR    0,A
```

```
FMME SMT  FILE 1  REV 13 APR 82  JAK/DICKEY JOHN
ERRS  LOC OBJECT ADDR LINE          SOURCE STATEMENT

      01B4 2038          0415          LI    0'70'
      01B6 51            0416          LR    1,A
      01B7 64            0417          LISU  4
      01B8 68            0418          LISL  0
                         0419  *
      01B9 280000 0000 0420            PI    BSUB      DELTR EC = DE - RE.
                         0421  *
      01BC 2026          0422          LI    0'46'
      01BE 50            0423          LR    0,A
      01BF 203A          0424          LI    0'72'
      01C1 51            0425          LR    1,A
      01C2 64            0426          LISU  4
      01C3 6C            0427          LISL  4
                         0428  *
      01C4 280000 0000 0429            PI    BSUB      DELTR FC = D - R.
                         0430  *
      01C7 2038          0431          LI    0'70'
      01C9 50            0432          LR    0,A
      01CA 203D          0433          LI    0'75'
      01CC 51            0434          LR    1,A
      01CD 67            0435          LISU  7
      01CE 6A            0436          LISL  2
                         0437  *
      01CF 280000 0000 0438            PI    BSUB      DRIFT = DELTR EC - DELTR FC.
                         0439  *
      01D2 76            0440          LIS   6
      01D3 50            0441          LR    0,A
      01D4 70            0442          CLR
      01D5 CE            0443          AS    D
      01D6 9406    01DD 0444           BNZ   SAME      BR IF DELTR DRIFT EXCESS.
      01D8 4C            0445          LR    A,S
      01D9 250A          0446          CI    10
      01DB 820E    01EA 0447           BC    SAMF
                         0448  *
      01DD 280000 0000 0449  SAME      PI    ERROR     LOAD ERROR 6 OR 7.
      01E0 280000 0000 0450  SAMG      PI    DIRT      UPDATE DISPLAY.
      01E3 60            0451          LISU  0
      01E4 68            0452          LISL  0
      01E5 280000 0000 0453            PI    CELL      CHECK CELL STATUS.
      01E8 90F7    01E0 0454           BR    SAMG      LOOP TIL CELL STATUS CHANGES.
                         0455  *
      01EA 280000 0000 0456  SAMF      PI    DIRT      UPDATE DISPLAY.
      01ED 60            0457          LISU  0
      01EE 68            0458          LISL  0
      01EF 280000 0000 0459            PI    CELL      CHECK CELL STATUS.
      01F2 280000 0000 0460            PI    TD1S      DELAY 1 SECOND.
      01F5 280000 0000 0461            PI    TD1S      DELAY 1 SECOND.
      01F8 280000 0000 0462            PI    DIRT      UPDATE DISPLAY.
      01FB 280000 0000 0463            PI    TD5       DELAY .5 SECONDS.
                         0464  *
      01FE 67            0465          LISU  7
      01FF 68            0466          LISL  0
      0200 280000 0000 0467            PI    TCELL     SECOND TEMPERATURE.
      0203 280000 0000 0468            PI    TK5       ADJUST TEMP 2 BY K5.
                         0469  *
```

```
EMME SMI  FILE 1  REV 13 APR 82  JAK/DICKEY-JOHN
ERRS  LOC OBJECT ADDR LINE         SOURCE STATEMENT

   0206 65           0470         LISU  5                                  TIME = 8.
   0207 6A           0471         LISL  2
   0208 77           0472         LIS   7        LOAD DELAY COUNTER.
   0209 5C           0473         LR    S,A
   020A 280000 0000 0474  SAMA    PI    DIRT     UPDATE DISPLAY.
   020D 60           0475         LISU  0
   020E 68           0476         LISL  0
   020F 280000 0000 0477          PI    CELL     CHECK CELL STATUS.
   0212 280000 0000 0478          PI    TD1S     DELAY 1 SECOND.
   0215 65           0479         LISU  5
   0216 6A           0480         LISL  2
   0217 3C           0481         DS    S
   0218 94F1    020A 0482         BNZ   SAMA     LOOP TIL 10 SECONDS UP.
                     0483  *
   021A 280000 0000 0484          PI    DIRT     UPDATE DISPLAY.
                     0485  *
   021D 67           0486         LISU  7
   021E 68           0487         LISL  0
   021F 280000 0000 0488          PI    TCELL    THIRD TEMPERATURE         TIME = 14.
   0222 280000 0000 0489          PI    TK5      ADJUST TEMP 3 BY K5.
                     0490  *
   0225 66           0491         LISU  6
   0226 68           0492         LISL  0
   0227 20F6         0493         LI    -10      INIT EXPONENT    -13,DIV.
   0229 5C           0494         LR    S,A                       +3,DPADJ.
                     0495  *
   022A 201E         0496         LI    0'36'
   022C 50           0497         LR    0,A
   022D 203A         0498         LI    0'72'
   022F 51           0499         LR    1,A
   0230 65           0500         LISU  5
   0231 6C           0501         LISL  4
   0232 280000 0000 0502          PI    BSUB     T2 - T1.
   0235 280000 0000 0503          PI    NRM14
   0238 280000 0000 0504          PI    ADDEXP
                     0505  *
   023B 201E         0506         LI    0'36'
   023D 50           0507         LR    0,A
   023E 2038         0508         LI    0'70'
   0240 51           0509         LR    1,A
   0241 65           0510         LISU  5
   0242 6E           0511         LISL  6
   0243 280000 0000 0512          PI    BSUB     T3 - T1.
   0246 280000 0000 0513          PI    NRM14
   0249 280000 0000 0514          PI    SUBEXP
                     0515  *
   024C 280000 0000 0516          PI    DIVBIN   T3-T1
   024F 280000 0000 0517          PI    SHRES
                     0518  *
   0252 2A02E2 02E2 0519          DCI   TTAB-8
   0255 67           0520         LISU  7
   0256 68           0521         LISL  0
   0257 4C           0522         LR    A,S
   0258 2509         0523         CI    9
   025A 9204    025F 0524         BNC   SAMH
   025C 78           0525         LIS   8
```

```
EMME SMT  FILE 1  REV 13 APR 82  JAK/DICKEY-JOHN
ERRS  LOC OBJECT ADDR LINE          SOURCE STATEMENT
  .
     025D 9006   0264 0526           BR    SAMI
     025F 250D        0527  SAMH     CI    13
     0261 8202   0264 0528           BC    SAMI
     0263 7E          0529           LIS   14
     0264 8E          0530  SAMI     ADC               POINT TO 8-BIT MULTIPLIER.
     0265 66          0531           LISU  6
     0266 68          0532           LISL  0
     0267 200A        0533           LI    10          INITIALIZE EXPONENT    +16,MULT.
     0269 5C          0534           LR    S,A                                -6,DPADJ.
     026A 67          0535           LISU  7
     026B 69          0536           LISL  1
     026C 70          0537           CLR
     026D 5E          0538           LR    D,A
     026E 16          0539           LM
     026F 5D          0540           LR    I,A
     0270 280000 0000 0541           PI    NRMLZ
     0273 280000 0000 0542           PI    SUBEXP
                      0543  *
     0276 201E        0544           LI    0'36'
     0278 50          0545           LR    0,A
     0279 203A        0546           LI    0'72'
     027B 51          0547           LR    1,A
     027C 65          0548           LISU  5
     027D 6E          0549           LISL  6
     027E 280000 0000 0550           PI    BSUB        T3 - T1.
     0281 280000 0000 0551           PI    NRMLZ
     0284 280000 0000 0552           PI    SUBEXP
                      0553  *
     0287 280000 0000 0554           PI    MULBIN      T3-T1  BY  MULTIPLIER FROM TABLE.
     028A 280000 0000 0555           PI    SHRES
                      0556  *
     028D 67          0557           LISU  7
     028E 68          0558           LISL  0
     028F 0A          0559           LR    A,IS
     0290 50          0560           LR    0,A
     0291 70          0561           CLR
     0292 CA          0562           AS    10
     0293 9104   0298 0563           BM    SAMM        BR IF TEMPERATURE IS DECREASING.
     0295 280000 0000 0564           PI    BSUB3       ELSE NEGATE TEMPERATURE CORRECTION.
                      0565  *
     0298 63          0566  SAMM     LISU  3
     0299 6E          0567           LISL  6
     029A 0A          0568           LR    A,IS
     029B 51          0569           LR    1,A
     029C 280000 0000 0570           PI    BSUB        T1 - (-(T3-T1)*MPIER) = T1 + M (T3-T1).
                      0571  *
     029F 4E          0572           LR    A,D
     02A0 2513        0573           CI    H'13'       TEMPERATURE < 31.0 = ERROR 5.
     02A2 920D   02B0 0574           BNC   SAMJ
     02A4 8406   02AB 0575           BZ    SAMK        BR TO CHECK LOW BYTE.
     02A6 75          0576  SAML     LIS   5
     02A7 50          0577           LR    0,A
     02A8 2901DD 01DD 0578           JMP   SAME
     02AB 4C          0579  SAMK     LR    A,S
     02AC 252A        0580           CI    H'2A'
```

```
EMME SMT  FILE 1  REV 13 APR 82  JAK/DICKEY-JOHN
ERRS  LOC OBJECT ADDR LINE          SOURCE STATEMENT

     02AE 82F7    02A6 0581          BC    SAML      BR IF ERROR.
                       0582  *
     02B0 280000  0000 0583  SAMJ    PI    DIRT      UPDATE DISPLAY.
                       0584  *-------------------------------------------------------------
     02B3 280000  0000 0585          PI    MATH      COMPUTE EMME# AND % LEAN.
                       0586  *-------------------------------------------------------------
     02B6 72           0587          LIS   2
     02B7 FB           0588          NS    11
     02B8 8404    02BD 0589          BZ    SAMD      BR IF NO CKSM FAIL FROM MATH.
     02BA 2901DD  01DD 0590          JMP   SAME      GOTO ERROR LOOP.
                       0591  *
     02BD 48           0592  SAMD    LR    A,8
     02BE 2220         0593          OI    H'20'
     02C0 58           0594          LR    8,A       SET SAMPLE DONE FLAG.
     02C1 70           0595          CLR
     02C2 57           0596          LR    7,A       CLEAR ALTERNATE DISPLAY FLAGS.
                       0597  *
     02C3 65           0598  SAMC    LISU  5
     02C4 6A           0599          LISL  2
     02C5 75           0600          LIS   5
     02C6 5C           0601          LR    S,A       LOAD DELAY COUNTER.
                       0602  *
     02C7 280000  0000 0603  SAMB    PI    SMTSW     ADVANCE SMT DISPLAY IF STEP SW ACTIVE.
     02CA 280000  0000 0604          PI    DIRT      UPDATE DISPLAY.
     02CD 60           0605          LISU  0
     02CE 68           0606          LISL  0
     02CF 280000  0000 0607          PI    CELL      CHECK CELL STATUS.
     02D2 280000  0000 0608          PI    TD5       DELAY .5 SECONDS.
     02D5 65           0609          LISU  5
     02D6 6A           0610          LISL  2
     02D7 3C           0611          DS    S
     02D8 94EE    02C7 0612          BNZ   SAMB      LOOP TIL 5 SECONDS UP.
                       0613  *
     02DA 280000  0000 0614          PI    SMTSW     ADVANCE SMT DISPLAY IF STEP SW ACTIVE.
     02DD 280000  0000 0615          PI    DIRT      UPDATE DISPLAY.
                       0616  *
     02E0 67           0617          LISU  7
     02E1 68           0618          LISL  0
     02E2 280000  0000 0619          PI    TCELL     COLLECT TEMPERATURE.
     02E5 280000  0000 0620          PI    TK5       ADJUST TEMP BY K5.
     02E8 90DA    02C3 0621          BR    SAMC
                       0622  *
                       0623  * TABLE OF MULTIPLIERS:
                       0624  * 1.0 1.1 1.3 1.6 1.9 2.3 2.7  ALL TIMES 2**6
                       0625  *
     02EA 404653       0626  TTAB    DC    H'404653667A93AD'
                       0627  *
                       0628  *
                       0629  *
                       0630  ***************************************************************
                       0631  *
                       0632  *  RANGE CHECK FOR ETA
                       0633  *   R0=0 MEANS DATA OK
                       0634  *
                       0635  ***************************************************************
                       0636  *
                       0637  *
```

```
EMME SMT  FILE 1  REV 13 APR 82  JAK/DICKEY-JOHN
ERRS  LOC OBJECT ADDR LINE          SOURCE STATEMENT

      02F1 08              0638 RANG1   LR    K,P
      02F2 2020            0639         LI    0'40'
      02F4 50              0640         LR    0,A
      02F5 67              0641         LISU  7
      02F6 6D              0642         LISL  5
      02F7 2050            0643         LI    H'50'     LOAD 1.8000.
      02F9 5D              0644         LR    I,A
      02FA 2046            0645         LI    H'46'
      02FC 5E              0646         LR    D,A
      02FD 0A              0647         LR    A,IS
      02FE 51              0648         LR    1,A
      02FF 280000 0000 0649             PI    BSUB      SUBTRACT 1.8000 - EC DATA.
      0302 4E              0650         LR    A,D
      0303 2513            0651         CI    H'13'     CHECK FOR DIFFERENCE >.5000.
      0305 920B   0311 0652             BNC   RA1       BR IF DATA OUT OF RANGE.
      0307 8404   030C 0653             BZ    RA2       BR IF NEED TO CHECK LOW BYTE.
      0309 70              0654 RA3     CLR             HERE IF PASSED CHECK.
      030A 50              0655         LR    0,A
      030B 0C              0656         PK
                           0657 *
      030C 4C              0658 RA2     LR    A,S       CHECK LOW BYTE.
      030D 2588            0659         CI    H'88'
      030F 82F9   0309 0660             BC    RA3       BR IF DATA OK.
                           0661 *
      0311 71              0662 RA1     LIS   1         HERE IF DATA OUT OF RANGE.
      0312 50              0663         LR    0,A
      0313 0C              0664         PK
                           0665 *
                           0666 *
                           0667 ***********************************************************
                           0668 *
                           0669 *       DISPLAY TEST
                           0670 *
                           0671 ***********************************************************
                           0672 *
                           0673 *
      0314 08              0674 DISPT   LR    K,P
      0315 70              0675         CLR
      0316 B4              0676         OUTS  4         LEDS ON.
      0317 2060            0677 DTST    LI    96        LOAD SEGMENT COUNTER.
      0319 50              0678         LR    0,A
      031A 2010            0679 DTST1   LI    H'10'     ALL DISPLAY SEGMENTS ON.
      031C B0              0680         OUTS  0
      031D 2030            0681         LI    H'30'
      031F B0              0682         OUTS  0
      0320 30              0683         DS    0
      0321 94F8   031A 0684             BNZ   DTST1
      0323 2060            0685         LI    H'60'
      0325 B0              0686         OUTS  0
      0326 2070            0687         LI    H'70'
      0328 B0              0688         OUTS  0
      0329 280000 0000 0689             PI    TD1S      DELAY 1 SECOND.
                           0690 *
      032C 2060            0691         LI    96        DISPLAY BLANKING.
      032E 50              0692         LR    0,A
      032F 2050            0693 DTST2   LI    H'50'
```

```
EMME SMT  FILE 1  REV 13 APR 82  JAK/DICKEY-JOHN
ERRS  LOC OBJECT ADDR LINE          SOURCE STATEMENT

    0331 B0          0694           OUTS  0
    0332 2070        0695           LI    H'70'
    0334 B0          0696           OUTS  0
    0335 30          0697           DS    0
    0336 94F8   032F 0698           BNZ   DTST2
    0338 2060        0699           LI    H'60'
    033A B0          0700           OUTS  0
    033B 2070        0701           LI    H'70'
    033D B0          0702           OUTS  0
    033E B4          0703           OUTS  4         PRODUCT LEDS OFF.
    033F 0C          0704           PK
                     0705  *
                     0706           END
00 ERRS

EMME SMT  FILE 2  REV 7 APR 82  JAK/DICKEY-JOHN
ERRS  LOC OBJECT ADDR LINE          SOURCE STATEMENT

                     0001  * EMM2
                     0002  *22222222222222222222222222222222222222222222222222222222222222222222222
                     0003  *
                     0004           TITLE 'EMME SMT  FILE 2  REV 7 APR 82  JAK/DICKEY-JOHN'
                     0005  *        A
                     0006  *
                     0007  *
                     0008  *
                     0009  *
                0000 0010  ORGIN    RORG  0
                     0011           ENTRY SMTSW,EVCLR,DIRT,FEN,SEN,DSP,INVAL
                     0012           ENTRY DENTBL,RUNDAT,FFCN,FM01,PROD,DCLR
                     0013           ENTRY DIRT1,SCLR
                     0014           EXTRN SETUP,BSUB,BTODS,BTODF,TD5,CAL,DISPT
                     0015           EXTRN MULBIN,NRMLZ,SHRES,EMPTY,WRMDN,KBDFTU
                     0016  *
                     0017  *
                     0018  *
                     0019  *        TABLE : BCD TO 7-SEGMENT FOR FTU.
                     0020  *
    0000 7E12BC      0021  DENTBL   DC    H'7E12BCB6D2E6EE32'
    0008 FEF6        0022           DC    H'FEF6'
                     0023  *
                     0024  *        TABLE : BCD TO 7-SEGMENT FOR SMT A 1ST DIGIT, B 2ND, C 3RD.
                     0025  *
    000A DC0104      0026  DENTBA   DC    H'DC010401EC00AC01'  R31 & R32
    0012 3401B8      0027           DC    H'3401B801F8010C01'
    001A FC01BC      0028           DC    H'FC01BC01'
    001E FCC0BA      0029  DENTBB   DC    H'FCC0BAF2C6767EE0'  R32
    0026 FEF6        0030           DC    H'FEF6'
    0028 FA60D6      0031  DENTBC   DC    H'FA60D6F46CBCBEE0'  R33
    0030 FEFC        0032           DC    H'FEFC'
                     0033  *
                     0034  *        TABLE : TO CONVERT FTU KBD NUMBER TO ASSIGNED FTU
                     0035  *              FUNCTION NUMBER (DECIMAL) WITH
                     0036  *              7-SEGMENT ENCODING FOR FTU.
                     0037  *
```

```
FMME SMT  FILE 2  REV 7 APR 82  JAK/DICKEY-JOHN
ERRS  LOC OBJECT ADDR LINE          SOURCE STATEMENT

      0032 00007E       0038 FFCN    DC    H'00007E0000000000'
      003A 1201BC       0039         DC    H'1201BC02B6030000'
      0042 D204E6       0040         DC    H'D204E605EE060000'
      004A 3207FE       0041         DC    H'3207FE08F6090000'
                        0042 *             DIGIT CODE,DIGIT VALUE
                        0043 *
                        0044 ***************************************************************
                        0045 *
                        0046 *  INPUT SMT MODE SWITCH AND SET MODE
                        0047 *
                        0048 ***************************************************************
                        0049 *
      0052 A5           0050 SMTSW   INS   5
      0053 8107    005B 0051         BP    SM1        BR IF SWITCH NOT DEPRESSED.
      0055 73           0052         LIS   3
      0056 F7           0053         NS    7          INC TO NEXT MODE.
      0057 1F           0054         INC
      0058 2103         0055         NI    3
      005A 57           0056         LR    7,A
      005B 1C           0057 SM1     POP
                        0058 *
                        0059 *
                        0060 ****************************************************************
                        0061 *
                        0062 *  CLEAR EVENT COUNTERS
                        0063 *
                        0064 ***************************************************************
                        0065 *
      005C 66           0066 EVCLR   LISU  6
      005D 9002    0060 0067         BR    DC2
                        0068 *
                        0069 *
                        0070 ****************************************************************
                        0071 *
                        0072 *  CLEAR SMT DISPLAY REGISTERS
                        0073 *
                        0074 ****************************************************************
                        0075 *
                        0076 *
      005F 63           0077 DCLR    LISU  3
      0060 6B           0078 DC2     LISL  3
      0061 70           0079 DC1     CLR
      0062 5E           0080         LR    D,A
      0063 8FFE    0062 0081         BR7   *-1
      0065 68           0082         LISL  0          LEAVE ISAR AT MESSAGE REGISTER.
      0066 1C           0083         POP
                        0084 *
                        0085 *
                        0086 ****************************************************************
                        0087 *
                        0088 *  CLEAR FTU DISPLAY REGISTERS EXCEPT INDICATOR AND SELECTION
                        0089 *
                        0090 ****************************************************************
                        0091 *
                        0092 *
      0067 62           0093 SCLR    LISU  2
```

```
EMME SMT  FILE 2  REV 7 APR 82  JAK/DICKEY-JOHN
ERRS  LOC OBJECT ADDR LINE          SOURCE STATEMENT

      0068 6D           0094             LISL  5
      0069 90F7    0061 0095             BR    DC1
                        0096  *
                        0097  *
                        0098  ***************************************************************
                        0099  *
                        0100  *  DISPLY ROUTING
                        0101  *
                        0102  ***************************************************************
                        0103  *
      006B 08           0104  DIRT       LR    K,P
      006C 00           0105             LR    A,KU
      006D 06           0106             LR    QU,A
      006E 01           0107             LR    A,KL
      006F 07           0108             LR    QL,A
                        0109  *
      0070 280330 0330  0110  DIRT1      PI    PROD      CKECK PRODUCT.
                        0111  *
      0073 28005F 005F  0112             PI    DCLR      CLR SMT DISPLAY REGISTERS.
                        0113  *
      0076 70           0114             CLR
      0077 C7           0115             AS    7
      0078 9175    00EE 0116             BM    DI1     BR IF ERROR.
      007A 13           0117             SL    1
      007B 9106    0082 0118             BM    DI2     BR IF WAIT.
      007D 13           0119             SL    1
      007E 911C    009B 0120             BM    DI3     BR IF INSERT.
      0080 901F    00A0 0121             BR    DI20
                        0122  *
                        0123  *  HERE IF WAIT
                        0124  *
      0082 2010         0125  DI2        LI    H'10'
      0084 5D           0126             LR    I,A       LOAD WAIT MESSAGE.
      0085 78           0127             LIS   8
      0086 F7           0128             NS    7
      0087 940A    0092 0129             BNZ   DI24      BR IF WARMING UP.
      0089 2020         0130             LI    H'20'
      008B 5D           0131             LR    I,A
      008C 72           0132             LIS   2         LOAD DASHES FOR 'WAIT' IF NOT WARMUP.
      008D 5D           0133             LR    I,A
      008E 74           0134             LIS   4
      008F 5D           0135             LR    I,A
      0090 900D    009E 0136             BR    DI8
                        0137  *
      0092 A5           0138  DI24       INS   5
      0093 810A    009E 0139             BP    DI8       BR IF EMME SWITCH NOT DEPRESSED.
      0095 64           0140             LISU  4
      0096 68           0141             LISL  0
      0097 70           0142             CLR
      0098 50           0143             LR    0,A
      0099 9076    0110 0144             BR    DI7       ELSE GO DISPLAY EC DATA.
                        0145  *
                        0146  *
                        0147  *  HERE FOR INSERT
                        0148  *
```

```
EMME SMT  FILE 2  REV 7 APR 82  JAK/DICKEY-JOHN
ERRS  LOC OBJECT ADDR LINE          SOURCE STATEMENT

    009B 69           0149  DI3     LISL  1
    009C 72           0150          LIS   2
    009D 5C           0151          LR    S,A       LOAD INSERT MESSAGE.
                      0152  *
                      0153  *  HERE TO CHECK FTU PRESENCE AND MODE
                      0154  *
    009E 9077    0116 0155  DI8     BR    PFMO
                      0156  *
                      0157  *  HERE IF DATA IS TO BE DISPLAYED ON SMT.
                      0158  *
    00A0 73           0159  DI20    LIS   3
    00A1 F7           0160          NS    7
    00A2 9422    00C5 0161          BNZ   DI5      BR IF NOT %.
    00A4 A1           0162          INS   1
    00A5 2102         0163          NI    2
    00A7 9417    00BF 0164          BNZ   DI12     BR IF % LEAN.
    00A9 72           0165          LIS   2
    00AA 5C           0166          LR    S,A       LOAD % FAT MESSAGE.
    00AB 201C         0167          LI    D'34'
    00AD 50           0168          LR    0,A
    00AE 67           0169          LISU  7
    00AF 6D           0170          LISL  5
    00B0 0A           0171          LR    A,IS
    00B1 51           0172          LR    1,A
    00B2 20E8         0173          LI    H'E8'
    00B4 5D           0174          LR    I,A       LOAD 100.0 -> R75,76.
    00B5 73           0175          LIS   3
    00B6 5E           0176          LR    D,A
    00B7 280000  0000 0177          PI    FSUB      %FAT = 100.0 - %LEAN.
    00BA 6D           0178          LISL  5
    00BB 7A           0179  DI23    LIS   10
    00BC 50           0180          LR    0,A       SELECT BTOD CONVERSION FACTOR FOR %.
    00BD 9052    0110 0181          BR    DI7
                      0182  *
    00BF 71           0183  DI12    LIS   1
    00C0 5C           0184          LR    S,A       LOAD % LEAN MESSAGE.
    00C1 63           0185          LISU  3
    00C2 6C           0186          LISL  4
    00C3 90F7    00BB 0187          BR    DI23
                      0188  *
    00C5 2501         0189  DI5     CI    1
    00C7 940A    00D2 0190          BNZ   DI6       BR IF NOT EMME #.
    00C9 69           0191          LISL  1
    00CA 71           0192          LIS   1
    00CB 5C           0193          LR    S,A       LOAD DATA MESSAGE.
    00CC 65           0194          LISU  5
    00CD 68           0195          LISL  0
    00CE 75           0196          LIS   5         SELECT BTOD CONVERSION FACTOR FOR EMME#.
    00CF 50           0197          LR    0,A
    00D0 903F    0110 0198          BR    DI7
    00D2 2502         0199  DI6     CI    2
    00D4 940D    00E2 0200          BNZ   DI17      BR IF NOT DEGREES C.
    00D6 2080         0201          LI    H'80'
    00D8 5C           0202  DI15    LR    S,A       LOAD DEGREES C MESSAGE.
    00D9 4B           0203          LR    A,11
    00DA 2201         0204          OI    1         SET SMT TEMPERATURE DISP FLAG.
```

```
EMME SMT  FILE 2  REV 7 APR 82  JAK/DICKEY-JOHN
ERRS  LOC OBJECT ADDR LINE          SOURCE STATEMENT

      00DC 5B            0205          LR    11,A
      00DD 2802E3 02E3 0206           PI    DEGC      GOTO CALCULATE DEGREES C.
      00E0 90DA   00BB 0207           BR    DI23
                         0208  *
      00E2 2020          0209  DI17    LI    H'20'
      00E4 5C            0210          LR    S,A       LOAD DEGREES F MESSAGE.
      00E5 4B            0211          LR    A,11
      00E6 2201          0212          OI    1
      00E8 5B            0213          LR    11,A
      00E9 2802C5 02C5 0214           PI    DEGF
      00EC 90CE   00BB 0215           BR    DI23
                         0216  *
                         0217  *  HERE IF ERROR
                         0218  *
      00EE 2010          0219  DI1     LI    H'10'
      00F0 F7            0220          NS    7
      00F1 12            0221          SR    1
      00F2 12            0222          SR    1
      00F3 2240          0223          OI    H'40'     LOAD ERROR MESSAGE FLAG.
      00F5 5C            0224          LR    S,A       ALSO REMOVE IF FLAG SET.
      00F6 65            0225          LISU  5
      00F7 6B            0226          LISL  3
      00F8 4C            0227          LR    A,S
      00F9 53            0228          LR    3,A
      00FA 71            0229          LIS   1         HERE TO DISPLAY ERROR NUMBER.
      00FB 54            0230          LR    4,A
      00FC 71            0231  DI22    LIS   1
      00FD F3            0232          NS    3
      00FE 9409   0108   0233          BNZ   DI19
      0100 43            0234          LR    A,3       LOAD HIGHEST PRIORITY ERROR.
      0101 12            0235          SR    1
      0102 53            0236          LR    3,A
      0103 44            0237          LR    A,4
      0104 1F            0238          INC
      0105 54            0239          LR    4,A
      0106 90F5   00FC   0240          BR    DI22
      0108 44            0241  DI19    LR    A,4
      0109 15            0242          SL    4
      010A 54            0243          LR    4,A
      010B 70            0244          CLR
      010C 52            0245          LR    2,A
      010D 53            0246          LR    3,A
      010E 9004   0113   0247          BR    DI16
                         0248  *  ISAR IS POINTING TO DATA.
      0110 280000 0000 0249  DI7     PI    BTODS     GOTO CONVERT BINARY TO DECIMAL.
      0113 28028B 028B 0250  DI16    PI    SEN       GOTO ENCODE DECIMAL TO 7-SEGMENT.
                         0251  *
                         0252  *  LEADING ZERO BLANKING AND DECIMAL POINT SETTING FOR SMT.
                         0253  *
      0116 73            0254  PFM0    LIS   3
      0117 F7            0255          NS    7
      0118 2501          0256          CI    1
      011A 8431   014C   0257          BZ    DI9       BR IF EMME# MODE.
      011C 63            0258          LISU  3
      011D 69            0259          LISL  1
      011E 20FC          0260          LI    H'FC'
```

```
EMME SMT  FILE 2  REV 7 APR 82  JAK/DICKEY-JOHN
ERRS  LOC OBJECT ADDR LINE         SOURCE STATEMENT

      0120 FE            0261              NS    D
      0121 25DC          0262              CI    H'DC'
      0123 940C     0130 0263              BNZ   DI10       BR IF LEADING DIGIT NOT ZERO.
      0125 78            0264              LIS   8
      0126 FD            0265              NS    I
      0127 9408     0130 0266              BNZ   DI10       BR IF HALF DIGIT = 1.
      0129 73            0267              LIS   3
      012A FC            0268              NS    S
      012B 5D            0269              LR    I,A        ELSE BLANK LEADING ZERO FOR % MODE.
      012C 20FE          0270              LI    H'FE'
      012E FC            0271              NS    S
      012F 5C            0272              LR    S,A
      0130 6B            0273  DI10        LISL  3
      0131 47            0274              LR    A,7
      0132 14            0275              SR    4
      0133 9418     014C 0276              BNZ   DI9        BR IF NOT A DATA DISPLAY MODE.
      0135 4C            0277              LR    A,S
      0136 1F            0278              INC
      0137 5C            0279              LR    S,A        SET DP FOR % OR TEMPERATURE MODES.
      0138 78            0280              LIS   8
      0139 FA            0281              NS    10
      013A 8411     014C 0282              BZ    DI9        BR IF NOT NEGATIVE DEGREES C.
      013C 73            0283              LIS   3
      013D F7            0284              NS    7
      013E 2502          0285              CI    2
      0140 940B     014C 0286              BNZ   DI9        BR IF NOT DEGREES C.
      0142 69            0287              LISL  1
      0143 73            0288              LIS   3
      0144 FC            0289              NS    S
      0145 2220          0290              OI    H'20'      ELSE SET NEGATIVE SIGN.
      0147 5D            0291              LR    I,A
      0148 4C            0292              LR    A,S
      0149 12            0293              SR    1
      014A 13            0294              SL    1
      014B 5C            0295              LR    S,A
                         0296  *
      014C 9041     018E 0297  DI9         BR    FMOD
                         0298  *
      014E 76            0299  DI11        LIS   6          SET DP FOR FTU.
      014F FA            0300              NS    10
      0150 12            0301              SR    1
      0151 2411          0302              AI    O'21'
      0153 0B            0303              LR    IS,A
      0154 4C            0304              LR    A,S
      0155 1F            0305              INC
      0156 5C            0306              LR    S,A
                         0307  *
      0157 28015B 015B   0308  DI25        PI    DSP        OUTPUT DISPLAY.
      015A 0D            0309              LR    P0,Q       RETURN.
                         0310  *
                         0311  *
                         0312  *********************************************************
                         0313  *
                         0314  *  OUTPUT DISPLAY UPDATE  USES R0,1,2
                         0315  *
                         0316  *********************************************************
```

```
EMME SMT  FILE 2  REV 7 APR 82  JAK/DICKEY-JOHN
ERRS  LOC OBJECT ADDR LINE          SOURCE STATEMENT

                       0317  *
      015B 2060        0318  DSP     LI    96
      015D 51          0319          LR    1,A       LOAD SEGMENT COUNTER.
      015E 2010        0320          LI    H'10'
      0160 50          0321          LR    0,A       LOAD PORT DATA TO SET CLK HI, LOAD LO.
      0161 62          0322          LISU  2
      0162 6F          0323          LISL  7         FTU DISPLAY IS FIRST.
      0163 70          0324  DSP1    CLR
      0164 CC          0325          AS    S
      0165 52          0326          LR    2,A
      0166 40          0327  DSP2    LR    A,0
      0167 9103   016B 0328          BM    DSP3      BR IF DATA = ON.
      0169 2240        0329          OI    H'40'
      016B B0          0330  DSP3    OUTS  0         CLK HI, DATA X, LOAD LO.
      016C 2220        0331          OI    H'20'
      016E B0          0332          OUTS  0         CLK LO, DATA X, LOAD LO.
      016F 31          0333          DS    1         DECREMENT SEGMENT COUNTER.
      0170 77          0334          LIS   7
      0171 F1          0335          NS    1         TIME TO CHANGE REGISTERS?
      0172 8406   0179 0336          BZ    DSP4
      0174 42          0337          LR    A,2       NO, JUST SHIFT LEFT.
      0175 13          0338          SL    1
      0176 52          0339          LR    2,A
      0177 90EE   0166 0340          BR    DSP2
      0179 0A          0341  DSP4    LR    A,IS
      017A 24FF        0342          AI    -1        DECREMENT ISAR TO NEXT REGISTER.
      017C 250F        0343          CI    O'17'
      017E 9403   0182 0344          BNZ   DSP5      BR IF NOT FINISHED WITH FTU DISPLAY.
      0180 201B        0345          LI    O'33'     ELSE POINT TO SMT DISPLAY REGISTERS.
      0182 0B          0346  DSP5    LR    IS,A
      0183 70          0347          CLR
      0184 C1          0348          AS    1
      0185 94DD   0163 0349          BNZ   DSP1      BR IF SEGMENT COUNTER NOT ZERO.
      0187 2060        0350          LI    H'60'
      0189 B0          0351          OUTS  0         CLK LO, DATA LO, LOAD HI.
      018A 2070        0352          LI    H'70'
      018C B0          0353          OUTS  0         CLK LO, DATA LO, LOAD LO.
      018D 1C          0354          POP
                       0355  *
                       0356  *
                       0357  ************************************************************
                       0358  *
                       0359  *  FTU FUNCTION DECODED
                       0360  *
                       0361  ************************************************************
                       0362  *
      018E A1          0363  FMOD    INS   1         CHECK FOR PRESENCE OF FTU.
      018F 9104   0194 0364          BM    FM01      BR IF FTU IS PRESENT.
      0191 29014E 014E 0365          JMP   DI11
                       0366  *
      0194 280067 0067 0367  FM01    PI    SCLR      CLR FTU DISPLAY REGISTERS.
      0197 70          0368          CLR
      0198 53          0369          LR    3,A
      0199 54          0370          LR    4,A
      019A 55          0371          LR    5,A
      019B 56          0372          LR    6,A
```

```
EMME SMT  FILE 2  REV 7 APR 82  JAK/DICKEY-JOHN
ERRS  LOC OBJECT ADDR LINE          SOURCE STATEMENT

    019C 280000 0000 0373           PI    KBDFTU    READ FTU KEYBOARD.
                     0374  *
    019F 40          0375           LR    A,0
    01A0 2503        0376           CI    3
    01A2 9404   01A7 0377           BNZ   FM02      BR IF NOT STORE MODE.
    01A4 2902B5 02B5 0378           JMP   INVAL     STORE MODE INVALID HERE.
                     0379  *
    01A7 78          0380  FM02     LIS   8
    01A8 F7          0381           NS    7
    01A9 40          0382           LR    A,0
    01AA 9432   01DD 0383           BNZ   FM07      BR IF WARMING UP.
    01AC 250F        0384           CI    H'F'
    01AE 9404   01B3 0385           BNZ   FM04      BR IF NOT CAL MODE.
    01B0 290000 0000 0386           JMP   CAL
                     0387  *
    01B3 250B        0388  FM04     CI    H'B'
    01B5 9403   01B9 0389           BNZ   FM05      BR IF NOT RUNDAT MODE.
    01B7 9030   01E8 0390           BR    RUNDAT
                     0391  *
    01B9 2507        0392  FM05     CI    7
    01BB 9404   01C0 0393           BNZ   FM06      BR IF NOT SETUP MODE.
    01BD 290000 0000 0394           JMP   SETUP
                     0395  *
    01C0 2502        0396  FM06     CI    2
    01C2 940A   01CD 0397           BNZ   FM03      BR IF NOT DISP MODE.
    01C4 280000 0000 0398           PI    DISPT     TURN ALL DISPLAY ON.
    01C7 A1          0399           INS   1
    01C8 15          0400           SL    4
    01C9 91FD   01C7 0401           BM    *-2       WAIT HERE TIL ANOTHER KEY IS SELECTED.
    01CB 9019   01E5 0402           BR    FM08
                     0403  *
    01CD 2A0032 0032 0404  FM03     DCI   FFCN
    01D0 13          0405           SL    1
    01D1 8E          0406           ADC
    01D2 6E          0407           LISL  6
    01D3 16          0408           LM
    01D4 5C          0409           LR    S,A       LOAD DISPLAY CODE FOR THE CHOSEN FCN #.
    01D5 20F0        0410           LI    H'F0'
    01D7 F8          0411           NS    8
    01D8 8B          0412           OM
    01D9 58          0413           LR    8,A       SAVE DIGIT IN FTU DIGIT 7 REGISTER.
    01DA 290157 0157 0414  FM09     JMP   DL5
                     0415  *                        SMT IS IN WARMUP MODE.
    01DD 2507        0416  FM07     CI    7
    01DF 94FA   01DA 0417           BNZ   FM09      BR IF FTU SETUP MODE IS NOT SELECTED.
    01E1 6E          0418           LISL  6
    01E2 207E        0419           LI    H'7E'     ELSE FORCE FTU TO DISPLAY SETUP MODE 0.
    01E4 5C          0420           LR    S,A
    01E5 290000 0000 0421  FM08     JMP   WRMDN     GOTO END WARMUP MODE.
                     0422  *
                     0423  *  RUN DATA
                     0424  *
    01E8 7F          0425  RUNDAT   LIS   15
    01E9 F8          0426           NS    8
    01EA 50          0427           LR    0,A
    01EB 2509        0428           CI    9
    01ED 9404   01F2 0429           BNZ   RU1
    01EF 2902B5 02B5 0430  RU8      JMP   INVAL     KEY 9,OFFSET NOT VALID RUN DATA MODE.
```

```
GAGE SMT  FILE 2  REV 7 APR 82  JAK/DICKEY-JOHN
ERRS  LOC OBJECT ADDR LINE          SOURCE STATEMENT

                      0431  *
     01F2 62          0432  RU1     LISU  2
     01F3 6F          0433          LISL  7
     01F4 2080        0434          LI    H'80'
     01F6 50          0435          LR    S,A      SET DATA INDICATOR.
     01F7 70          0436          CLR
     01F8 C0          0437          AS    0
     01F9 844F   0249 0438          BZ    RU10     BR IF TEMPERATURE.
     01FB 20F9        0439          LI    H'F9'
     01FD FA          0440          NS    10
     01FE 2206        0441          OI    6
     0200 5A          0442          LR    10,A     SET DP FLAGS TO POSITION 3.
     0201 64          0443          LISU  4
     0202 40          0444          LR    A,0
     0203 2501        0445          CI    1
     0205 9404   020A 0446          BNZ   RU2      BR IF NOT EC DATA.
     0207 68          0447          LISL  0
     0208 9028   0231 0448          BR    RUN1
     020A 2502        0449  RU2     CI    2
     020C 9404   0211 0450          BNZ   RU3      BR IF NOT EC+REFR DATA.
     020E 6A          0451          LISL  2
     020F 9021   0231 0452          BR    RUN1
     0211 2503        0453  RU3     CI    3
     0213 9406   021A 0454          BNZ   RU4      BR IF NOT DELTR EC.
     0215 6A          0455          LISL  2
     0216 2020        0456          LI    O'40'
     0218 903D   0256 0457          BR    DELT
     021A 2504        0458  RU4     CI    4
     021C 9404   0221 0459          BNZ   RU5      BR IF NOT SAMPLE DATA.
     021E 6C          0460          LISL  4
     021F 9011   0231 0461          BR    RUN1
     0221 2505        0462  RU5     CI    5
     0223 9404   0228 0463          BNZ   RU6      BR IF NOT SAMPLE+REFR.
     0225 6E          0464          LISL  6
     0226 900A   0231 0465          BR    RUN1
     0228 2506        0466  RU6     CI    6
     022A 9411   023C 0467          BNZ   RU7      BR IF NOT DELTR SAMPLE.
     022C 6C          0468          LISL  4
     022D 2026        0469          LI    O'46'
     022F 9026   0256 0470          BR    DELT
                      0471  *
     0231 70          0472  RUN1    CLR            SELECT CONVERSION FACTOR FOR BTOD.
     0232 50          0473  RUN2    LR    0,A
     0233 280000 0000 0474          PI    BTODF    GOTO CONVERT BINARY TO DECIMAL.
     0236 280260 0260 0475          PI    FEN      GOTO ENCODE DECIMAL TO 7-SEGMENT.
     0239 29014E 014E 0476          JMP   DI11
                      0477  *
     023C 2507        0478  RU7     CI    7
     023E 68          0479          LISL  0
     023F 9405   0245 0480          BNZ   RU9      BR IF NOT DELTS.
     0241 2024        0481          LI    O'44'
     0243 9012   0256 0482          BR    DELT
     0245 65          0483  RU9     LISU  5        ASSUME KEY 8 SELECTED.
     0246 75          0484          LIS   5
     0247 90EA   0232 0485          BR    RUN2
                      0486  *
     0249 20F9        0487  RU10    LI    H'F9'    HERE IF TEMPERATURE.
     024B FA          0488          NS    10
```

```
FMME SMT FILE 2 REV 7 APR 82 JAK/DICKEY-JOHN
ERRS LOC OBJECT ADDR LINE          SOURCE STATEMENT

     024C 5A            0489          LR   10,A     SET DP FLAGS TO POSITION 1.
     024D 4B            0490          LR   A,11
     024E 12            0491          SR   1
     024F 13            0492          SL   1
     0250 5B            0493          LR   11,A     CLR SMT TEMPERATURE DISP FLAG.
     0251 2802C5 02C5   0494          PI   DEGF     GOTO COMPUTE DEGREES F.
     0254 90DC   0231   0495          BR   RUN1
                        0496 *
     0256 50            0497 DELT     LR   0,A
     0257 203D          0498          LI   0'75'
     0259 51            0499          LR   1,A
                        0500 *
     025A 280000 0000   0501          PI   BSUB     FIND DIFFERENCE OF TWO READINGS.
                        0502 *
     025D 6D            0503          LISL 5
     025E 90D2   0231   0504          BR   RUN1
                        0505 *
                        0506 *  FTU DISPLAY ENCODING
                        0507 *
     0260 62            0508 FEN      LISU 2
     0261 6C            0509          LISL 4
     0262 7F            0510          LIS  15
     0263 F2            0511          NS   2        R2 LO -> R24.
     0264 2A0000 0000   0512          DCI  DENTBL
     0267 8E            0513          ADC
     0268 16            0514          LM
     0269 5E            0515          LR   D,A
     026A 43            0516          LR   A,3
     026B 14            0517          SR   4        R3 HI -> R23.
     026C 2A0000 0000   0518          DCI  DENTBL
     026F 8E            0519          ADC
     0270 16            0520          LM
     0271 5E            0521          LR   D,A
     0272 7F            0522          LIS  15
     0273 F3            0523          NS   3        R3 LO -> R22.
     0274 2A0000 0000   0524          DCI  DENTBL
     0277 8E            0525          ADC
     0278 16            0526          LM
     0279 5E            0527          LR   D,A
     027A 44            0528          LR   A,4
     027B 14            0529          SR   4        R4 HI -> R21.
     027C 2A0000 0000   0530          DCI  DENTBL
     027F 8E            0531          ADC
     0280 16            0532          LM
     0281 5E            0533          LR   D,A
     0282 7F            0534          LIS  15
     0283 F4            0535          NS   4        R4 LO -> R20.
     0284 2A0000 0000   0536          DCI  DENTBL
     0287 8E            0537          ADC
     0288 16            0538          LM
     0289 5E            0539          LR   D,A
     028A 1C            0540          POP
                        0541 *
                        0542 *  SMT DISPLAY ENCODING CONTINUED
                        0543 *
     028B 63            0544 SEN      LISU 3
     028C 68            0545          LISL 0
```

```
FMME SMI  FILE 2  REV 7 APR 82  JAK/DICKEY-JOHN
ERRS  LOC OBJECT ADDR LINE          SOURCE STATEMENT

     028D 42           0546          LR    A,2       R2 LO -> R30 BIT 3.
     028E 2501         0547          CI    1
     0290 9404    0295 0548          BNZ   SE1
     0292 78           0549          LIS   8         SET HALF DIGIT ONLY IF MSD=1.
     0293 EC           0550          XS    S
     0294 5C           0551          LR    S,A
     0295 69           0552 SE1      LISL  1
     0296 43           0553          LR    A,3
     0297 14           0554          SR    4         R3 HI -> R31 (&R32).
     0298 2A000A 000A  0555          DCI   DENTBA
     029B 13           0556          SL    1
     029C 8E           0557          ADC
     029D 73           0558          LIS   3
     029E FC           0559          NS    S
     029F 8C           0560          XM
     02A0 5D           0561          LR    I,A
     02A1 16           0562          LM
     02A2 5C           0563          LR    S,A
     02A3 7F           0564          LIS   15
     02A4 F3           0565          NS    3         R3 LO -> R32.
     02A5 2A001E 001E  0566          DCI   DENTBB
     02A8 8E           0567          ADC
     02A9 16           0568          LM
     02AA EC           0569          XS    S
     02AB 5D           0570          LR    I,A
     02AC 44           0571          LR    A,4
     02AD 14           0572          SR    4         R4 HI -> R33.
     02AE 2A0028 0028  0573          DCI   DENTBC
     02B1 8E           0574          ADC
     02B2 16           0575          LM
     02B3 5C           0576          LR    S,A
     02B4 1C           0577          POP
                       0578 *
                       0579 *
                       0580 ***************************************************************
                       0581 *
                       0582 *  INVALID MODE WAS SELECTED
                       0583 *
                       0584 ***************************************************************
                       0585 *
                       0586 *
     02B5 62           0587 INVAL    LISU  2         LOAD '-----'.
     02B6 6C           0588          LISL  4
     02B7 2080         0589          LI    H'80'
     02B9 5E           0590          LR    D,A
     02BA 8FFE    02B9 0591          BR7   *-1
     02BC 28015B 015B  0592          PI    DSP
     02BF 280000 0000  0593          PI    TD5
     02C2 290157 0157  0594          JMP   DI25
                       0595 *
                       0596 *
                       0597 ***************************************************************
                       0598 *
                       0599 *  DEGREES FAHRENHEIT
                       0600 *
                       0601 ***************************************************************
                       0602 *
```

```
EMME SMT  FILE 2  REV 7 APR 82  JAK/DICKEY-JOHN
ERRS LOC OBJECT ADDR LINE          SOURCE STATEMENT

                      0603  *
      02C5 08         0604  DEGF    LR     K,P
      02C6 67         0605          LISU   7
      02C7 6D         0606          LISL   5
      02C8 20F5       0607          LI     H'F5'      LOAD 4597.
      02CA 5D         0608          LR     I,A
      02CB 2011       0609          LI     H'11'
      02CD 5E         0610          LR     D,A
      02CE 0A         0611          LR     A,IS
      02CF 50         0612          LR     0,A
      02D0 51         0613          LR     1,A
      02D1 28031D 031D 0614         PI     ISET       GOTO FIND LATEST TEMPERATURE.
      02D4 70         0615          CLR
      02D5 CD         0616          AS     I
      02D6 CE         0617          AS     D
      02D7 19         0618          LNK
      02D8 8406   02DF 0619         BZ     DEG1
      02DA 280000 0000 0620         PI     BSUB       DEGREES F = T - 4597.
      02DD 4E         0621          LR     A,D
      02DE 0C         0622          PK
                      0623  *
      02DF 70         0624  DEG1    CLR
      02E0 5D         0625          LR     I,A
      02E1 5E         0626          LR     D,A
      02E2 0C         0627          PK
                      0628  *
                      0629  *
                      0630  *********************************************************
                      0631  *
                      0632  *   DEGREES CELCIUS
                      0633  *
                      0634  *********************************************************
                      0635  *
                      0636  *
      02E3 08         0637  DEGC    LR     K,P
      02E4 67         0638          LISU   7
      02E5 68         0639          LISL   0
      02E6 2039       0640          LI     H'39'      LOAD 5/9 X 2**16 FOR MULT.
      02E8 5D         0641          LR     I,A
      02E9 208E       0642          LI     H'8E'
      02EB 5D         0643          LR     I,A
      02EC 2035       0644          LI     H'35'
      02EE 5D         0645          LR     I,A
      02EF 2013       0646          LI     H'13'      LOAD 4917 FOR SUB.
      02F1 5E         0647          LR     D,A
      02F2 0A         0648          LR     A,IS
      02F3 50         0649          LR     0,A
      02F4 51         0650          LR     1,A
      02F5 28031D 031D 0651         PI     ISET       GOTO FIND LATEST TEMPERATURE.
      02F8 70         0652          CLR
      02F9 CD         0653          AS     I
      02FA CE         0654          AS     D
      02FB 19         0655          LNK
      02FC 84E2   02DF 0656         BZ     DEG1       BR IF TEMPERATURE COUNTS = 0.
                      0657  *
      02FE 280000 0000 0658         PI     BSUB                  T - 4917.
                      0659  *
```

```
EMME SMT  FILE 2  REV 7 APR 82  JAK/DICKEY-JOHN
ERRS  LOC OBJECT ADDR LINE         SOURCE STATEMENT

      0301 2080        0660         LI    H'80'      MOVE SIGN OF BSUB RESULT
      0303 FA          0661         NS    10          TO DEGREES C SIGN FLAG.
      0304 14          0662         SR    4
      0305 50          0663         LR    0,A
      0306 20F7        0664         LI    H'F7'
      0308 FA          0665         NS    10
      0309 E0          0666         XS    0
      030A 5A          0667         LR    10,A       SAVE SIGN OF TEMPERATURE.
                       0668  *
      030B 66          0669         LISU  6          INIT EXPONENT.
      030C 68          0670         LISL  0
      030D 70          0671         CLR
      030E 5C          0672         LR    S,A
                       0673  *
      030F 67          0674         LISU  7
      0310 69          0675         LISL  1
      0311 280000 0000 0676         PI    NRMLZ      TEMPERATURE.
                       0677  *-------------------------------------------------------------
      0314 280000 0000 0678         PI    MULBIN          TEMPERATURE BY 5/9 X 2**16.
                       0679  *-------------------------------------------------------------
      0317 280000 0000 0680         PI    SHRES
      031A 67          0681         LISU  7
      031B 68          0682         LISL  0
      031C 0C          0683         PK               RETURN.
                       0684  *
                       0685  *
                       0686  *  PLACE ISAR AT LATEST TEMPERATURE
                       0687  *
      031D 71          0688  ISET   LIS   1
      031E FB          0689         NS    11         SMT DISPLAYS AN ADJUSTED TEMPERATURE.
      031F 940D   032D 0690         BNZ   IS2        BR IF SMT TEMPERATURE DISP FLAG SET.
                       0691  *
      0321 65          0692         LISU  5
      0322 6F          0693         LISL  7
      0323 70          0694         CLR
      0324 CE          0695         AS    D
      0325 CC          0696         AS    S
      0326 9408   032F 0697         BNZ   IS1        BR IF 56,57 CONTAIN LATEST TEMPERATURE.
      0328 6D          0698         LISL  5
      0329 CE          0699         AS    D
      032A CC          0700         AS    S
      032B 9403   032F 0701         BNZ   IS1        BR IF 54,55 CONTAIN LATEST TEMPERATURE.
      032D 63          0702  IS2    LISU  3
      032E 6E          0703         LISL  6
      032F 1C          0704  IS1    POP
                       0705  *
                       0706  *
                       0707  *************************************************************
                       0708  *
                       0709  *  READ SMT PRODUCT SELECT KBD
                       0710  *
                       0711  *************************************************************
                       0712  *
                       0713  *
      0330 A0          0714  PROD   INS   0          PRODUCT SELECT NOT ALLOWED
      0331 8122   0354 0715         BP    PR1         WHILE SAMPLE IS PRESENT.
      0333 A1          0716         INS   1
```

```
EMME SMT  FILE 2  REV 7 APR 82  JAK/DICKEY-JOHN
ERRS  LOC OBJECT ADDR LINE          SOURCE STATEMENT

      0334 2171        0717          NI    H'71'
      0336 2220        0718          OI    H'20'
      0338 B1          0719          OUTS  1        ENABLE SMT KBD.
      0339 A0          0720          INS   0        READ SMT KBD.
      033A 15          0721          SL    4
      033B 13          0722          SL    1
      033C 12          0723          SR    1
      033D 50          0724          LR    0,A
      033E A1          0725          INS   1
      033F 2151        0726          NI    H'51'
      0341 B1          0727          OUTS  1        DISABLE KBD.
                       0728  *
      0342 40          0729          LR    A,0      CHECK FOR VALID SELECTION.
      0343 2510        0730          CI    H'10'
      0345 8409   034F 0731          BZ    PR2      BR IF PRODUCT A.
      0347 2520        0732          CI    H'20'
      0349 8405   034F 0733          BZ    PR2      BR IF PRODUCT B.
      034B 2540        0734          CI    H'40'
      034D 9406   0354 0735          BNZ   PR1      BR IF NOT PRODUCT C.
                       0736  *
      034F 208F        0737  PR2     LI    H'8F'
      0351 FA          0738          NS    10
      0352 E0          0739          XS    0
      0353 5A          0740          LR    10,A     SAVE NEW PRODUCT SELECTED.
      0354 4A          0741  PR1     LR    A,10
      0355 18          0742          COM
      0356 2170        0743          NI    H'70'
      0358 B4          0744          OUTS  4
      0359 1C          0745          POP
                       0746  *
                       0747          END
 00 ERRS
```

```
                 0001  * EMM3
                 0002  #333333333333333333333333333333333333333333333333333333333333
                 0003  *
                 0004          TITLE 'EMME SMT  FILE 3  REV 23 MAR 82  JAK/DICKEY-JOHN'
                 0005  *       A
                 0006  *
                 0007  *
                 0008  *
                 0009  *
                 0010  *
            0000 0011  ORGIN   RORG  0
                 0012          ENTRY CAL,SETUP,KFECH,TD250,KBDFTU
                 0013          EXTRN FEN,SEN,DSP,EMPTY,EVCLR,PHID,INVAL
                 0014          EXTRN RUNDAT,FFCN,TD5,FM01,DENTBL,DCLR,DIRT1
                 0015          EXTRN DISPT,BTODS,BTODF,WRMDN
                 0016  *
                 0017  *
                 0018  *
                 0019  *
                 0020  ############################################################
                 0021  *
                 0022  *  CONSTANT  MODE
                 0023  *
                 0024  ############################################################
```

EMME SMT FILE 3 REV 23 MAR 82 JAK/DICKEY-JOHN
ERRS LOC OBJECT ADDR LINE        SOURCE STATEMENT

```
                    0025 *
                    0026 *
 0000 7F            0027 CAL    LIS   H'F'
 0001 F8            0028        NS    8
 0002 2507          0029        CI    7
 0004 8104 0009     0030        BP    CA2         BR IF VALID MODE.
 0006 290000 0000   0031 CA1    JMP   INVAL       FCNS 8 & 9 HAVE NO CONSTANT MODE.
                    0032 *
 0009 20CF          0033 CA2    LI    H'CF'
 000B F8            0034        NS    8           CLR EMPTY DONE FLAG.
 000C 58            0035        LR    8,A         CLR SAMPLE DONE FLAG.
 000D 7F            0036        LIS   H'F'
 000E F8            0037        NS    8
 000F 50            0038        LR    0,A
 0010 2801F8 01F8   0039        PI    KFECH       FETCH SELECTED CONSTANT FROM NOVRAM.
 0013 6A            0040        LISL  2
 0014 70            0041        CLR
 0015 50            0042        LR    0,A         SELECT BTOD CONVERSION CONSTANT.
 0016 280000 0000   0043        PI    BTODF       GOTO CONVERT BINARY TO DECIMAL.
 0019 280000 0000   0044        PI    FEN         GOTO ENCODE DECIMAL TO 7-SEGMENT.
 001C 62            0045        LISU  2
 001D 6F            0046        LISL  7
 001E 72            0047        LIS   2
 001F FB            0048        NS    11
 0020 8405 0026     0049        BZ    C7          BR IF K CKSM OK.
 0022 2024          0050        LI    H'24'       LOAD CKSM FAIL AND CONSTANT INDICATORS.
 0024 9002 0027     0051        BR    C17
                    0052 *
 0026 74            0053 C7     LIS   4           LOAD ONLY CONSTANT INDICATOR.
 0027 5C            0054 C17    LR    S,A
 0028 280343 0343   0055        PI    KDP         SET DP FOR SELECTED K.
 002B 280000 0000   0056        PI    DCLR        CLR SMT WHILE IN CAL MODE.
                    0057 *
 002E 280000 0000   0058        PI    DSP         OUTPUT DISPLAY.
                    0059 *
 0031 28019D 019D   0060        PI    KBD         READ FTU KBD.
                    0061 *
 0034 70            0062        CLR
 0035 52            0063        LR    2,A
 0036 53            0064        LR    3,A
 0037 54            0065        LR    4,A
 0038 55            0066        LR    5,A
 0039 56            0067        LR    6,A
 003A 280000 0000   0068        PI    FEN         DISPLAY ZEROES IN ALL BUT LSD OF FTU.
                    0069 *
                    0070 *
 003D 207F          0071        LI    H'7F'
 003F FA            0072        NS    10
 0040 5A            0073        LR    10,A        CLR DATA ENTERED FLAG.
                    0074 *
 0041 280343 0343   0075        PI    KDP         SET DP FOR SELECTED K.
 0044 40            0076        LR    A,0
 0045 9008 004E     0077        BR    C18
                    0078 *
 0047 280000 0000   0079 C16    PI    DSP         OUTPUT DISPLAY.
 004A 28019D 019D   0080        PI    KBD         READ FTU KEYBOARD.
 004D 40            0081        LR    A,0
                    0082 *
 004E 2503          0083 C18    CI    H'3'
```

```
EMME SMT  FILE 3  REV 23 MAR 82  JAK/DICKEY-JOHN
ERRS  LOC OBJECT ADDR LINE          SOURCE STATEMENT

      0050 9404    0055 0084          BNZ   C9        BR  IF NOT STORE FCN.
      0052 2900AC  00AC 0085          JMP   STORE
                        0086  *
      0055 20FE         0087  C9      LI    H'FE'
      0057 FA           0088          NS    10
      0058 5A           0089          LR    10,A      CLR STORE FLAG ALLOWING STORE AGAIN.
      0059 40           0090          LR    A,0
      005A 250B         0091          CI    H'B'
      005C 9404    0061 0092          BNZ   C10       BR IF NOT RUNDATA MODE.
      005E 290000  0000 0093  C11     JMP   WRMDN     EXIT CAL MODE.
                        0094  *
      0061 2507         0095  C10     CI    7
      0063 84FA    005E 0096          BZ    C11       BR IF SETUP MODE.
      0065 250F         0097          CI    H'F'
      0067 84F6    005E 0098          BZ    C11       BR IF CAL MODE.
      0069 2502         0099          CI    2
      006B 84F2    005E 0100          BZ    C11       BR IF DISPLAY MODE.
                        0101  *
      006D 4A           0102          LR    A,10
      006E 2280         0103          OI    H'80'     SET DATA ENTERED FLAG.
      0070 5A           0104          LR    10,A
      0071 2A0000  0000 0105          DCI   FFCN
      0074 40           0106          LR    A,0
      0075 13           0107          SL    1
      0076 8E           0108          ADC
      0077 62           0109          LISU  2         SHIFT DISPLAY DIGITS 1 THRU 5 LEFT
      0078 6C           0110          LISL  4          ONE DIGIT, MSD ROLLS OFF.
      0079 71           0111          LIS   1
      007A FE           0112          NS    D
      007B 50           0113          LR    0,A       SAVE DP4 IF SET.
      007C 20FE         0114          LI    H'FE'
      007E FD           0115          NS    I
      007F E0           0116          XS    0
      0080 5E           0117          LR    D,A       R23 -> R24.
      0081 71           0118          LIS   1
      0082 FE           0119          NS    D
      0083 50           0120          LR    0,A       SAVE DP 3 IF SET.
      0084 20FE         0121          LI    H'FE'
      0086 FD           0122          NS    I
      0087 E0           0123          XS    0
      0088 5E           0124          LR    D,A       R22 -> R23.
      0089 71           0125          LIS   1
      008A FE           0126          NS    D
      008B 50           0127          LR    0,A       SAVE DP 2 IF SET.
      008C 20FE         0128          LI    H'FE'
      008E FD           0129          NS    I
      008F E0           0130          XS    0
      0090 5E           0131          LR    D,A       R21 -> R22.
      0091 71           0132          LIS   1
      0092 FE           0133          NS    D
      0093 50           0134          LR    0,A       SAVE DP 1 IF SET.
      0094 20FE         0135          LI    H'FE'
      0096 FD           0136          NS    I
      0097 E0           0137          XS    0
      0098 5E           0138          LR    D,A       R20 -> R21.
      0099 16           0139          LM              LOAD 7-SEG CODE FOR NEWEST DIGIT
      009A 5C           0140          LR    S,A        INTO LSD REGISTER, R20.
      009B 45           0141          LR    A,5
```

```
FMME SMT  FILE 3  REV 23 MAR 82  JAK/DICKEY-JOHN
ERRS  LOC OBJECT ADDR LINE         SOURCE STATEMENT

      009C 14          0142          SR    4
      009D 54          0143          LR    4,A
      009E 45          0144          LR    A,5     SHIFT SAME NUMBER IN DECIMAL
      009F 15          0145          SL    4        LEFT ONE DIGIT.
      00A0 55          0146          LR    5,A
      00A1 46          0147          LR    A,6
      00A2 14          0148          SR    4
      00A3 E5          0149          XS    5
      00A4 55          0150          LR    5,A
      00A5 46          0151          LR    A,6
      00A6 15          0152          SL    4
      00A7 8C          0153          XM
      00A8 56          0154          LR    6,A
      00A9 290047 0047 0155          JMP   C16
                       0156 *
                       0157 * STORE CONSTANT IN RAM
                       0158 *
      00AC 71          0159 STORE    LIS   1
      00AD FA          0160          NS    10
      00AE 8404   00B3 0161          BZ    S3      BR IF STORE WASN'T LAST FCN DONE.
      00B0 290000 0000 0162          JMP   CAL
                       0163 *
      00B3 70          0164 S3       CLR
      00B4 CA          0165          AS    10
      00B5 9104   00BA 0166          BM    S4      BR IF NEW CAL ENTERED.
      00B7 290145 0145 0167          JMP   S2
                       0168 *
      00BA 62          0169 S4       LISU  2
      00BB 6C          0170          LISL  4
      00BC 2080        0171          LI    H'80'
      00BE 5E          0172          LR    D,A
      00BF 8FFE   00BE 0173          BR7   *-1
      00C1 280000 0000 0174          PI    DSP     DISPLAY '-----'.
                       0175 *                      CONVERT TO BINARY.
      00C4 44          0176          LR    A,4     #5
      00C5 50          0177          LR    0,A
      00C6 2010        0178          LI    H'10'
      00C8 51          0179          LR    1,A     LOAD ADDER VALUE.
      00C9 2027        0180          LI    H'27'
      00CB 52          0181          LR    2,A
      00CC 70          0182          CLR
      00CD 53          0183          LR    3,A
      00CE 54          0184          LR    4,A
      00CF 28018E 018E 0185          PI    DTB
      00D2 45          0186          LR    A,5
      00D3 14          0187          SR    4       #4
      00D4 50          0188          LR    0,A
      00D5 20E8        0189          LI    H'E8'   LOAD ADDER VALUE.
      00D7 51          0190          LR    1,A
      00D8 73          0191          LIS   3
      00D9 52          0192          LR    2,A
      00DA 28018E 018E 0193          PI    DTB
      00DD 7F          0194          LIS   15
      00DE F5          0195          NS    5       #3
      00DF 50          0196          LR    0,A
      00E0 2064        0197          LI    100     LOAD ADDER VALUE.
      00E2 51          0198          LR    1,A
```

```
EMME SMT  FILE 3  REV 23 MAR 82  JAK/DICKEY JOHN
ERRS  LOC OBJECT ADDR LINE          SOURCE STATEMENT

      00E3 70           0199          CLR
      00E4 52           0200          LR    2,A
      00E5 28018E 018E  0201          PI    DTB
      00E8 46           0202          LR    A,6
      00E9 14           0203          SR    4          #2
      00EA 50           0204          LR    0,A
      00EB 7A           0205          LIS   10         LOAD ADDER VALUE.
      00EC 51           0206          LR    1,A
      00ED 28018E 018E  0207          PI    DTB
      00F0 7F           0208          LIS   15
      00F1 F6           0209          NS    6
      00F2 50           0210          LR    0,A        #1
      00F3 71           0211          LIS   1
      00F4 51           0212          LR    1,A        LOAD ADDER VALUE.
      00F5 28018E 018E  0213          PI    DTB
      00F8 4B           0214          LR    A,11
      00F9 12           0215          SR    1
      00FA 12           0216          SR    1
      00FB 51           0217          LR    1,A        ADDRESS OF K TO BE STORED.
                        0218  *
      00FC 60           0219          LISU  0
      00FD 2521         0220          CI    H'21'      CHECK FOR A 2 NIBBLE CONSTANT.
      00FF 9405   0105  0221          BNZ   S5         BR IF NOT ADDR OF PROD 3 CKSM.
      0101 6C           0222  S8      LISL  4
      0102 72           0223          LIS   2          LOAD NIBBLE COUNT OF 2.
      0103 9017   011B  0224          BR    S6
      0105 2511         0225  S5      CI    H'11'
      0107 84F9   0101  0226          BZ    S8         BR IF ADDR OF PROD 2 CKSM.
      0109 2501         0227          CI    1
      010B 84F5   0101  0228          BZ    S8         BR IF ADDR OF PROD 1 CKSM.
      010D 250F         0229          CI    H'F'
      010F 84F1   0101  0230          BZ    S8         BR IF ADDR OF PROD 1 K4.
      0111 251F         0231          CI    H'1F'
      0113 84ED   0101  0232          BZ    S8         BR IF ADDR OF PROD 2 K4.
      0115 252F         0233          CI    H'2F'
      0117 84E9   0101  0234          BZ    S8         BR IF ADDR OF PROD 3 K4.
                        0235  *
      0119 6E           0236          LISL  6
      011A 74           0237          LIS   4          LOAD NIBBLE COUNT OF 4.
      011B 50           0238  S6      LR    0,A
                        0239  *
      011C 44           0240          LR    A,4        RECONFIGURE DATA FOR OUTPUT TO RAM.
      011D 14           0241          SR    4
      011E 56           0242          LR    6,A
      011F 7F           0243          LIS   15
      0120 F4           0244          NS    4
      0121 55           0245          LR    5,A
      0122 43           0246          LR    A,3
      0123 14           0247          SR    4
      0124 54           0248          LR    4,A
      0125 7F           0249          LIS   15
      0126 F3           0250          NS    3
      0127 53           0251          LR    3,A
                        0252  *
      0128 0F           0253          LR    DC,Q       SAVE Q REGISTERS.
      0129 2C           0254          XDC
                        0255  *
```

```
EMME SMT  FILE 3  REV 23 MAR 82 - JAK/DICKEY-JOHN
ERRS  LOC OBJECT ADDR LINE          SOURCE STATEMENT

      012A 47           0256  S10    LR    A,7
      012B 2204         0257         OI    4
      012D 57           0258         LR    7,A      SET RAM WRITE FLAG.
                        0259  *
      012E 4E           0260         LR    A,D
      012F 59           0261         LR    9,A      DATA NIBBLE INTO DATA OUT REGISTER.
      0130 2A02C8 02C8  0262         DCI   RAM
      0133 0E           0263         LR    Q,DC     LOAD ADDRESS OF SUBROUTINE - RAM.
      0134 2A0138 0138  0264         DCI   S9       POINT TO RETURN ADDRESS.
      0137 0D           0265         LR    P0,Q     GOTO OUTPUT DATA.
                        0266  *
      0138 31           0267  S9     DS    1        DECREMENT ADDRESS.
      0139 30           0268         DS    0        DECREMENT NIBBLE COUNTER.
      013A 94EF   012A  0269         BNZ   S10      BR IF MORE NIBBLES.
                        0270  *
      013C 66           0271         LISU  6
      013D 69           0272         LISL  1
      013E 4C           0273         LR    A,S
      013F 2504         0274         CI    4
      0141 910D   014F  0275         BM    S11      BR IF K5 THRU K7.
                        0276  *
      0143 2C           0277         XDC
      0144 0E           0278         LR    Q,DC     RESTORE Q REGISTERS.
                        0279  *
      0145 280000 0000  0280  S2     PI    TD5      DELAY .5 SECONDS.
      0148 4A           0281         LR    A,10
      0149 2201         0282         OI    1
      014B 5A           0283         LR    10,A     SET STORE FLAG.
      014C 290000 0000  0284         JMP   CAL      GOTO RECALL NEW CONSTANT.
                        0285  *
                        0286  *  COMPUTE CKSM ON K5 THRU K7
                        0287  *
      014F 20FB         0288  S11    LI    H'FB'
      0151 F7           0289         NS    7
      0152 57           0290         LR    7,A      CLR RAM WRITE FLAG.
      0153 203B         0291         LI    H'3B'
      0155 51           0292         LR    1,A      LOAD ADDRESS.
      0156 76           0293         LIS   6
      0157 50           0294         LR    0,A      LOAD BYTE COUNT.
                        0295  *
      0158 70           0296         CLR
      0159 53           0297         LR    3,A      CLR ACCUMULATOR.
                        0298  *
      015A 2A02C8 02C8  0299  S14    DCI   RAM
      015D 0E           0300         LR    Q,DC     LOAD ADDRESS OF SUBROUTINE - RAM.
      015E 2A0162 0162  0301         DCI   S12      POINT TO RETURN ADDRESS.
      0161 0D           0302         LR    P0,Q     GOTO READ RAM.
                        0303  *
      0162 49           0304  S12    LR    A,9
      0163 15           0305         SL    4
      0164 54           0306         LR    4,A
      0165 31           0307         DS    1        DECREMENT ADDRESS.
                        0308  *
      0166 2A02C8 02C8  0309         DCI   RAM
      0169 0E           0310         LR    Q,DC     LOAD ADDRESS OF SUBROUTINE - RAM.
      016A 2A016E 016E  0311         DCI   S13      POINT TO RETURN ADDRESS.
      016D 0D           0312         LR    P0,Q     GOTO READ RAM.
                        0313  *
```

```
EMME SMT  FILE 3  REV 23 MAR 82  JAK/DICKEY JOHN
ERRS  LOC OBJECT ADDR LINE          SOURCE STATEMENT

      016E 49          0314  S13    LR    A,9
      016F E4          0315         XS    4
      0170 C3          0316         AS    3
      0171 53          0317         LR    3,A      UPDATE ACCUMULATOR.
                       0318  *
      0172 31          0319         DS    1        DECREMENT ADDRESS.
      0173 30          0320         DS    0        DECREMENT BYTE COUNT.
      0174 94E5   015A 0321         BNZ   S14      BR IF MORE BYTES TO ADD.
                       0322  *
      0176 43          0323         LR    A,3
      0177 18          0324         COM
      0178 1F          0325         INC
      0179 2455        0326         AI    H'55'
      017B 53          0327         LR    3,A      COMPUTE CKSM.
      017C 14          0328         SR    4
      017D 54          0329         LR    4,A
      017E 7F          0330         LIS   15
      017F F3          0331         NS    3
      0180 53          0332         LR    3,A
      0181 72          0333         LIS   2
      0182 50          0334         LR    0,A      LOAD NIBBLE COUNT OF 2.
      0183 203D        0335         LI    H'3D'
      0185 51          0336         LR    1,A      LOAD ADDRESS OF K5 THRU K7 CKSM.
                       0337  *
      0186 66          0338         LISU  6
      0187 69          0339         LISL  1
      0188 70          0340         CLR            CLR K5-K7 INDICATION.
      0189 5C          0341         LR    S,A
      018A 60          0342         LISU  0
      018B 6C          0343         LISL  4        SET POINTER TO CKSM.
      018C 909D   012A 0344         BR    S10
                       0345  *
                       0346  *
                       0347  *  DECIMAL TO BINARY COUNTING LOOP
                       0348  *
      018E 70          0349  DTB    CLR            R 0 - INCOMING DIGIT.
      018F C0          0350         AS    0        R 1,2 - ADDER VALUE.
      0190 840B   019C 0351         BZ    DTB1     R 3,4 - BINARY OUTPUT.
      0192 43          0352  DTB2   LR    A,3      (LO,HI)
      0193 C1          0353         AS    1
      0194 53          0354         LR    3,A
      0195 44          0355         LR    A,4
      0196 19          0356         LNK
      0197 C2          0357         AS    2
      0198 54          0358         LR    4,A
      0199 30          0359         DS    0
      019A 94F7   0192 0360         BNZ   DTB2
      019C 1C          0361  DTB1   POP
                       0362  *
                       0363  *
                       0364  *  FTU KEYBOARD READING
                       0365  *
      019D 08          0366  KBD    LR    K,P
      019E A1          0367         INS   1
      019F 15          0368         SL    4
      01A0 81FD   019E 0369         BP    *-2      WAIT FOR CLR KBD.
      01A2 A5          0370  KBD2   INS   5
```

```
EMME SMT FILE 3 REV 23 MAR 82 JAN/DUFFEY JOHN
ERRS LOC OBJECT ADDR LINE          SOURCE STATEMENT

     01A3 9109    01AD 0371          BM    KBD1      BR IF EMME SWITCH DEPRESSED.
     01A5 A1           0372          INS   1
     01A6 15           0373          SL    4
     01A7 91FA    01A2 0374          BM    KBD2      BR IF FTU KEY NOT DEPRESSED.
                       0375 *  ENTRY MADE
     01A9 2801B0 01B0 0376           PI    KBDFTU
     01AC 0C           0377          PK
                       0378 *
     01AD 2902F3 02F3 0379 KBD1      JMP   STPSTO    JMP FOR ARRAY STORE.
                       0380 *
                       0381 *
                       0382 *************************************************************
                       0383 *
                       0384 *  FTU KEYBOARD INPUT
                       0385 *
                       0386 *************************************************************
                       0387 *
                       0388 *
     01B0 203F         0389 KBDFTU   LI    H'3F'
     01B2 B5           0390          OUTS  5         ENABLE FTU KBD.
     01B3 A0           0391          INS   0         INPUT KEYBOARD SELECTION.
     01B4 18           0392          COM
     01B5 15           0393          SL    4
     01B6 14           0394          SR    4
     01B7 50           0395          LR    0,A       SAVE KEY# IN R0.
     01B8 207F         0396          LI    H'7F'
     01BA B5           0397          OUTS  5         DISABLE FTU.
     01BB 1C           0398          POP
                       0399 *
                       0400 *
                       0401 *************************************************************
                       0402 *
                       0403 *  SMT SETUP MODE V-F UNMODIFIED READOUT
                       0404 *
                       0405 *************************************************************
                       0406 *
                       0407 *
     01BC 7F           0408 SETUP    LIS   15
     01BD F8           0409          NS    8
     01BE 8410    01CF 0410          BZ    SE1       BR IF TEMPERATURE.
     01C0 2501         0411          CI    1
     01C2 8410    01D3 0412          BZ    SE2       BR IF EMPTY CELL DATA.
     01C4 2502         0413          CI    2
     01C6 8410    01D7 0414          BZ    SE3       BR IF EC + REFR DATA.
     01C8 2509         0415          CI    9
     01CA 8410    01DB 0416          BZ    SE4       BR IF OFFSET DATA.
     01CC 290000 0000 0417           JMP   INVAL
                       0418 *                      LOAD CELL SETUP CODES.
     01CF 2010         0419 SE1      LI    H'10'
     01D1 900B    01DD 0420          BR    SE7
                       0421 *
     01D3 2011         0422 SE2      LI    H'11'
     01D5 9007    01DD 0423          BR    SE7
                       0424 *
     01D7 2051         0425 SE3      LI    H'51'
     01D9 9003    01DD 0426          BR    SE7
                       0427 *
```

```
EMME SMT  FILE 3  REV 23 MAR 82  JAK/DICKEY-JOHN
ERRS  LOC OBJECT ADDR LINE          SOURCE STATEMENT

      01DB 2001           0428  SE4     LI    H'01'
                          0429  *
      01DD B1             0430  SE7     OUTS  1         OUTPUT SETUP CODE.
      01DE 62             0431          LISU  2
      01DF 6F             0432          LISL  7
      01E0 70             0433          CLR
      01E1 5C             0434          LR    S,A       CLR DATA TYPE INDICATOR.
      01E2 280000 0000 0435             PI    DCLR      CLR SMT DISPLAY REGISTERS.
      01E5 280000 0000 0436             PI    EVCLR     CLR EVENT COUNTERS.
      01E8 280000 0000 0437             PI    PHID      COLLECT PHID DATA.
      01EB 6A             0438          LISL  2
      01EC 280000 0000 0439             PI    BTODF     GOTO CONVERT BINARY TO DECIMAL.
      01EF 280000 0000 0440             PI    FEN       GOTO ENCODE DECIMAL TO 7-SEGMENT.
      01F2 280000 0000 0441             PI    DSP       OUTPUT DISPLAY.
      01F5 290000 0000 0442             JMP   WRMDN     LEAVE SETUP MODE.
                          0443  *
                          0444  *
                          0445  *************************************************************
                          0446  *
                          0447  *  SINGLE CONSTANT FETCH FROM EXTERNAL RAM
                          0448  *  RO CONTAINS K TO BE FETCHED; RESULT IN R4,5,6
                          0449  *                                          CKSM,MSB,LSB
                          0450  *
                          0451  ***************************************************************
                          0452  *
                          0453  *
                          0454  *  CHECK THE CKSM BEFORE FETCHING CONSTANTS
                          0455  *
      01F8 40             0456  KFECH   LR    A,0
      01F9 2504           0457          CI    4
      01FB 9149      0245 0458          BM    KFC1      BR IF K5 THRU K7.
                          0459  *
      01FD 4A             0460          LR    A,10
      01FE 13             0461          SL    1
      01FF 8105      0205 0462          BP    KFC2      BR IF NOT PRODUCT C CKSM.
      0201 202F           0463          LI    H'2F'
      0203 9009      020D 0464          BR    KFC3
                          0465  *
      0205 13             0466  KFC2    SL    1
      0206 8105      020C 0467          BP    KFC4      BR IF NOT PRODUCT B CKSM.
      0208 201F           0468          LI    H'1F'
      020A 9002      020D 0469          BR    KFC3
                          0470  *
      020C 7F             0471  KFC4    LIS   H'F'
                          0472  *
      020D 51             0473  KFC3    LR    1,A       LOAD ADDRESS.
      020E 78             0474          LIS   8
      020F 52             0475  KFC8    LR    2,A       LOAD BYTE COUNT.
      0210 70             0476          CLR
      0211 53             0477          LR    3,A
                          0478  *
      0212 0F             0479          LR    DC,Q      SAVE Q REGISTERS.
      0213 2C             0480          XDC
                          0481  *
      0214 20FB           0482          LI    H'FB'
      0216 F7             0483          NS    7
      0217 57             0484          LR    7,A       CLR RAM WRITE FLAG.
                          0485  *
```

```
EMME SMT FILE 3 REV 23 MAR 82 JAK/DICKEY-JOHN
ERRS LOC OBJECT ADDR LINE          SOURCE STATEMENT

0218 2A02C8 02C8 0486 KFC7    DCI   RAM
021B 0E          0487         LR    Q,DC      LOAD ADDRESS OF SUBROUTINE - RAM.
021C 2A0220 0220 0488         DCI   KFC5      POINT TO RETURN ADDRESS.
021F 0D          0489         LR    P0,Q      GOTO READ NIBBLE.
                 0490 *
0220 49          0491 KFC5    LR    A,9
0221 15          0492         SL    4
0222 54          0493         LR    4,A
0223 31          0494         DS    1         DECREMENT ADDRESS.
                 0495 *
0224 2A02C8 02C8 0496         DCI   RAM
0227 0E          0497         LR    Q,DC      LOAD ADDRESS OF SUBROUTINE - RAM.
0228 2A022C 022C 0498         DCI   KFC6      POINT TO RETURN ADDRESS.
022B 0D          0499         LR    P0,Q      GOTO READ RAM.
                 0500 *
022C 49          0501 KFC6    LR    A,9
022D E4          0502         XS    4
022E C3          0503         AS    3         SUM DATA BYTES.
022F 53          0504         LR    3,A
0230 31          0505         DS    1         DECREMENT ADDRESS.
0231 32          0506         DS    2         DECREMENT BYTE COUNT.
0232 94E5   0218 0507         BNZ   KFC7      BR IF MORE NIBBLES.
                 0508 *
0234 43          0509         LR    A,3
0235 2555        0510         CI    H'55'
0237 8407   023F 0511         BZ    KFC9      BR IF CONSTANTS OK.
                 0512 *
0239 4B          0513         LR    A,11
023A 2202        0514         OI    2
023C 5B          0515         LR    11,A      SET K FAIL FLAG.
023D 900D   024B 0516         BR    KFE
                 0517 *
023F 20FD        0518 KFC9    LI    H'FD'     CLR K FAIL FLAG.
0241 FB          0519         NS    11
0242 5B          0520         LR    11,A
0243 9007   024B 0521         BR    KFE
                 0522 *
0245 203D        0523 KFC1    LI    H'3D'
0247 51          0524         LR    1,A       LOAD ADDR FOR K5-K7.
0248 77          0525         LIS   7
0249 90C5   020F 0526         BR    KFC8
                 0527 *
                 0528 *  FETCH CONSTANT
                 0529 *
024B 40          0530 KFE     LR    A,0
024C 2504        0531         CI    4
024E 9105   0254 0532         BM    KF1       BR IF K5,K6,K7.
                 0533 *
0250 4A          0534         LR    A,10
0251 13          0535         SL    1
0252 8112   0265 0536         BP    KF2       BR IF NOT PRODUCT C.
0254 2A02A4 02A4 0537 KF1     DCI   KTAB1     PRODUCT C TABLE.
0257 40          0538 KF5     LR    A,0
0258 13          0539         SL    1
0259 8E          0540         ADC
025A 16          0541         LM
025B 51          0542         LR    1,A       LOAD ADDRESS INTO R1.
```

```
EMME SMT  FILE 3  REV 2? MAR 82  JAK/DILKEY-JOHN
ERRS  LOC OBJECT ADDR LINE          SOURCE STATEMENT

      025C 13          0543          SL    1
      025D 13          0544          SL    1
      025E 52          0545          LR    2,A
      025F 73          0546          LIS   3
      0260 FB          0547          NS    11
      0261 E2          0548          XS    2
      0262 5B          0549          LR    11,A      SAVE ADDRESS OF CURRENT CONSTANT.
      0263 900E   0272 0550          BR    KF3
                       0551  *
      0265 13          0552  KF2     SL    1
      0266 8106   026D 0553          BP    KF4       BR IF NOT PRODUCT B.
      0268 2A02B4 02B4 0554          DCI   KTAB2     PODUCT B TABLE.
      026B 90EB   0257 0555          BR    KF5
                       0556  *
      026D 2A02BE 02BE 0557  KF4     DCI   KTAB3     PRODUCT A TABLE.
      0270 90E6   0257 0558          BR    KF5
                       0559  *
      0272 66          0560  KF3     LISU  6
      0273 69          0561          LISL  1
      0274 70          0562          CLR
      0275 C0          0563          AS    0
      0276 5C          0564          LR    S,A       SAVE K0.
      0277 60          0565          LISU  0
      0278 9404   027D 0566          BNZ   KF8       BR IF NOT K0.
      027A 6C          0567  KF10    LISL  4         LOAD ISAR LESS 2 FOR K0.
      027B 9006   0282 0568          BR    KF9
                       0569  *
      027D 2504        0570  KF8     CI    4
      027F 84FA   027A 0571          BZ    KF10      BR IF FOR K4.
      0281 6E          0572          LISL  6
      0282 16          0573  KF9     LM
      0283 50          0574          LR    0,A       LOAD NIBBLE COUNTS.
      0284 70          0575          CLR
      0285 53          0576          LR    3,A
      0286 54          0577          LR    4,A
      0287 55          0578          LR    5,A
      0288 56          0579          LR    6,A
                       0580  *
      0289 2A02C8 02C8 0581  KF7     DCI   RAM
      028C 0E          0582          LR    Q,DC      LOAD ADDRESS OF SUBROUTINE - RAM.
      028D 2A0291 0291 0583          DCI   KF6       POINT TO RETURN ADDRESS.
      0290 0D          0584          LR    P0,Q      GOTO RAM.
                       0585  *
      0291 49          0586  KF6     LR    A,9
      0292 5E          0587          LR    D,A
      0293 31          0588          DS    1         DECREMENT ADDRESS.
      0294 30          0589          DS    0         DECREMENT NIBBLE COUNT.
      0295 94F3   0289 0590          BNZ   KF7       BR IF MORE NIBBLES.
                       0591  *
      0297 67          0592          LISU  7
      0298 6B          0593          LISL  3
      0299 46          0594          LR    A,6       PACK CONSTANT INTO 16-BIT NUMBER.
      029A 15          0595          SL    4
      029B E5          0596          XS    5
      029C 5E          0597          LR    D,A
      029D 44          0598          LR    A,4
      029E 15          0599          SL    4
```

```
EMME SMT  FILE 3  REV 23 MAR 82  JAK/DICKEY-JOHN
ERRS  LOC OBJECT ADDR LINE          SOURCE STATEMENT

        029F E3            0600           XS    3
        02A0 5D            0601           LR    I,A
        02A1 2C            0602           XDC
        02A2 0E            0603           LR    Q,DC        RESTORE Q REGISTERS.
        02A3 1C            0604           POP
                           0605  *
                           0606  *
        02A4 210225        0607  KTAB1    DC    H'2102250429042D04'
        02AC 2F0233        0608           DC    H'2F02330437043B04'
                           0609  *
        02B4 110215        0610  KTAB2    DC    H'1102150419041D04'
        02BC 1F02          0611           DC    H'1F02'
                           0612  *
        02BE 010205        0613  KTAB3    DC    H'0102050409040D04'
        02C6 0F02          0614           DC    H'0F02'
                           0615  *
                           0616  *             ADDRESS,NIBBLES
                           0617  *
                           0618  *
                           0619  *
                           0620  ***********************************************************
                           0621  *
                           0622  *  OUTPUT TO OR INPUT FROM NOVRAM
                           0623  *
                           0624  ***********************************************************
                           0625  *
                           0626  *
        02C8 41            0627  RAM      LR    A,1
        02C9 18            0628           COM
        02CA 2240          0629           OI    H'40'
        02CC B5            0630           OUTS  5           ADDRESS OUT.
        02CD A4            0631           INS   4
        02CE 2170          0632           NI    H'70'
        02D0 2208          0633           OI    8
        02D2 B4            0634           OUTS  4           CHIP SELECT.
        02D3 74            0635           LIS   4
        02D4 F7            0636           NS    7
        02D5 8416    02EC  0637           BZ    READ        BR TO INPUT DATA.
                           0638  *
        02D7 49            0639           LR    A,9         HERE TO OUTPUT DATA.
        02D8 2270          0640           OI    H'70'
        02DA B0            0641           OUTS  0           DATA OUTPUT.
        02DB A4            0642           INS   4
        02DC 2178          0643           NI    H'78'
        02DE 2204          0644           OI    4
        02E0 B4            0645           OUTS  4           WRITE ENABLE.
        02E1 2170          0646  RA1      NI    H'70'
        02E3 B4            0647           OUTS  4           DISABLE WRITE, DISABLE CHIP.
        02E4 207F          0648           LI    H'7F'
        02E6 B5            0649           OUTS  5           CLR ADDRESS LINES.
        02E7 2070          0650           LI    H'70'
        02E9 B0            0651           OUTS  0           CLR DATA LINES.
                           0652  *
        02EA 0E            0653           LR    Q,DC        LOAD RETURN ADDRESS.
        02EB 0D            0654           LR    P0,Q        RETURN.
                           0655  *
        02EC A0            0656  READ     INS   0           INPUT DATA.
        02ED 15            0657           SL    4
```

```
EMME SMT  FILE 3  REV 23 MAR 82  JAK/DICKEY-JOHN
ERRS  LOC OBJECT ADDR          SOURCE STATEMENT

      02EE 14                        SR    4
      02EF 59                        LR    9,A
      02F0 A4                        INS   4
      02F1 90EF   02E1               BR    RA1
                           *
                           *
                           ***************************************************************
                           *
                           *  EXTERNAL COPY OF RAM TO ROM FOR PERMANENT CONSTANT STORAGE
                           *
                           ***************************************************************
                           *
                           *
      02F3 62              STPSTO    LISU  2         DISPLAY ZEROES FOR FTU DIGITS 1 THRU 5.
      02F4 6C                        LISL  4
      02F5 207E                      LI    H'7E'
      02F7 5E                        LR    D,A
      02F8 8FFE   02F7               BR7   *-1
      02FA 280000 0000               PI    DSP       OUTPUT DISPLAY.
                           *
      02FD A5              ST3       INS   5         CHECK STEP SWITCH ON SMT.
      02FE 9104   0303               BM    ST1       BR IF STEP SWITCH DEPRESSED.
      0300 290000 0000               JMP   CAL       EXIT IF STEP SWITCH RELEASED.
                           *
      0303 A1              ST1       INS   1
      0304 15                        SL    4
      0305 91F7   02FD               BM    ST3       BR IF NO FTU KEY DEPRESSED.
      0307 2801B0 01B0               PI    KBDFTU    READ FTU KBD.
      030A 40                        LR    A,0
      030B 2503                      CI    3
      030D 94EF   02FD               BNZ   ST3       BR IF NO STORE COMMAND.
                           *
      030F 62                        LISU  2
      0310 6F                        LISL  7
      0311 2080                      LI    H'80'     ELSE,
      0313 5E                        LR    D,A       LOAD DASHES FOR DISPLAY.
      0314 8FFE   0313               BR7   *-1
      0316 280000 0000               PI    DSP       OUTPUT DISPLAY UPDATE.
      0319 A4                        INS   4
      031A 2170                      NI    H'70'
      031C 1F                        INC
      031D B4                        OUTS  4         STORE NONVOLATILE.
      031E 12                        SR    1
      031F 13                        SL    1
      0320 B4                        OUTS  4         END STORE PULSE.
      0321 280337 0337               PI    TD250     DELAY 250 MS.
      0324 A1                        INS   1
      0325 15                        SL    4
      0326 81FD   0324               BP    *-2       WAIT HERE TIL STORE NO LONGER DEPRESSED.
                           *
      0328 62                        LISU  2         RESTORE K INDICATOR AND BLANK.
      0329 6D                        LISL  5
      032A 70                        CLR
      032B 5D                        LR    I,A
      032C 2A0000 0000               DCI   DENTBL
      032F 7F                        LIS   15
      0330 F8                        NS    8
```

```
EMME SMT  FILE 3  REV 23 MAR 82  JAK/DICKEY JOHN
ERRS  LOC OBJECT ADDR LINE         SOURCE STATEMENT
      0331 8E           0715          ADC
      0332 16           0716          LM
      0333 5C           0717          LR    S,A       RESTORE CONSTANT NUMBER.
      0334 290000 0000  0718          JMP   CAL       GOTO RECALL CONSTANT.
                        0719 *
                        0720 *
                        0721 ***********************************************************
                        0722 *
                        0723 *  250 MILLISECOND DELAY
                        0724 *
                        0725 ***********************************************************
                        0726 *
                        0727 *
      0337 2061         0728 TD250    LI    97
      0339 50           0729          LR    0,A
      033A 70           0730          CLR
      033B 51           0731          LR    1,A
      033C 31           0732          DS    1
      033D 94FE    033C 0733          BNZ   *-1
      033F 30           0734          DS    0
      0340 94FB    033C 0735          BNZ   *-4
      0342 1C           0736          POP
                        0737 *
                        0738 *
                        0739 ***********************************************************
                        0740 *
                        0741 *  SET DECIMAL POINT FOR SELECTED CONSTANT
                        0742 *
                        0743 ***********************************************************
                        0744 *
                        0745 *
      0343 62           0746 KDP      LISU  2
      0344 7F           0747          LIS   15
      0345 F8           0748          NS    8
      0346 8417    035E 0749          BZ    KD2       BR IF NO DP.
      0348 2503         0750          CI    3
      034A 8107    0352 0751          BP    KD1       BR IF NOT K4,K5,K6,K7.
      034C 6C           0752          LISL  4
      034D 4C           0753          LR    A,S
      034E 1F           0754          INC
      034F 5C           0755          LR    S,A       SET DP X.XXXX
      0350 900D    035E 0756          BR    KD2
                        0757 *
      0352 9407    035A 0758 KD1      BNZ   KD3       BR IF NOT K3.
      0354 6B           0759          LISL  3
      0355 4C           0760          LR    A,S
      0356 1F           0761          INC
      0357 5C           0762          LR    S,A       SET DP XX.XXX
      0358 9005    035E 0763          BR    KD2
                        0764 *
      035A 6A           0765 KD3      LISL  2         HERE FOR K1 OR K2.
      035B 4C           0766          LR    A,S
      035C 1F           0767          INC
      035D 5C           0768          LR    S,A       SET DP XXX.XX
                        0769 *
      035E 1C           0770 KD2      POP
                        0771 *
                        0772          END
00 ERRS
```

```
EMME SMT  FILE 4  REV 13 APR 82 JAK/DICKEY-JOHN
ERRS  LOC OBJECT ADDR LINE            SOURCE STATEMENT

                      0001  * EMM4
                      0002  *44444444444444444444444444444444444444444444444444444444444444444444
                      0003  *
                      0004              TITLE 'EMME SMT  FILE 4  REV 13 APR 82 JAK/DICKEY-JOHN'
                      0005  *           A
                      0006  *
                      0007  *
                      0008  *
                      0009  *
                      0010  *
                 0000 0011  ORGIN      RORG  0
                      0012             ENTRY BTODS,BTODF,PHID,CELL,ERCLR,BPOS,TCELL
                      0013             ENTRY ERROR,TD5,TD1S,TD10MS
                      0014             EXTRN EMPTY,SAMPLE,DIRT,WRMUP,PREM,EVCLR,BSUB
                      0015             EXTRN SCLR,DSP
                      0016  *
                      0017  *
                      0018  *
                      0019  *
                      0020  *
                      0021  *****************************************************************
                      0022  *
                      0023  *  BINARY TO DECIMAL CONVERSION
                      0024  *  INPUT IS, IS+1
                      0025  *  OUTPUT MSD 2,3,4,5,6 LSD
                      0026  *  ADDER LSD 71,72,73,74,75 MSD
                      0027  *
                      0028  *  ADDER = .00001526 FOR EMME#
                      0029  *           .1 FOR % OR DEGREES
                      0030  *           .01 FOR ALL OTHER NUMBERS
                      0031  *
                      0032  *****************************************************************
                      0033  *
                      0034  *
     0000 75          0035  BTODS    LIS   5
     0001 54          0036           LR    4,A
     0002 70          0037           CLR
     0003 55          0038           LR    5,A
     0004 9006   000B 0039           BR    BT4
     0006 2050        0040  BTODF    LI    H'50'
     0008 55          0041           LR    5,A
     0009 70          0042           CLR
     000A 54          0043           LR    4,A
     000B 2A008C 008C 0044  BT4      DCI   DK
     000E 40          0045           LR    A,0      R0=0 FOR ALL BUT EMME#, THEN=4.
     000F 8E          0046           ADC
     0010 4D          0047           LR    A,I
     0011 50          0048           LR    0,A      MOVE DATA FROM INCOMING REGISTERS
     0012 4C          0049           LR    A,S       TO R76,77.
     0013 67          0050           LISU  7
     0014 6F          0051           LISL  7
     0015 5E          0052           LR    D,A
     0016 40          0053           LR    A,0
     0017 5C          0054           LR    S,A
     0018 70          0055           CLR             CLR RESULT REGISTERS.
     0019 52          0056           LR    2,A      MSB RESULT.
     001A 53          0057           LR    3,A
```

```
FMME SMI  FILE 4  REV 13 APR 82 JAK/DIFFEY JOHN
ERRS  LOC OBJECT ADDR LINE          SOURCE STATEMENT

      001B 56          0058         LR    6,A      LSB RESULT.
      001C 6D          0059         LISL  5
      001D 16          0060         LM
      001E 5E          0061         LR    D,A
      001F 16          0062         LM
      0020 5E          0063         LR    D,A
      0021 16          0064         LM
      0022 5E          0065         LR    D,A
      0023 16          0066         LM
      0024 5E          0067         LR    D,A
      0025 16          0068         LM
      0026 5E          0069         LR    D,A
                       0070  *
      0027 6E          0071  BT1    LISL  6
      0028 4D          0072         LR    A,I
      0029 CE          0073         AS    D
      002A 19          0074         LNK
      002B 845F   008B 0075         BZ    BT2
      002D 71          0076         LIS   1
      002E FC          0077         NS    S
      002F 8427   0057 0078         BZ    BT3
                       0079  *
      0031 69          0080         LISL  1        ADD SCALE TO RESULT.
      0032 2066        0081         LI    H'66'
      0034 CD          0082         AS    I
      0035 D6          0083         ASD   6
      0036 56          0084         LR    6,A
                       0085  *
      0037 45          0086         LR    A,5
      0038 19          0087         LNK
      0039 55          0088         LR    5,A
      003A 2066        0089         LI    H'66'
      003C CD          0090         AS    I
      003D D5          0091         ASD   5
      003E 55          0092         LR    5,A
                       0093  *
      003F 44          0094         LR    A,4
      0040 19          0095         LNK
      0041 54          0096         LR    4,A
      0042 2066        0097         LI    H'66'
      0044 CD          0098         AS    I
      0045 D4          0099         ASD   4
      0046 54          0100         LR    4,A
                       0101  *
      0047 43          0102         LR    A,3
      0048 19          0103         LNK
      0049 53          0104         LR    3,A
      004A 2066        0105         LI    H'66'
      004C CD          0106         AS    I
      004D D3          0107         ASD   3
      004E 53          0108         LR    3,A
                       0109  *
      004F 42          0110         LR    A,2
      0050 19          0111         LNK
      0051 52          0112         LR    2,A
      0052 2066        0113         LI    H'66'
      0054 CC          0114         AS    S
      0055 D2          0115         ASD   2
```

```
EMME SMT  FILE 4  REV 13 APR 82 JAK/DICKEY-JOHN
ERRS  LOC OBJECT ADDR LINE          SOURCE STATEMENT

      0056 52           0116         LR    2,A
                        0117  *
      0057 69           0118  BT3    LISL  1        MULTIPLY ADDER BY 2 DECIMALLY.
      0058 2066         0119         LI    H'66'
      005A CC           0120         AS    S
      005B DC           0121         ASD   S
      005C 5D           0122         LR    I,A
                        0123  *
      005D 4C           0124         LR    A,S
      005E 19           0125         LNK
      005F 50           0126         LR    0,A
      0060 2066         0127         LI    H'66'
      0062 CC           0128         AS    S
      0063 D0           0129         ASD   0
      0064 5D           0130         LR    I,A
                        0131  *
      0065 4C           0132         LR    A,S
      0066 19           0133         LNK
      0067 50           0134         LR    0,A
      0068 2066         0135         LI    H'66'
      006A CC           0136         AS    S
      006B D0           0137         ASD   0
      006C 5D           0138         LR    I,A
                        0139  *
      006D 4C           0140         LR    A,S
      006E 19           0141         LNK
      006F 50           0142         LR    0,A
      0070 2066         0143         LI    H'66'
      0072 CC           0144         AS    S
      0073 D0           0145         ASD   0
      0074 5D           0146         LR    I,A
                        0147  *
      0075 4C           0148         LR    A,S
      0076 19           0149         LNK
      0077 50           0150         LR    0,A
      0078 2066         0151         LI    H'66'
      007A CC           0152         AS    S
      007B D0           0153         ASD   0
      007C 5D           0154         LR    I,A
                        0155  *
      007D 4C           0156         LR    A,S      16 BIT RIGHT SHIFT.
      007E 12           0157         SR    1
      007F 5D           0158         LR    I,A
      0080 4E           0159         LR    A,D
      0081 15           0160         SL    4
      0082 12           0161         SR    1
      0083 15           0162         SL    4
      0084 EC           0163         XS    S
      0085 5D           0164         LR    I,A
      0086 4C           0165         LR    A,S
      0087 12           0166         SR    1
      0088 5C           0167         LR    S,A
      0089 909D    0027 0168         BR    BT1
      008B 1C           0169  BT2    POP
                        0170  *
```

```
FMME SMT  FILE 4  REV 13 APR 82 JAK/DICKEY-JOHN
ERRS  LOC OBJECT ADDR LINE          SOURCE STATEMENT

                      0171  *  TABLE: 2 CONVERSION CONSTANTS FOR BTOD
                      0172  *
      008C 000001     0173  DK       DC     H'0000010000'
      0091 000000     0174           DC     H'0000001526'
      0096 000010     0175           DC     H'0000100000'
                      0176  *
                      0177  *
                      0178  ***************************************************************
                      0179  *
                      0180  *  PHASE DETECTOR FREQUENCY READING ROUTINE - 1 SEC COLLECTION TIME.
                      0181  *
                      0182  ***************************************************************
                      0183  *
                      0184  *
      009B 08         0185  PHID     LR     K,P
      009C 2032       0186           LI     50       LOAD COUNTERS TO EQUAL 1 SECOND.
      009E 50         0187           LR     0,A
      009F 2043       0188           LI     67
      00A1 51         0189           LR     1,A
      00A2 66         0190           LISU   6
      00A3 69         0191           LISL   1
      00A4 A7         0192           INS    7        INIT LAST STATE.
      00A5 5E         0193           LR     D,A
      00A6 280167 0167 0194          PI     ACCUM    GOTO ACCUMULATE COUNTS.
      00A9 30         0195           DS     0
      00AA 94FB   00A6 0196          BNZ    *-4
      00AC 31         0197           DS     1
      00AD 94F8   00A6 0198          BNZ    *-7
                      0199  *
      00AF 4A         0200           LR     A,10
      00B0 2280       0201           OI     H'80'    SET PHID FLAG.
      00B2 5A         0202           LR     10,A     (INDICATES DATA HAS BEEN COLLECTED).
                      0203  *
      00B3 0C         0204           PK
                      0205  *
                      0206  *
                      0207  ***************************************************************
                      0208  *
                      0209  *  CELL STATUS VERIFICATION AND ERROR ROUTINE.
                      0210  *
                      0211  ***************************************************************
                      0212  *
      00B4 08         0213  TCELL    LR     K,P
      00B5 47         0214           LR     A,7
      00B6 2204       0215           OI     4
      00B8 57         0216           LR     7,A
      00B9 2010       0217           LI     H'10'
      00BB B1         0218           OUTS   1
      00BC 2801F0 01F0 0219          PI     TD5      DELAY .5 SECONDS.
      00BF 9006   00C6 0220          BR     CSKIP
                      0221  *
      00C1 08         0222  CELL     LR     K,P
      00C2 20FB       0223           LI     H'FB'
      00C4 F7         0224           NS     7
      00C5 57         0225           LR     7,A
                      0226  *
      00C6 00         0227  CSKIP    LR     A,KU
      00C7 06         0228           LR     QU,A
```

```
EMME SMT  FILE 4  REV 1  APR 82 JAK/DICKEY-JOHN
ERRS  LOC OBJECT ADDR LINE           SOURCE STATEMENT

      00C8 01            0229          LR    A,KL
      00C9 07            0230          LR    QL,A
                         0231  *
      00CA 0A            0232          LR    A,IS       SAVE ADDRESS FOR PHID OUTPUT.
      00CB 59            0233          LR    9,A
      00CC 4A            0234          LR    A,10
      00CD 13            0235          SL    1
      00CE 12            0236          SR    1
      00CF 5A            0237          LR    10,A       CLR PHID FLAG.
      00D0 71            0238  CELL1   LIS   1
      00D1 50            0239          LR    0,A        CLR ALL ERRORS SET BY THIS ROUTINE.
      00D2 2801C7 01C7   0240          PI    ERCLR
      00D5 72            0241          LIS   2
      00D6 50            0242          LR    0,A
      00D7 2801C7 01C7   0243          PI    ERCLR
      00DA 73            0244          LIS   3
      00DB 50            0245          LR    0,A
      00DC 2801C7 01C7   0246          PI    ERCLR
      00DF A0            0247  CELL3   INS   0          INPUT TOP SENSOR STATUS.
      00E0 2180          0248          NI    H'80'
      00E2 50            0249          LR    0,A
      00E3 280199 0199   0250          PI    BPOS       INPUT BOTTOM SENSOR STATUS.
      00E6 20C0          0251          LI    H'C0'
      00E8 F8            0252          NS    8
      00E9 E0            0253          XS    0
      00EA 942D   0118   0254          BNZ   CEL1       BR IF CELL  STATUS CONDITIONS NOT MET.
                         0255  *
      00EC 70            0256          CLR
      00ED CA            0257          AS    10
      00EE 911C   010B   0258          BM    CELL5      BR IF DATA ALREADY COLLECTED.
      00F0 280000 0000   0259          PI    EVCLR
      00F3 70            0260          CLR
      00F4 C9            0261          AS    9
      00F5 9402   00F8   0262          BNZ   CELL4      BR TO COLLECT DATA.
      00F7 0D            0263          LR    P0,Q       RETURN IF JUST CHECKING CELL STATUS.
                         0264  *
                         0265  *
      00F8 74            0266  CELL4   LIS   4
      00F9 F7            0267          NS    7
      00FA 840B   0106   0268          BZ    CELL6      BR IF NOT COLLECTING TEMPERATURE DATA.
      00FC 7F            0269          LIS   15
      00FD F8            0270          NS    8
      00FE 9407   0106   0271          BNZ   CELL6      BR IF FTU MODE NOT TEMPERATURE.
      0100 280000 0000   0272          PI    SCLR       ELSE BLANK FTU DISPLAY DURING COUNTING.
      0103 280000 0000   0273          PI    DSP
      0106 28009B 009B   0274  CELL6   PI    PHID       COLLECT DATA.
      0109 90D5   00DF   0275          BR    CELL3
                         0276  *
                         0277  *
      010B 66            0278  CELL5   LISU  6          MOVE DATA TO RETURN ADDRESS.
      010C 6A            0279          LISL  2
      010D 4D            0280          LR    A,I
      010E 50            0281          LR    0,A
      010F 4C            0282          LR    A,S
      0110 51            0283          LR    1,A
      0111 49            0284          LR    A,9
      0112 0B            0285          LR    IS,A
      0113 40            0286          LR    A,0
```

```
EMME SMT  FILE 4  REV 13 APR 82 JAK/DICKEY-JOHN
ERRS  LOC OBJECT ADDR LINE          SOURCE STATEMENT

       0114 50           0287          LR    I,A
       0115 41           0288          LR    A,I
       0116 5C           0289          LR    S,A
       0117 0D           0290          LR    P0,Q
                         0291  *
       0118 20C0         0292  CEL1    LI    H'C0'
       011A F8           0293          NS    8
       011B 8429   0145  0294          BZ    CEL2      BR IF CELL SHOULD BE FULL.
                         0295  *  CELL SHOULD BE EMPTY ---------------------------------------
       011D 70           0296          CLR
       011E C0           0297          AS    0
       011F 8111   0131  0298          BP    CEL3      BR IF TOP = IN.
                         0299  *
       0121 2003         0300  CEL6    LI    3         (ERROR # 3, INVALID SENSOR STATUS).
       0123 50           0301          LR    0,A
       0124 280175 0175  0302          PI    ERROR
                         0303  *
       0127 78           0304  CEL10   LIS   8
       0128 F7           0305          NS    7
       0129 9404   012E  0306          BNZ   CEL11     BR IF WARMING UP.
       012B 290000 0000  0307          JMP   EMPTY
                         0308  *
       012E 290000 0000  0309  CEL11   JMP   WRMUP
                         0310  *
       0131 2010         0311  CEL3    LI    H'10'
       0133 F8           0312          NS    8
       0134 8408   013D  0313          BZ    CEL4      BR IF EMPTY NOT DONE.
       0136 20DF         0314  CEL13   LI    H'DF'
       0138 F8           0315          NS    8
       0139 58           0316          LR    8,A       CLEAR SAMPLE DONE FLAG.
       013A 290000 0000  0317          JMP   SAMPLE
                         0318  *
       013D 2002         0319  CEL4    LI    2         (ERROR # 2 SAMPLE INSERTED PREMATURELY).
       013F 50           0320          LR    0,A       (OR TOO MUCH TIME REMOVING SAMPLE).
       0140 280175 0175  0321          PI    ERROR
       0143 90E3   0127  0322          BR    CEL10
                         0323  *
                         0324  *
                         0325  *  CELL SHOULD BE FULL ----------------------------------------
       0145 70           0326  CEL2    CLR
       0146 C0           0327          AS    0
       0147 9119   0161  0328          BM    CEL5      BR IF TOP = OUT.
       0149 2020         0329          LI    H'20'
       014B F8           0330          NS    8
       014C 8404   0151  0331          BZ    CEL7      BR IF SAMPLE NOT DONE.
       014E 290000 0000  0332          JMP   PREM
                         0333  *
       0151 71           0334  CEL7    LIS   1         (ERROR # 1, BOT=OUT,TOP=IN)
       0152 50           0335          LR    0,A       SAMPLE REMOVED PREMATURELY, RECALIBRATE.
       0153 280175 0175  0336          PI    ERROR
       0156 20EF         0337          LI    H'EF'
       0158 F8           0338          NS    8
       0159 58           0339          LR    8,A       CLR EMPTY DONE FLAG.
       015A 78           0340          LIS   8
       015B F7           0341          NS    7
       015C 94D1   012E  0342          BNZ   CEL11     BR IF WARMING UP.
       015E 290000 0000  0343          JMP   PREM
                         0344  *
```

```
EMME SMT  FILE 4  REV 13 APR 82 JAK/DUFFEY JOHN
ERRS  LOC OBJECT ADDR LINE          SOURCE STATEMENT

      0161 13                CEL5     SL     1
      0162 81BE   0121                BP     CEL6      BR IF BOTTOM = IN.
      0164 290000 0000                JMP    PREM
                             *
                             *
                             ################################################################
                             *
                             *  ACCUMULATING SUBROUTINE - EVENTS COUNTER.
                             *
                             ################################################################
                             *
      0167 A7                ACCUM    INS    7         INPUT NEW COUNTS
      0168 5D                         LR     I,A        AND SAVE.
      0169 18                         COM
      016A 1F                         INC
      016B CD                         AS     I         SUBTRACT FROM OLD.
      016C CC                         AS     S
      016D 5D                         LR     I,A       SUM DIFFERENCE TO ACCUMULATORS.
      016E 4C                         LR     A,S
      016F 19                         LNK
      0170 5C                         LR     S,A
      0171 68                         LISL   0
      0172 4D                         LR     A,I       PUT NEW COUNTS IN OLD COUNTS REG.
      0173 5E                         LR     D,A
      0174 1C                         POP
                             *
                             *
                             ################################################################
                             *
                             *  ERROR PRIORITIZING
                             *
                             ################################################################
                             *
                             *  ERROR 01    SAMPLE REMOVED TOO SOON
                             *  ERROR 02    SAMPLE INSERTED TOO SOON
                             *  ERROR 03    INVALID SENSOR STATUS
                             *  ERROR 04    EC DATA OUT OF RANGE
                             *  ERROR 05    TEMPERATURE TOO LOW
                             *  ERROR 06    DELTR DRIFT EXCESSIVE.
                             *  ERROR 07    K CKSM FAIL.
                             *
                             *
      0175 65                ERROR    LISU   5
      0176 6B                         LISL   3
      0177 2A0189 0189                DCI    ERRS
      017A 40                         LR     A,0       USE ERROR NUMBER TO POINT TO ERR TABLE.
      017B 13                         SL     1
      017C 8E                         ADC
      017D 7C                         LIS    H'C'
      017E F7                         NS     7
      017F 8B                         OM
      0180 57                         LR     7,A       SET APPROPRIATE FLAGS.
      0181 4C                         LR     A,S
      0182 8B                         OM
      0183 5C                         LR     S,A       SET ERROR FLAG IN R53.
      0184 20CF              ER2      LI     H'CF'     CLR SAMPLE DONE AND EMPTY DONE FLAG.
      0186 F8                         NS     8
```

```
ERRS LOC OBJECT ADDR LINE        SOURCE STATEMENT

     0187 58          0402           LR    8,A
     0188 1C          0403           POP
                      0404   *
     0189 007090      0405  ERRS     DC    H'00709001900280004'
     0191 8008C0      0406           DC    H'8008C01090208040'
                      0407   *       2 BYTES PER ERROR - FIRST BYTE CONTAINS MESSAGE FLAGS
                      0408   *       TO BE SET, SECOND BYTE CONTAINS ERROR FLAG TO BE SET
                      0409   *       IN THE ERROR REGISTER R53.
                      0410   *
                      0411   *
                      0412   ***********************************************************
                      0413   *
                      0414   *  BOTTOM POSITION SENSE -- READS TEMP CIRCUIT FOR 500
                      0415   *       MICROSECONDS TO DETECT CELL STATUS.
                      0416   *
                      0417   ***********************************************************
                      0418   *
     0199 08          0419  BPOS     LR    K,P
     019A A1          0420           INS   1
     019B 2151        0421           NI    H'51'
     019D 52          0422           LR    2,A     SAVE PHID SIGNAL SELECT.
     019E 12          0423           SR    1
     019F 13          0424           SL    1
     01A0 B1          0425           OUTS  1       ENABLE TEMP CIRCUIT.
     01A1 2801E0 01E0 0426           PI    TD10MS  DELAY 10 MILLISECONDS.
     01A4 2801E0 01E0 0427           PI    TD10MS  DELAY 10 MILLISECONDS.
     01A7 70          0428           CLR
     01A8 6B          0429           LISL  3
     01A9 5E          0430           LR    D,A     CLR EVENT COUNTER FOR BOT SENSOR.
     01AA 8FFE  01A9  0431           BR7   *-1
     01AC 2060        0432           LI    H'60'   LOAD TIMING COUNTER.
     01AE 51          0433           LR    1,A
     01AF 69          0434           LISL  1
     01B0 A7          0435           INS   7
     01B1 5E          0436           LR    D,A     INIT LAST STATE.
     01B2 280167 0167 0437  BPOS1    PI    ACCUM   GOTO ACCUMULATE COUNTS.
     01B5 31          0438           DS    1
     01B6 94FB  01B2  0439           BNZ   BPOS1   BR IF STILL COUNTING.
     01B8 6A          0440           LISL  2
     01B9 4D          0441           LR    A,I
     01BA CC          0442           AS    S
     01BB 19          0443           LNK
     01BC 2502        0444           CI    2
     01BE 9105  01C4  0445           BM    BPOS2   BR IF COUNTS > 2 ARE PRESENT.
     01C0 40          0446           LR    A,0     ELSE,
     01C1 2240        0447           OI    H'40'   SET EMPTY CELL FLAG FOR BOTTOM POSITION.
     01C3 50          0448           LR    0,A
     01C4 42          0449  BPOS2    LR    A,2
     01C5 B1          0450           OUTS  1       RESTORE PHID SIGNAL SELECT.
     01C6 0C          0451           PK
                      0452   *
                      0453   *
                      0454   ***********************************************************
                      0455   *
                      0456   *  CLEAR MATCHING ERRORS
                      0457   *
                      0458   ***********************************************************
                      0459   *
```

```
EMME SMT  FILE 4  REV 13 APR 82 JAK/DIFFEY [illegible]
ERRS  LOC OBJECT ADDR LINE          SOURCE STATEMENT

                      0460  *
  01C7 65             0461  ERCLR   LISU  5
  01C8 6B             0462          LISL  3
  01C9 2A0189 0189    0463          DCI   ERRS
  01CC 40             0464          LR    A,0     USE ERROR # FOR ERRS TABLE POINTER.
  01CD 13             0465          SL    1
  01CE 250A           0466          CI    10
  01D0 9402    01D3   0467          BNZ   ERC2
  01D2 70             0468          CLR
  01D3 8E             0469  ERC2    ADC
  01D4 16             0470          LM            IGNORE FIRST BYTE.
  01D5 16             0471          LM            LOAD ERROR FLAG TO BE DELETED FROM R53.
  01D6 18             0472          COM
  01D7 FC             0473          NS    S
  01D8 5C             0474          LR    S,A     DELETE ONLY THE ERROR SENT.
  01D9 9405    01DF   0475          BNZ   ERC1    BR IF THERE IS STILL AN ERROR SET.
  01DB 206F           0476          LI    H'6F'
  01DD F7             0477          NS    7
  01DE 57             0478          LR    7,A     ELSE, DELETE THE ERROR FLAG FROM R7.
  01DF 1C             0479  ERC1    POP
                      0480  *
                      0481  *
                      0482  **************************************************************
                      0483  *
                      0484  * 10 MILLISECOND DELAY      USES 70,71
                      0485  *
                      0486  **************************************************************
                      0487  *
  01E0 67             0488  TD10MS  LISU  7
  01E1 68             0489          LISL  0
  01E2 70             0490          CLR
  01E3 5D             0491          LR    I,A
  01E4 2004           0492          LI    4
  01E6 5E             0493          LR    D,A
  01E7 68             0494          LISL  0
  01E8 3C             0495          DS    S
  01E9 94FE    01E8   0496          BNZ   *-1
  01EB 69             0497          LISL  1
  01EC 3C             0498          DS    S
  01ED 94F9    01E7   0499          BNZ   *-6
  01EF 1C             0500          POP
                      0501  *
                      0502  *
                      0503  **************************************************************
                      0504  *
                      0505  * HALF SECOND DELAY      USES 2,3,4
                      0506  *
                      0507  **************************************************************
                      0508  *
                      0509  *
  01F0 71             0510  TD5     LIS   1
  01F1 52             0511          LR    2,A
  01F2 70             0512          CLR
  01F3 53             0513          LR    3,A
  01F4 54             0514          LR    4,A
  01F5 34             0515          DS    4
  01F6 94FE    01F5   0516          BNZ   *-1
```

```
EMME SMT  FILE 5  REV 17 MAR 82  JAK/DICKEY JOHN
ERRS  LOC OBJECT ADDR LINE          SOURCE STATEMENT

     01F8 33           0517           DS    3
     01F9 94FB    01F5 0518           BNZ   *-4
     01FB 32           0519           DS    2
     01FC 94F8    01F5 0520           BNZ   *-7
     01FE 1C           0521           POP
                       0522 *
                       0523 *
                       0524 *************************************************************
                       0525 *
                       0526 *  1 SECOND DELAY    USES 0,1,2
                       0527 *
                       0528 *************************************************************
                       0529 *
     01FF 72           0530 TD1S      LIS   2
     0200 50           0531           LR    0,A
     0201 20C2         0532           LI    194
     0203 51           0533           LR    1,A
     0204 70           0534           CLR
     0205 52           0535           LR    2,A
     0206 32           0536           DS    2
     0207 94FE    0206 0537           BNZ   *-1
     0209 31           0538           DS    1
     020A 94FB    0206 0539           BNZ   *-4
     020C 30           0540           DS    0
     020D 94F8    0206 0541           BNZ   *-7
     020F 1C           0542           POP
                       0543 *
                       0544           END
00 ERRS
                       0001 * EMM5
                       0002 *5555555555555555555555555555555555555555555555555555555555555555
                       0003 *
                       0004           TITLE 'EMME SMT  FILE 5  REV 17 MAR 82  JAK/DICKEY-JOHN'
                       0005 *         A
                       0006 *
                       0007 *
                       0008 *
                       0009 *
                       0010 *
                  0000 0011 ORGIN     RORG  0
                       0012           ENTRY BSUB,DIVBIN,MULBIN,NRMLZ,SHRES,BSUB3,LOG
                       0013           ENTRY SUBEXP,ADDEXP,NRM14
                       0014 *
                       0015 *
                       0016 *
                       0017 *
                       0018 *************************************************************
                       0019 *
                       0020 *  R0 = ISAR AT LSB SUBTRAHEND.
                       0021 *  R1 = ISAR AT LSB DIFFERENCE.
                       0022 *  ISAR AT LSB OF MINUEND.
                       0023 *   USES R0,1,2,3,4,5
                       0024 *
                       0025 *************************************************************
                       0026 *
     0000 4D           0027 BSUB      LR    A,I
```

```
EMME SMT FILE 5 REV 17 MAR [illegible] JAK/DUFFEY-JOHN
ERRS LOC OBJECT ADDR LINE          SOURCE STATEMENT

     0001 52          0028         LR    2,A
     0002 4C          0029         LR    A,S
     0003 53          0030         LR    3,A
     0004 40          0031         LR    A,0
     0005 0B          0032         LR    IS,A
     0006 4D          0033         LR    A,I
     0007 18          0034         COM
     0008 54          0035         LR    4,A
     0009 4C          0036         LR    A,S
     000A 18          0037         COM
     000B 55          0038         LR    5,A
                      0039  *
     000C 71          0040         LIS   1
     000D C4          0041         AS    4
     000E 54          0042         LR    4,A
     000F 45          0043         LR    A,5
     0010 19          0044         LNK
     0011 55          0045         LR    5,A
     0012 44          0046         LR    A,4
     0013 C2          0047         AS    2
     0014 52          0048         LR    2,A
     0015 43          0049         LR    A,3
     0016 19          0050         LNK
     0017 C5          0051         AS    5
     0018 53          0052         LR    3,A
     0019 41          0053         LR    A,1
     001A 0B          0054         LR    IS,A
     001B 42          0055         LR    A,2
     001C 5D          0056         LR    I,A
     001D 43          0057         LR    A,3
     001E 5C          0058         LR    S,A
     001F 8112   0032 0059         BP    BSUB1
     0021 4E          0060         LR    A,D         JUST TO DEC ISAR.
                      0061  *
     0022 4C          0062  BSUB3  LR    A,S
     0023 18          0063         COM
     0024 1F          0064         INC
     0025 5D          0065         LR    I,A
     0026 4C          0066         LR    A,S
     0027 1E          0067         LR    J,W
     0028 18          0068         COM
     0029 1D          0069         LR    W,J
     002A 19          0070         LNK
     002B 5C          0071         LR    S,A
     002C 4A          0072         LR    A,10
     002D 2280        0073         OI    H'80'
     002F 5A          0074         LR    10,A        SET NEG FLAG.
     0030 9005   0036 0075         BR    BSUB2
                      0076  *
     0032 207F        0077  BSUB1  LI    H'7F'
     0034 FA          0078         NS    10
     0035 5A          0079         LR    10,A        CLR NEG FLAG.
                      0080  *
     0036 1C          0081  BSUB2  POP
                      0082  *
                      0083  *
                      0084  ***********************************************************
                      0085  *
```

```
EMMF SMT FILE 5 REV 17 MAR 82 JAK/DICKEY JOHN
ERRS LOC OBJECT ADDR LINE          SOURCE STATEMENT

                     0086 *
                     0087 * LOG ROUTINE
                     0088 *
                     0089 * LOG OF 16-BIT BINARY NUMBER IN R 0 (MSB) AND R 1 (LSB).
                     0090 * RESULT RETURNED IN R 64-66.  (LSB-MSB)
                     0091 * INPUT RANGE: FROM 0100 TO FEFF
                     0092 *
                     0093 * USES R 0-6, 64-67.
                     0094 *
                     0095 *
                     0096 * ALGORITHM FROM KNUTH, VOL. 1, P. 26, EX. 25
                     0097 *
                     0098 *   0,1 Z
                     0099 *   2,3 X
                     0100 *   4,5 T
                     0101 *   5   N
                     0102 *   6   K
                     0103 * 64-67 Y
                     0104 *
                     0105 *
0037 08              0106 LOG    LR    K,P
0038 70              0107        CLR
0039 55              0108        LR    5,A
003A 40              0109        LR    A,0
003B C1              0110        AS    1
003C 19              0111        LNK
003D 8479      00B7  0112        BZ    ALDONE
003F 45              0113 RESH   LR    A,5
0040 1F              0114        INC
0041 55              0115        LR    5,A      N = N+1
0042 41              0116        LR    A,1
0043 C1              0117        AS    1
0044 51              0118        LR    1,A      SHIFT NUMBER LEFT UNTIL A 1 COMES OUT.
0045 40              0119        LR    A,0
0046 19              0120        LNK
0047 1E              0121        LR    J,W
0048 C0              0122        AS    0
0049 50              0123        LR    0,A
004A 8204      004F  0124        BC    FND      CARRY MEANS 1 OUT.
004C 1D              0125        LR    W,J      RESTORE EARLIER CARRY.
004D 92F1      003F  0126        BNC   RESH     IF NONE, RESHIFT.
004F 66              0127 FND    LISU  6        PUT N IN R 64-67.
0050 6C              0128        LISL  4
0051 70              0129        CLR            CLR RESULT REGISTERS.
0052 5D              0130        LR    I,A
0053 5D              0131        LR    I,A
0054 45              0132        LR    A,5
0055 15              0133        SL    4        PUT IN MSD.
0056 5D              0134        LR    I,A
0057 41              0135        LR    A,1
0058 53              0136        LR    3,A
0059 40              0137        LR    A,0
005A 52              0138        LR    2,A
005B 71              0139        LIS   1
005C 56              0140        LR    6,A      K = 1
005D 2800BE    00BE  0141        PI    SHRZ     Z = X/2
0060 2080            0142        LI    H'80'
```

```
EMME SMT  FILE 5  REV 17 MAR 82  JAK/DICKEY JOHN
ERRS  LOC OBJECT ADDR LINE          SOURCE STATEMENT

      0062 E0           0143        XS    0        X WAS GREATER THAN 1
      0063 50           0144        LR    0,A      SO SET MSB OF Z
      0064 70           0145  AGN   CLR            CHECK FOR X = 0.
      0065 C2           0146        AS    2
      0066 9404    006B 0147        BNZ   XNEO
      0068 C3           0148        AS    3
      0069 8453    00BD 0149        BZ    DONE
      006B 41           0150  XNEO  LR    A,I
      006C 18           0151        COM
      006D 1F           0152        INC
      006E 1E           0153        LR    J,W
      006F C3           0154        AS    3        BINARY SUBTRACT, 16-BIT.
      0070 55           0155        LR    5,A
      0071 9202    0074 0156        BNC   NOC
      0073 1E           0157        LR    J,W
      0074 40           0158  NOC   LR    A,0
      0075 18           0159        COM
      0076 1D           0160        LR    W,J
      0077 19           0161        LNK
      0078 1E           0162        LR    J,W
      0079 C2           0163        AS    2
      007A 54           0164        LR    4,A
      007B 820C    0088 0165        BC    TGE1
      007D 1D           0166        LR    W,J
      007E 8209    0088 0167        BC    TGE1     IS T >= 1 ??
      0080 2800BE  00BE 0168        PI    SHRZ     NO, Z <= Z/2
      0083 46           0169        LR    A,6
      0084 1F           0170        INC
      0085 56           0171        LR    6,A      AND INC K.
      0086 90DD    0064 0172        BR    AGN      RETURN AND REPEAT.
      0088 44           0173  TGE1  LR    A,4      T >= 1; Z<= X <= T
      0089 50           0174        LR    0,A
      008A 52           0175        LR    2,A
      008B 45           0176        LR    A,5
      008C 51           0177        LR    1,A
      008D 53           0178        LR    3,A
      008E 2800BE  00BE 0179        PI    SHRZ     Z <= X/2
      0091 2080         0180        LI    H'80'
      0093 E0           0181        XS    0        X > 1, SO SET MSB OF Z.
      0094 50           0182        LR    0,A
      0095 46           0183        LR    A,6      SHIFT Z (K-1) MORE TIMES.
      0096 55           0184        LR    5,A
      0097 35           0185  DZAG  DS    5
      0098 8406    009F 0186        BZ    NOMS
      009A 2800BE  00BE 0187        PI    SHRZ
      009D 90F9    0097 0188        BR    DZAG
      009F 2A00CB  00CB 0189  NOMS  DCI   LOGTB    3 BYTES PER VALUE.
      00A2 46           0190        LR    A,6      (K-1)*3
      00A3 24FF         0191        AI    H'FF'    DECREMENT.
      00A5 55           0192        LR    5,A
      00A6 C5           0193        AS    5
      00A7 C5           0194        AS    5        ACC IS (K-1) * 3.
      00A8 8E           0195        ADC            INDEX TO LOOKUP TABLE VAL.
      00A9 6C           0196        LISL  4        ADD @DC TO @ISAR.
      00AA 12           0197        SR    1        (THIS JUST TO CLR CARRY).
      00AB 16           0198  LOOP  LM
      00AC 19           0199        LNK
```

```
EMME SMT FILE 5 REV 17 MAR 82 JAK/DICKEY JOHN
ERRS LOC OBJECT ADDR LINE         SOURCE STATEMENT

     00AD 1E            0200          LR    J,W
     00AE CC            0201          AS    S
     00AF 5D            0202          LR    I,A
     00B0 8202    00B3  0203          BC    L1
     00B2 1D            0204          LR    W,J
     00B3 8FF7    00AB  0205 L1       BR7   LOOP
     00B5 90AE    0064  0206          BR    AGN       REPEAT PROCESS TILL X = 0.
                        0207 *
     00B7 66            0208 ALDONE   LISU  6
     00B8 6C            0209          LISL  4
     00B9 70            0210          CLR
     00BA 5D            0211          LR    I,A
     00BB 5D            0212          LR    I,A
     00BC 5C            0213          LR    S,A       CLR RESULT REGS IF ENTRY WAS 0.
     00BD 0C            0214 DONE     PK
                        0215 *
                        0216 *
                        0217 * SHIFT 0,1 RIGHT ONE BIT
                        0218 *
     00BE 41            0219 SHRZ     LR    A,1
     00BF 12            0220          SR    1
     00C0 51            0221          LR    1,A
     00C1 40            0222          LR    A,0
     00C2 15            0223          SL    4
     00C3 12            0224          SR    1
     00C4 15            0225          SL    4
     00C5 E1            0226          XS    1
     00C6 51            0227          LR    1,A
     00C7 40            0228          LR    A,0
     00C8 12            0229          SR    1
     00C9 50            0230          LR    0,A
     00CA 1C            0231          POP
                        0232 *
                        0233 *
                        0234 ***********************************************************
                        0235 *
                        0236 * TABLE OF COMPLEMENTED LOOKUP VALUES
                        0237 *  LOG2(2**K/(2**K-1)
                        0238 *
                        0239 ***********************************************************
                        0240 *
     00CB 00000F        0241 LOGTB    DC    H'00000F' (REVERSE ORDER OF BYTES)
     00CE 025CF9        0242          DC    H'025CF9'
     00D1 EDEAFC        0243          DC    H'EDEAFC'
     00D4 A082FE        0244          DC    H'A082FE'
     00D7 6344FF        0245          DC    H'6344FF'
     00DA F0A2FF        0246          DC    H'F0A2FF'
     00DD A7D1FF        0247          DC    H'A7D1FF'
     00E0 DFE8FF        0248          DC    H'DFE8FF'
     00E3 72F4FF        0249          DC    H'72F4FF'
     00E6 3AFAFF        0250          DC    H'3AFAFF'
     00E9 1DFDFF        0251          DC    H'1DFDFF'
     00EC 8FFEFF        0252          DC    H'8FFEFF'
     00EF 47FFFF        0253          DC    H'47FFFF'
     00F2 A4FFFF        0254          DC    H'A4FFFF'
     00F5 D2FFFF        0255          DC    H'D2FFFF'
     00F8 E9FFFF        0256          DC    H'E9FFFF'
                        0257 *
```

EMME SMI FILE 5 REV 17 MAR 82 JAE/DUFFEY JOHN

```
ERRS LOC OBJECT ADDR LINE        SOURCE STATEMENT

                     0258 *
                     0259 *
                     0260 *
     00FB 2080       0261 NRMLZ  LI    H'80'   NORMALIZE OP AT IS, IS-1.
     00FD 53         0262 NRM3   LR    3,A
     00FE 70         0263        CLR
     00FF 52         0264        LR    2,A
     0100 CE         0265        AS    D
     0101 CD         0266        AS    I
     0102 19         0267        LNK
     0103 9403  0107 0268        BNZ   NRM1    CHECK FOR ZERO
     0105 4E         0269        LR    A,D     JUST TO DECREMENT ISAR.
     0106 1C         0270 NRM2   POP           LEAVES WITH ISAR AT IS-1.
     0107 43         0271 NRM1   LR    A,3
     0108 FE         0272        NS    D
     0109 94FC  0106 0273        BNZ   NRM2
     010B 4C         0274        LR    A,S     SHIFT IT
     010C CC         0275        AS    S
     010D 5D         0276        LR    I,A
     010E 4C         0277        LR    A,S
     010F 19         0278        LNK
     0110 CC         0279        AS    S
     0111 5C         0280        LR    S,A
     0112 42         0281        LR    A,2
     0113 1F         0282        INC
     0114 52         0283        LR    2,A     KEEP NUMBER OF SHIFTS
     0115 90F1  0107 0284        BR    NRM1
                     0285 *
     0117 20E0       0286 NRM14  LI    H'E0'   NORMALIZE TO 14 BITS
     0119 90E3  00FD 0287        BR    NRM3
                     0288 *
                     0289 *
                     0290 *
                     0291 *
     011B 66         0292 SHRES  LISU  6       SHIFT RESULT TILL 60 IS ZERO.
     011C 68         0293        LISL  0
     011D 70         0294        CLR
     011E CC         0295        AS    S
     011F 67         0296        LISU  7
     0120 9402  0123 0297        BNZ   SHR1
     0122 1C         0298 SHR4   POP           ZERO; RETURN
     0123 68         0299 SHR1   LISL  0
     0124 52         0300 SHR3   LR    2,A
     0125 8113  0139 0301        BP    SHR2
     0127 4C         0302        LR    A,S     LESS THAN ZERO; SHIFT RIGHT
     0128 12         0303        SR    1
     0129 5D         0304        LR    I,A
     012A 4E         0305        LR    A,D
     012B 15         0306        SL    4
     012C 12         0307        SR    1
     012D 15         0308        SL    4
     012E EC         0309        XS    S
     012F 5D         0310        LR    I,A
     0130 4C         0311        LR    A,S
     0131 12         0312        SR    1
     0132 5E         0313        LR    D,A
     0133 42         0314        LR    A,2
     0134 1F         0315        INC
```

```
EMME SMI  FILE 5  REV 17 MAR 82  JKW/DICKEY JOHN
ERRS LOC OBJECT ADDR LINE          SOURCE STATEMENT
     0135 84EC   0122 0316          BZ    SHR4
     0137 90EC   0124 0317          BR    SHR3
                      0318  *
     0139 4C          0319  SHR2    LR    A,S        >0; SHIFT LEFT
     013A CC          0320          AS    S
     013B 5D          0321          LR    I,A
     013C 4C          0322          LR    A,S
     013D 19          0323          LNK
     013E CC          0324          AS    S
     013F 5E          0325          LR    D,A
     0140 32          0326          DS    2
     0141 94F7   0139 0327          BNZ   SHR2
     0143 1C          0328          POP
                      0329  *
                      0330  *
                      0331  *
                      0332  *
     0144 42          0333  SUBEXP  LR    A,2        SUBTRACT R2 FROM 60.
     0145 18          0334          COM
     0146 1F          0335          INC
     0147 66          0336  SBX1    LISU  6
     0148 68          0337          LISL  0
     0149 CC          0338          AS    S
     014A 5C          0339          LR    S,A
     014B 1C          0340          POP
                      0341  *
     014C 42          0342  ADDEXP  LR    A,2        ADD R2 TO 60.
     014D 90F9   0147 0343          BR    SBX1
                      0344  *
                      0345  *
     014F 67          0346  MULBIN  LISU  7          16 X 16 BINARY MULTIPLY
     0150 6C          0347          LISL  4           16 BIT RESULT.
     0151 2080        0348          LI    H'80'      70,71 X 72,73 -> 75,76
     0153 5D          0349          LR    I,A        ROUND RESULT TO 16 BITS
     0154 70          0350          CLR
     0155 5D          0351          LR    I,A
     0156 5D          0352          LR    I,A
     0157 5C          0353          LR    S,A        CLEAR BOTTOM OF MPCAND
     0158 70          0354  MUL2    CLR
     0159 6A          0355          LISL  2
     015A CD          0356          AS    I
     015B CC          0357          AS    S          IS MPIER ZERO YET?
     015C 19          0358          LNK
     015D 8435   0193 0359          BZ    MUL3
     015F 72          0360          LIS   2
     0160 52          0361          LR    2,A        NO...
     0161 6F          0362          LISL  7
     0162 4C          0363  MUL1    LR    A,S        SHIFT MPCAND RIGHT
     0163 12          0364          SR    1
     0164 5D          0365          LR    I,A
     0165 4E          0366          LR    A,D
     0166 15          0367          SL    4
     0167 12          0368          SR    1
     0168 15          0369          SL    4
     0169 EC          0370          XS    S
     016A 5D          0371          LR    I,A
     016B 32          0372          DS    2
```

```
FMME SMT  FILE 5  REV 17 MAR 82  JAK/DICKEY JOHN
ERRS  LOC OBJECT ADDR LINE          SOURCE STATEMENT

      016C 94F5  0162 0373            BNZ   MUL1
      016E 4C         0374            LR    A,S
      016F 12         0375            SR    1
      0170 5C         0376            LR    S,A
      0171 6B         0377            LISL  3         LOOK AT MSBIT OF MPIER
      0172 70         0378            CLR
      0173 CC         0379            AS    S
      0174 8114  0189 0380            BP    MUL4
      0176 6F         0381            LISL  7         WAS 1; ADD MPCAND TO RESULT
      0177 4C         0382            LR    A,S
      0178 6C         0383            LISL  4
      0179 CC         0384            AS    S
      017A 5C         0385            LR    S,A
      017B 68         0386            LISL  0
      017C 4C         0387            LR    A,S
      017D 19         0388            LNK
      017E 8204  0183 0389            BC    MUL5      IF CARRY HERE, DON'T CHG
      0180 6D         0390            LISL  5          RESULT BYTE
      0181 CC         0391            AS    S
      0182 5C         0392            LR    S,A
      0183 69         0393 MUL5       LISL  1
      0184 4C         0394            LR    A,S
      0185 19         0395            LNK
      0186 6E         0396            LISL  6
      0187 CC         0397            AS    S
      0188 5C         0398            LR    S,A       HI BYTE OF RESULT
      0189 6A         0399 MUL4       LISL  2
      018A 4C         0400            LR    A,S       SHIFT MPIER LEFT
      018B CC         0401            AS    S
      018C 5D         0402            LR    I,A
      018D 4C         0403            LR    A,S
      018E 19         0404            LNK
      018F CC         0405            AS    S
      0190 5C         0406            LR    S,A
      0191 90C6  0158 0407            BR    MUL2      NEXT. . .
      0193 6D         0408 MUL3       LISL  5
      0194 4C         0409            LR    A,S
      0195 68         0410            LISL  0
      0196 5C         0411            LR    S,A
      0197 6E         0412            LISL  6
      0198 4C         0413            LR    A,S
      0199 69         0414            LISL  1
      019A 5D         0415            LR    I,A
      019B 1C         0416            POP
                      0417 *
                      0418 *  DIVIDE     70,71 / 72,73 = 75,76
                      0419 *
      019C 67         0420 DIVBIN     LISU  7         14 / /14 -> 12 BIT RESULT.
      019D 6D         0421            LISL  5
      019E 70         0422            CLR             CLEAR RESULT
      019F 5D         0423            LR    I,A
      01A0 5D         0424            LR    I,A
      01A1 6A         0425            LISL  2         IF /0 RESULT IS 0
      01A2 4D         0426            LR    A,I
      01A3 CC         0427            AS    S
      01A4 19         0428            LNK
      01A5 84ED  0193 0429            BZ    MUL3
      01A7 7E         0430            LIS   14
```

```
EMML SMT  FILE 6  REV 13 APR 82  JAK/DICKEY JOHN
ERRS  LOC OBJECT ADDR LINE          SOURCE STATEMENT

      01A8 52          0431         LR    2,A     R2 IS BIT COUNTER
      01A9 9011   01BB 0432         BR    DIV2    SKIP SHIFT FIRST TIME
      01AB 68          0433  DIV1   LISL  0
      01AC 4C          0434         LR    A,S
      01AD CC          0435         AS    S       SHIFT NUMERATOR LEFT
      01AE 5D          0436         LR    I,A
      01AF 4C          0437         LR    A,S
      01B0 19          0438         LNK
      01B1 CC          0439         AS    S
      01B2 5C          0440         LR    S,A
      01B3 6D          0441         LISL  5       SHIFT QUOTIENT LEFT
      01B4 4C          0442         LR    A,S
      01B5 CC          0443         AS    S
      01B6 5D          0444         LR    I,A
      01B7 4C          0445         LR    A,S
      01B8 19          0446         LNK
      01B9 CC          0447         AS    S
      01BA 5C          0448         LR    S,A
      01BB 6A          0449  DIV2   LISL  2       SUBTRACT DIVISOR
      01BC 4C          0450         LR    A,S      FROM NUMERATOR
      01BD 18          0451         COM
      01BE 1F          0452         INC
      01BF 1E          0453         LR    J,W
      01C0 68          0454         LISL  0
      01C1 CC          0455         AS    S
      01C2 53          0456         LR    3,A     LO BYTE OF RESULT
      01C3 9202   01C6 0457         BNC   DIV3
      01C5 1E          0458         LR    J,W
      01C6 6B          0459  DIV3   LISL  3
      01C7 4C          0460         LR    A,S
      01C8 18          0461         COM
      01C9 1D          0462         LR    W,J
      01CA 19          0463         LNK
      01CB 1E          0464         LR    J,W
      01CC 69          0465         LISL  1
      01CD CC          0466         AS    S
      01CE 8204   01D3 0467         BC    DIV4    HI BYTE OF RESULT IN ACC
      01D0 1D          0468         LR    W,J
      01D1 920B   01DD 0469         BNC   DIV5
      01D3 5E          0470  DIV4   LR    D,A     CARRY OUT! SAVE IT
      01D4 43          0471         LR    A,3
      01D5 5C          0472         LR    S,A
      01D6 71          0473         LIS   1       ADD 1 TO QUOTIENT
      01D7 6D          0474         LISL  5
      01D8 CC          0475         AS    S
      01D9 5D          0476         LR    I,A
      01DA 4C          0477         LR    A,S
      01DB 19          0478         LNK
      01DC 5C          0479         LR    S,A
      01DD 32          0480  DIV5   DS    2
      01DE 94CC   01AB 0481         BNZ   DIV1    BR IF BIT COUNTER NOT ZERO.
      01E0 90B2   0193 0482         BR    MUL3
                       0483  *
                       0484         END
00 ERRS
```

```
EMME SMT  FILE 6  REV 13 APR 82  JAK/DICKEY-JOHN
ERRS LOC OBJECT ADDR LINE         SOURCE STATEMENT
                    0001  * EMM6
                    0002  *6666666666666666666666666666666666666666666666666666666666666666
                    0003  *
                    0004          TITLE 'EMME SMT  FILE 6  REV 13 APR 82  JAK/DICKEY-JOHN'
                    0005  *       A
                    0006  *
                    0007  *
                    0008  *
                    0009  *
                    0010  *
          0000 0011 ORGIN  RORG  0
               0012        ENTRY MATH,TK5
               0013        EXTRN KFECH,BSUB,BSUB3,LOG,NRMLZ,SHRES,SUBEXP,ADDEXP
               0014        EXTRN MULBIN,DIVBIN,NRM14,ERROR,SAME
               0015  *
               0016  *
               0017  *****************************************************************
               0018  *
               0019  *      MULTIPLY TEMPERATURE DATA BY K5
               0020  *
               0021  *****************************************************************
               0022  *
               0023  *
0000 08        0024  TK5   LR    K,P
0001 66        0025        LISU  6
0002 68        0026        LISL  0
0003 73        0027        LIS   3         INIT EXPONENT            +16,MULT.
0004 5C        0028        LR    S,A                                +16,DPADJ.
0005 67        0029        LISU  7                                  -29,K5.
0006 69        0030        LISL  1
0007 280000 0000 0031      PI    NRMLZ     NORMALIZE TEMPERATURE COUNTS.
000A 280000 0000 0032      PI    SUBEXP
000D 75        0033        LIS   5
000E 50        0034        LR    0,A
000F 280000 0000 0035      PI    KFECH     LOAD K5.
0012 72        0036        LIS   2
0013 FB        0037        NS    11
0014 8406  001B 0038       BZ    TK52      BR IF NO CKSM ERROR.
0016 77        0039        LIS   7
0017 50        0040        LR    0,A       ELSE LOAD ERROR 7
0018 290000 0000 0041      JMP   SAME      AND RETURN ERROR LOOP.
               0042  *
001B 280000 0000 0043 TK52 PI    NRMLZ     NORMALIZE K5.
001E 280000 0000 0044      PI    SUBEXP
0021 280000 0000 0045      PI    MULBIN    MULTIPLY TEMPERATURE COUNTS BY K5.
0024 20B7      0046        LI    H'B7'     LOAD .0001 X 2**29.
0026 5D        0047        LR    I,A
0027 20D1      0048        LI    H'D1'
0029 5C        0049        LR    S,A
002A 280000 0000 0050      PI    MULBIN    MULTIPLY BY K5 CORRECTION FACTOR.
002D 280000 0000 0051      PI    SHRES
0030 4D        0052        LR    A,I
0031 50        0053        LR    0,A
0032 4C        0054        LR    A,S
0033 51        0055        LR    1,A
0034 63        0056        LISU  3
0035 6E        0057        LISL  6
```

```
EMME SMT  FILE 6  REV 13 APR 82  JAK/DILKEY-JOHN
ERRS  LOC OBJECT ADDR LINE          SOURCE STATEMENT

      0036 70          0058          CLR
      0037 CD          0059          AS    I
      0038 CE          0060          AS    D
      0039 19          0061          LNK
      003A 840A   0045 0062          BZ    TK51       BR IF FIRST TEMPERATURE.
      003C 65          0063          LISU  5
      003D 6D          0064          LISL  5
      003E 70          0065          CLR
      003F CE          0066          AS    D
      0040 CC          0067          AS    S
      0041 19          0068          LNK
      0042 8402   0045 0069          BZ    TK51       BR IF SECOND TEMPERATURE.
      0044 6E          0070          LISL  6          ELSE THIRD TEMPERATURE.
      0045 40          0071 TK51     LR    A,0
      0046 5D          0072          LR    I,A        SAVE TEMPERATURE.
      0047 41          0073          LR    A,1
      0048 5C          0074          LR    S,A
      0049 0C          0075          PK
                       0076 *
                       0077 *
                       0078 ***********************************************************
                       0079 *
                       0080 *  COMPUTE EMME #, % FAT, % LEAN, AND TEMPERATURE COMP
                       0081 *
                       0082 ***********************************************************
                       0083 *
                       0084 *
      004A 08          0085 MATH     LR    K,P
      004B 00          0086          LR    A,KU
      004C 06          0087          LR    QU,A
      004D 01          0088          LR    A,KL
      004E 07          0089          LR    QL,A
                       0090 *
      004F 66          0091          LISU  6          INIT EXPONENT = 9    +16,DPADJ.
      0050 68          0092          LISL  0                               -13,DIV.
      0051 79          0093          LIS   9                               +48,MULT.
      0052 5C          0094          LR    S,A                             -42,K6,K7.
                       0095 *
      0053 2026        0096          LI    0'46'
      0055 50          0097          LR    0,A
      0056 203A        0098          LI    0'72'
      0058 51          0099          LR    1,A
      0059 64          0100          LISU  4
      005A 6C          0101          LISL  4
                       0102 *
      005B 280000 0000 0103          PI    BSUB                            DR = D - R.
      005E 280000 0000 0104          PI    NRM14      DR IS DIVISOR.
      0061 280000 0000 0105          PI    ADDEXP
                       0106 *
      0064 2024        0107          LI    0'44'
      0066 50          0108          LR    0,A
      0067 2038        0109          LI    0'70'
      0069 51          0110          LR    1,A
      006A 64          0111          LISU  4
      006B 68          0112          LISL  0
                       0113 *
      006C 280000 0000 0114          PI    BSUB                            DS = DE - D.
```

```
EMME SMT  FILE 6  REV 13 APR 82  JAF/DICLEY JOHN
ERRS  LOC OBJECT ADDR LINE          SOURCE STATEMENT
      006F 280000 0000 0115         PI    NRM14      DS IS DIVIDEND.
      0072 280000 0000 0116         PI    SUBEXP
                       0117  *A-------------------------------------------------------
      0075 280000 0000 0118         PI    DIVBIN                         DS / DR.
                       0119  *--------------------------------------------------------
                       0120  *
      0078 20CC        0121         LI    H'CC'      LOAD .00000001 X 2**42.
      007A 5D          0122         LR    I,A
      007B 20AB        0123         LI    H'AB'
      007D 5C          0124         LR    S,A
                       0125  *
      007E 69          0126         LISL  1
      007F 280000 0000 0127         PI    NRMLZ
      0082 280000 0000 0128         PI    SUBEXP
                       0129  *B-------------------------------------------------------
      0085 280000 0000 0130         PI    MULBIN
                       0131  *--------------------------------------------------------
                       0132  *
      0088 76          0133         LIS   6
      0089 50          0134         LR    0,A
      008A 280000 0000 0135         PI    KFECH      LOAD K6.
      008D 72          0136         LIS   2
      008E FB          0137         NS    11
      008F 8404   0094 0138         BZ    M2
                       0139  *
      0091 77          0140  M3     LIS   7
      0092 50          0141         LR    0,A
      0093 0D          0142         LR    P0,Q
                       0143  *
      0094 280000 0000 0144  M2     PI    NRMLZ
      0097 280000 0000 0145         PI    SUBEXP
                       0146  *N-------------------------------------------------------
      009A 280000 0000 0147         PI    MULBIN
                       0148  *--------------------------------------------------------
                       0149  *
      009D 77          0150         LIS   7
      009E 50          0151         LR    0,A
      009F 280000 0000 0152         PI    KFECH      LOAD K7.
                       0153  *
      00A2 280000 0000 0154         PI    NRMLZ
      00A5 280000 0000 0155         PI    SUBEXP
                       0156  *O-------------------------------------------------------
      00A8 280000 0000 0157         PI    MULBIN
                       0158  *--------------------------------------------------------
      00AB 69          0159         LISL  1
      00AC 4E          0160         LR    A,D        MOVE: R70 -> R65    SAVE RESULT & EXP.
      00AD 50          0161         LR    0,A              R71 -> R66.
      00AE 4C          0162         LR    A,S
      00AF 66          0163         LISU  6
      00B0 6D          0164         LISL  5
      00B1 5D          0165         LR    I,A
      00B2 40          0166         LR    A,0
      00B3 5C          0167         LR    S,A
      00B4 68          0168         LISL  0
      00B5 4E          0169         LR    A,D              R60 -> R67.
      00B6 5C          0170         LR    S,A
                       0171  *
      00B7 280000 0000 0172         PI    SHRES
                       0173  *
```

```
EMME SMT FILE 2 REV
ERRS LOC OBJECT ADDR LINE          SOURCE STATEMENT
     00BA 4D            0174        LR    A,I        MOVE: R70 -> R50    STORE EMME #.
     00BB 50            0175        LR    0,A              R71 -> R51.
     00BC 4C            0176        LR    A,S
     00BD 65            0177        LISU  5
     00BE 69            0178        LISL  1
     00BF 5E            0179        LR    D,A
     00C0 40            0180        LR    A,0
     00C1 5C            0181        LR    S,A
                        0182  *
     00C2 66            0183        LISU  6          INITIALIZE EXPONENT = 14   +32,MULT.
     00C3 68            0184        LISL  0                                     -32,K4.
     00C4 7E            0185        LIS   14                                    +14,DPADJ.
     00C5 5C            0186        LR    S,A
                        0187  *
     00C6 67            0188        LISU  7
     00C7 68            0189        LISL  0
     00C8 2021          0190        LI    H'21'
     00CA 5D            0191        LR    I,A
     00CB 2013          0192        LI    H'13'
     00CD 5E            0193        LR    D,A
     00CE 0A            0194        LR    A,IS
     00CF 50            0195        LR    0,A
     00D0 51            0196        LR    1,A
     00D1 63            0197        LISU  3
     00D2 6E            0198        LISL  6
                        0199  *
     00D3 280000 0000   0200        PI    BSUB                          DT = T - 4897.
     00D6 280000 0000   0201        PI    NRMLZ      DT IS MULTIPLICAND.
     00D9 280000 0000   0202        PI    SUBEXP
                        0203  *
     00DC 74            0204        LIS   4
     00DD 50            0205        LR    0,A
     00DE 280000 0000   0206        PI    KFECH      LOAD K4.
     00E1 72            0207        LIS   2
     00E2 FB            0208        NS    11
     00E3 8404   00E8   0209        BZ    M4         BR IF K CKSM FAILED.
     00E5 290091 0091   0210        JMP   M3
                        0211  *
     00E8 280000 0000   0212  M4    PI    NRMLZ
     00EB 280000 0000   0213        PI    SUBEXP
                        0214  *D------------------------------------------------------------
     00EE 280000 0000   0215        PI    MULBIN                        (K5*T-4897) BY K4.
                        0216  *-------------------------------------------------------------
     00F1 20C6          0217        LI    H'C6'
     00F3 5D            0218        LR    I,A
     00F4 20A7          0219        LI    H'A7'
     00F6 5C            0220        LR    S,A
                        0221  *E------------------------------------------------------------
     00F7 280000 0000   0222        PI    MULBIN                        BY .00001
                        0223  *-------------------------------------------------------------
     00FA 280000 0000   0224        PI    SHRES
                        0225  *
     00FD 66            0226        LISU  6
     00FE 6F            0227        LISL  7
     00FF 4D            0228        LR    A,I        MOVE: R67 -> R60    RES EXP FROM EMME#.
     0100 5C            0229        LR    S,A
                        0230  *
     0101 67            0231        LISU  7
```

```
EMME [illegible] FILE 6 REV [illegible] JOHN
ERRS LOC OBJECT ADDR LINE          SOURCE STATEMENT
     0102 69             0232          LISL  1
     0103 2040           0233          LI    H'40'     ADD 1 TO (KT X DT).
     0105 CC             0234          AS    S
     0106 5C             0235          LR    S,A
                         0236  *
     0107 280000 0000    0237          PI    NRM14     DIVISOR.
     010A 280000 0000    0238          PI    ADDEXP
                         0239  *
     010D 67             0240          LISU  7
     010E 69             0241          LISL  1
     010F 4E             0242          LR    A,D       MOVE: R70 -> R72  1+(KT*DT) TO DIVISOR.
     0110 50             0243          LR    0,A             R71 -> R73.
     0111 4C             0244          LR    A,S
     0112 6A             0245          LISL  2
     0113 5D             0246          LR    I,A
     0114 40             0247          LR    A,0
     0115 5C             0248          LR    S,A
                         0249  *
     0116 66             0250          LISU  6
     0117 6D             0251          LISL  5
     0118 4D             0252          LR    A,I        MOVE: R65 -> R70   EMME# TO DIVIDEND.
     0119 50             0253          LR    0,A              R66 -> R71.
     011A 4C             0254          LR    A,S
     011B 67             0255          LISU  7
     011C 69             0256          LISL  1
     011D 5E             0257          LR    D,A
     011E 40             0258          LR    A,0
     011F 5C             0259          LR    S,A
                         0260  *F----------------------------------------------------------------
     0120 280000 0000    0261          PI    DIVRIN                   EX = (DS/DR) BY (1+KTDT).
                         0262  *----------------------------------------------------------------
     0123 69             0263          LISL  1
     0124 4E             0264          LR    A,D        MOVE: R70 -> R65   SAVE EX AND EXP.
     0125 50             0265          LR    0,A              R71 -> R66   (EX IS X 2**15).
     0126 4C             0266          LR    A,S
     0127 66             0267          LISU  6
     0128 6D             0268          LISL  5
     0129 5D             0269          LR    I,A
     012A 40             0270          LR    A,0
     012B 5C             0271          LR    S,A
                         0272  *
     012C 68             0273          LISL  0          MOVE: R60 -> R67
     012D 4E             0274          LR    A,D
     012E 5C             0275          LR    S,A
                         0276  *
     012F 72             0277          LIS   2
     0130 50             0278          LR    0,A
     0131 280000 0000    0279          PI    KFECH      LOAD K2.
                         0280  *
     0134 280000 0000    0281          PI    NRML7      K2.
     0137 280000 0000    0282          PI    SUBEXP
                         0283  *
     013A 67             0284          LISU  7
     013B 69             0285          LISL  1
     013C 280000 0000    0286          PI    NRML7
```

```
FMME SMT  FILE 6  REV 13 APR 82  JAK/DICKEY-JOHN
ERRS LOC OBJECT ADDR LINE          SOURCE STATEMENT
     013F 280000 0000 0287          PI    SHREXP
                      0288  *
     0142 20FE        0289          LI    -2        ADJUST EXPONENT     +32,MULT.
     0144 57          0290          LR    7,A                           -19,K2.
     0145 280000 0000 0291          PI    ADDEXP                        -15,DPADJ.
                      0292  *G------------------------------------------------------------
     0148 280000 0000 0293          PI    MULBIN                        K2 AND EX.
                      0294  *-------------------------------------------------------------
     014B 20CC        0295          LI    H'CC'
     014D 5D          0296          LR    I,A
     014E 20CC        0297          LI    H'CC'
     0150 5C          0298          LR    S,A
                      0299  *H------------------------------------------------------------
     0151 280000 0000 0300          PI    MULBIN                          K2(EX) BY .1 .
                      0301  *-------------------------------------------------------------
     0154 280000 0000 0302          PI    SHRES
                      0303  *
     0157 4D          0304          LR    A,I       MOVE: R75 -> R62  SAVE K2(EX)/10.
     0158 50          0305          LR    0,A             R76 -> R63.
     0159 4C          0306          LR    A,S
     015A 66          0307          LISU  6
     015B 6B          0308          LISL  3
     015C 5E          0309          LR    D,A
     015D 40          0310          LR    A,0
     015E 5C          0311          LR    S,A
                      0312  *
     015F 6F          0313          LISL  7
     0160 71          0314          LIS   1
     0161 CD          0315          AS    I         MOVE: R67 -> R60  RESTORE EX & EXP.
     0162 5C          0316          LR    S,A       INC EXPONENT OF FX FOR LOG ROUTINE.
                      0317  *
     0163 6D          0318          LISL  5
     0164 4D          0319          LR    A,I             R65 -> R70.
     0165 50          0320          LR    0,A             R66 -> R71.
     0166 4C          0321          LR    A,S
     0167 67          0322          LISU  7
     0168 69          0323          LISL  1
     0169 5E          0324          LR    D,A
     016A 40          0325          LR    A,0
     016B 5C          0326          LR    S,A
                      0327  *
     016C 280000 0000 0328          PI    SHRES     FX.
                      0329  *
     016F 4D          0330          LR    A,I       MOVE: R70 -> R1   FX TO LOG REGISTERS.
     0170 51          0331          LR    1,A             R71 -> R0.
     0171 4C          0332          LR    A,S
     0172 50          0333          LR    0,A
                      0334  *I------------------------------------------------------------
                      0335  *-------------------------------------------------------------
     0173 280000 0000 0336          PI    LOG                           LOG (EX).
                      0337  *-------------------------------------------------------------
                      0338  *-------------------------------------------------------------
     0176 66          0339          LISU  6         INIT EXPONENT = 6  +32,MULT.
     0177 68          0340          LISL  0                             -12,LOG.
```

```
FMME SMT  FILE 6  REV 1: APR 82  HAF/DIEFEL JOHN
ERR  LOC OBJECT ADDR LINE        SOURCE STATEMENT
     0178 20FD        0341        LI     -3                               -23,LN&K3.
     017A 5C          0342        LR     S,A
                      0343  *
     017B 6E          0344        LISL   6
     017C 4E          0345        LR     A,D       MOVE: R65 -> R70   LOG(EX) TO DIVIDEND.
     017D 50          0346        LR     0,A             R66 -> R71.
     017E 4C          0347        LR     A,S
     017F 67          0348        LISU   7
     0180 68          0349        LISL   0
     0181 5D          0350        LR     I,A
     0182 40          0351        LR     A,0
     0183 5D          0352        LR     I,A
                      0353  *
     0184 2071        0354        LI     H'71
     0186 5D          0355        LR     I,A
     0187 20E3        0356        LI     H'E3
     0189 5C          0357        LR     S,A
                      0358  *J---------------------------------------------------------
     018A 280000 0000 0359        PI     MULBIN         '    LOG(EX) BY .693147 X .01.
                      0360  *---------------------------------------------------------
     018D 73          0361        LIS    3
     018E 50          0362        LR     0,A
     018F 280000 0000 0363        PI     KFETCH    LOAD K3.
                      0364  *
                      0365  *---------------------------------------------------------
     0192 280000 0000 0366        PI     MULBIN                     LN(X) * K3.
                      0367  *M  ------------------------------------------------------
     0195 280000 0000 0368        PI     SHRES
                      0369  *
     0198 0A          0370        LR     A,IS
     0199 50          0371        LR     0,A
     019A 66          0372        LISU   6
     019B 6A          0373        LISL   2
     019C 0A          0374        LR     A,IS
     019D 51          0375        LR     1,A
                      0376  *
     019E 280000 0000 0377        PI     BSUB                     T = K2(X) - K3(LN(X)).
                      0378  *
     01A1 66          0379        LISU   6         INITIALIZE EXPONENT = -3   +16,MULT.
     01A2 68          0380        LISL   0                                    -19,K1.
     01A3 20FD        0381        LI     -3
     01A5 5C          0382        LR     S,A
                      0383  *
     01A6 71          0384        LIS    1
     01A7 50          0385        LR     0,A
     01A8 280000 0000 0386        PI     KFECH     LOAD K1.
                      0387  *
     01AB 280000 0000 0388        PI     NRMLZ
                      0389  *
     01AE 68          0390        LISL   0
     01AF 20CC        0391        LI     H'CC'
     01B1 5D          0392        LR     I,A
     01B2 20CC        0393        LI     H'CC
     01B4 5C          0394        LR     S,A
                      0395  *
     01B5 280000 0000 0396        PI     SUBEXP
```

EMME SMT FILE A REV 13 APR 82 JAE/DILLEY JOHN

```
ERRS LOC OBJECT ADDR LINE          SOURCE STATEMENT
                     0397 *------------------------------------------------------
     01B8 280000 0000 0398           PI    MULBIN                   K1 BY .1 .
                     0399 *------------------------------------------------------
     01BB 280000 0000 0400           PI    SHRES
                     0401 *
     01BE 66          0402           LISU  6
     01BF 6A          0403           LISL  2
     01C0 70          0404           CLR
     01C1 CA          0405           AS    10
     01C2 9104   01C7 0406           BM    M5         BR IF T IS NEGATIVE.
     01C4 280000 0000 0407           PI    BSUB3      NEGATE T.
                     0408 *
     01C7 2032        0409 M5        LI    0 62
     01C9 50          0410           LR    0,A
     01CA 201C        0411           LI    0 34
     01CC 51          0412           LR    1,A
     01CD 67          0413           LISU  7
     01CE 68          0414           LISL  0
                     0415 *
     01CF 280000 0000 0416           PI    BSUB
                     0417 *
     01D2 0D          0418           LR    P0,Q
                     0419 *
                     0420           END
 00 ERRS
```

-EMME SMT MATH - 13 APR 82

% LEAN = K1 + K2(X) - K3 LN(X)

X = EMME# / ( 1 + K4*DT )

EMME# = DS/DR * K6 * K7

DT = K5*T - 4897

DS = DE - D

DR = D - R

PNTR = (T3 T1) / (T2-T1)

M = MULTIPLIER FROM REGISTER AT TTAB (PNTR

M(T3-T1) + T1 = FINAL TEMPERATURE

| | | |
|---|---|---|
| K0 | CKSM ON CONSTANTS - USER GENERATED | 0 TO 255 |
| K1 | EQUATION CONSTANT - OFFSET | 0 TO 655.35 |
| K2 | EQUATION CONSTANT - LINEAR TERM SCALER | 0 TO 655.35 |
| K3 | EQUATION CONSTANT - LOGARITHMIC TERM SCALER | 0 TO 65.535 |

```
K4       TEMPERATURE COMPENSATION                         0   TO  0.0255

K5       TEMPERATURE PROBE NORMALIZATION                  0   TO  6.5535

K6       TUBE DIAMETER NORMALIZATION                      0   TO  6.5535

K7       UNIT NORMALIZATION                               0   TO  6.5535


         BINARY TO DECIMAL CORRECTION FACTORS
         DECIMAL                            BINARY EQUIVALENT FOR MATH

K1       .1       MULTIPLY ENTERED BY       52428 * 2**-19     CCCC

K2       .1                                 52428 * 2**-19     CCCC

K3       .01  X  .693147                    58145 * 2**-23     E321

K4       .00001                             42950 * 2**-32     A7C6

K5       .0001                              53687 * 2**-29     D1B7

K6,K7    .00000001                          43980 * 2** 42     ABCC


--------------------------EMME SMT ERROR CODES-------19 MAR 82

   ERROR 01       SAMPLE REMOVED TOO SOON   (B=OUT,T=IN)
   ERROR 03       INVALID SENSOR STATUS     (B=IN,T=OUT)

   ERROR 04       EC DATA OUT OF RANGE      (1.8 +/-.5)

   ERROR 05       TEMPERATURE TOO LOW       (T<31.0 F)

   ERROR 06       DELTR DRIFT EXCESSIVE     (>10 COUNTS)

   ERROR 07       CONSTANT CKSM FAIL


---------------EMME SMT NOVRAM MAP-----------------------4 MAR 82

ADDRESS        11          10          01          00
           ----------------------------------------------------
0000XX     ! PROD A    ! PROD A    ! PROD A    ! PROD A    !
           !   K1      !   K1      !    CKSM K1 THRU K4    !
           ----------------------------------------------------
0001XX     ! PROD A    ! PROD A    ! PROD A    ! PROD A    !
           !   K2      !   K2      !   K1      !   K1      !
           ----------------------------------------------------
0010XX     ! PROD A    ! PROD A    ! PROD A    ! PROD A    !
           !   K3      !   K3      !   K2      !   K2      !
           ----------------------------------------------------
```

| | | | | |
|---|---|---|---|---|
| 0011XX | PROD A<br>K4 | PROD A<br>K4 | PROD A<br>K3 | PROD A<br>K3 |
| 0100XX | PROD B<br>K1 | PROD B<br>K1 | PROD B<br>CKSM K1 THRU K4 | PROD B |
| 0101XX | PROD B<br>K2 | PROD B<br>K2 | PROD B<br>K1 | PROD B<br>K1 |
| 0110XX | PROD B<br>K3 | PROD B<br>K3 | PROD B<br>K2 | PROD B<br>K2 |
| 0111XX | PROD B<br>K4 | PROD B<br>K4 | PROD B<br>K3 | PROD B<br>K3 |
| 1000XX | PROD C<br>K1 | PROD C<br>K1 | PROD C<br>CKSM K1 THRU K4 | PROD C |
| 1001XX | PROD C<br>K2 | PROD C<br>K2 | PROD C<br>K1 | PROD C<br>K1 |
| 1010XX | PROD C<br>K3 | PROD C<br>K3 | PROD C<br>K2 | PROD C<br>K2 |
| 1011XX | PROD C<br>K4 | PROD C<br>K4 | PROD C<br>K3 | PROD C<br>K3 |
| 1100XX | ALL PROD<br>K5 | ALL PROD<br>K5 | ALL PROD<br>K5 | ALL PROD<br>K5 |
| 1101XX | K6 | K6 | K6 | K6 |
| 1110XX | K7 | K7 | K7<br>CKSM K3 THRU K7 | K7 |

------------------EMME SMT I/O PORT ASSIGNMENT-------------4 MAR 82

| PORT | EXT SENS ACTIVE | ASSIGNMENT | I | O |
|---|---|---|---|---|
| 0.0 | | PRODUCT SELECT - FTU KBD - RAM DATA | X | X |
| 0.1 | | " " | X | X |
| 0.2 | | " " | X | X |
| 0.3 | | " " | X | X |
| 0.4 | HI | DISPLAY LOAD | | X |

| | | | | |
|---|---|---|---|---|
| 0.5 | LO | DISPLAY CLK | | X |
| 0.6 | HI | DISPLAY DATA | | X |
| 0.7 | HI | TOP POSITION SENSOR | X | |
| | | | (I) | (O) |
| 1.0 | Q | EVENT SELECT Q=HI=TEMP Q=LO=PHI DETECTOR | | X |
| 1.1 | Q | RESULT READ-OUT Q=HI=%FAT Q=LO=%LEAN | X | |
| 1.2 | | NU | | |
| 1.3 | HI | FTU KEY DEPRESSED | X | |
| 1.4 | HI | PHI DETECTOR SELECT - OFFSET | | X |
| 1.5 | LO | SMT PRODUCT KBD ENABLE | | X |
| 1.6 | LO | PHI DETECTOR SELECT - REFR | | X |
| 1.7 | LO | FTU PRESENT | X | |
| | | | (I) | (O) |
| 4.0 | LO | ROM STORE | | X |
| 4.1 | LO | ARRAY RECALL | | X |
| 4.2 | LO | WRITE ENABLE | | X |
| 4.3 | LO | CHIP SELECT | | X |
| 4.4 | HI | PRODUCT A LED | | X |
| 4.5 | HI | PRODUCT B LED | | X |
| 4.6 | HI | PRODUCT C LED | | X |
| 4.7 | | NU | | |
| | | | (I) | (O) |
| 5.0 | HI | A0 - RAM ADDRESS | | X |
| 5.1 | HI | A1 | | X |
| 5.2 | HI | A2 | | X |
| 5.3 | HI | A3 | | X |
| 5.4 | HI | A4 | | X |
| 5.5 | HI | A5 | | X |
| 5.6 | HI | FTU KBD ENABLE | | X |
| 5.7 | HI | EMME STEP SWITCH | X | |

EXTERNAL INTERRUPT PHI DETECTOR INPUT OR TEMPERATURE DETECTOR

----------------EMME SMT SCRATCHPAD RAM MAP--------------4 MAR 82

| | | |
|---|---|---|
| R 00 | MISC | |
| R 01 | MISC | |
| R 02 | MISC | |
| R 03 | MISC | |
| R 04 | MISC | |
| R 05 | MISC | |
| R 06 | MISC | |
| R 07 | FLAGS | |
| R 10 | FLAGS | REG 8 |
| R 11 | STATUS SAVE / TEMPORARY FLAGS | REG 9 J |
| R 12 | FLAGS | REG 10 HU |
| R 13 | FLAGS | REG 11 HL |
| R 14 | SUBROUTINE STACK | REG KU |
| R 15 | SUBROUTINE STACK | REG KL |

```
R 16   SUBROUTINE STACK                          REG 0U
R 17   SUBROUTINE STACK                          REG 01

R 20   DISPLAY FTU    LSD
R 21   DISPLAY FTU          DP1
R 22   DISPLAY FTU          DP2
R 23   DISPLAY FTU          DP3
R 24   DISPLAY FTU          DP4
R 25   DISPLAY FTU          DP5
R 26   DISPLAY FTU          DP6
R 27   DISPLAY FTU    MSD   DP7

R 30   DISPLAY SMT    MESSAGES
R 31   DISPLAY SMT    MESSAGES AND LSD
R 32   DISPLAY SMT    MID AND LSB OF LSD
R 33   DISPLAY SMT    MSD
R 34   % LEAN     AND TEMPORARY SAVE
R 35   % LEAN
R 36   TEMPERATURE 1ST
R 37   TEMPERATURE 1ST

R 40   EMPTY CELL DATA
R 41   EMPTY CELL DATA
R 42   EMPTY + REFR DATA
R 43   EMPTY + REFR DATA
R 44   FULL CELL DATA
R 45   FULL CELL DATA
R 46   FULL + REFR DATA
R 47   FULL + REFR DATA

R 50   EMME #
R 51   EMME #
R 52   COUNTER
R 53   ERRORS
R 54   TEMPERATURE 2ND
R 55   TEMPERATURE 2ND
R 56   TEMPERATURE 3RD
R 57   TEMPERATURE 3RD

R 60   EVENT COUNTER  AND  MATH EXPONENT
R 61   EVENT COUNTER
R 62   EVENT COUNTER  AND  MATH SAVE
R 63   EVENT COUNTER  AND  MATH SAVE


R 64   MATH SAVE
R 65   MATH SAVE
R 66   MATH SAVE
R 67   MATH SAVE

R 70   MATH CALCS
R 71   MATH CALCS
R 72   MATH CALCS
R 73   MATH CALCS
R 74   MATH CALCS
```

R 75 MATH CALCS
R 76 MATH CALCS
R 77 MATH CALCS

---------------------EMME SMT FLAG REGISTER MAP--------------4 MAR 82

REG 7.0 SMT DISPLAY MODE 00 = % MODE 01 = EMME # MODE
REG 7.1 SMT DISPLAY MODE 10 = DEGREES C 11 = DEGREES F
REG 7.2 RAM WRITE OR COLLECT TEMPERATURE COUNTS
REG 7.3 WARMING UP
REG 7.4 REMOVE
REG 7.5 INSERT
REG 7.6 WAIT
REG 7.7 ERROR

REG 8.0 FTU DIGIT 7
REG 8.1 FTU DIGIT 7
REG 8.2 FTU DIGIT 7
REG 8.3 FTU DIGIT 7
REG 8.4 EMPTY DONE
REG 8.5 SAMPLE DONE
REG 8.6 BOTTOM OUT
REG 8.7 TOP OUT

REG 10.0 30 SECONDS UP / STORE DISABLE
REG 10.1 FTU DISPLAY DECIMAL SELECT
REG 10.2 FTU DISPLAY DECIMAL SELECT
REG 10.3 NEGATIVE DEGREES C
REG 10.4 PRODUCT A
REG 10.5 PRODUCT B
REG 10.6 PRODUCT C
REG 10.7 NEGATIVE RESULT FROM SUBTRACT ROUTINE

REG 11.0 SMT TEMPERATURE DISPLAY (NOT FTU TEMPERATURE DISPLAY)
REG 11.1 CONSTANT CKSM FAIL
REG 11.2 LAST FETCHED CONSTANT ADDRESS
REG 11.3 LAST FETCHED CONSTANT ADDRESS
REG 11.4 LAST FETCHED CONSTANT ADDRESS
REG 11.5 LAST FETCHED CONSTANT ADDRESS
REG 11.6 LAST FETCHED CONSTANT ADDRESS
REG 11.7 LAST FETCHED CONSTANT ADDRESS

R 20 THRU 27 - FTU DISPLAY REGISTERS
REG R.0 DP (NU FOR R20)
REG R.1 C SEGMENT
REG R.2 D SEGMENT

REG R.3 E SEGMENT
REG R.4 B SEGMENT
REG R.5 A SEGMENT
REG R.6 F SEGMENT
REG R.7 G SEGMENT

```
REG 30.0   % LEAN        MESSAGE
REG 30.1   % FAT         MESSAGE
REG 30.2   REMOVE        MESSAGE
REG 30.3   B4 & C4       SEGMENTS OF MSD (HALF DIGIT)
REG 30.4   WAIT          MESSAGE
REG 30.5   DEG F         MESSAGE
REG 30.6   ERROR         MESSAGE
REG 30.7   DEG C         MESSAGE

REG 31.0   DATA          MESSAGE
REG 31.1   INSERT        MESSAGE
REG 31.2   B3 SEGMENT
REG 31.3   A3 SEGMENT
REG 31.4   F3 SEGMENT
REG 31.5   G3 SEGMENT
REG 31.6   E3 SEGMENT
REG 31.7   D3 SEGMENT

REG 32.0   C3 SEGMENT
REG 32.1   G2 SEGMENT
REG 32.2   F2 SEGMENT
REG 32.3   E2 SEGMENT
REG 32.4   D2 SEGMENT
REG 32.5   A2 SEGMENT
REG 32.6   C2 SEGMENT
REG 32.7   B2 SEGMENT

REG 33.0   DECIMAL POINT
REG 33.1   E1 SEGMENT
REG 33.2   G1 SEGMENT
REG 33.3   F1 SEGMENT
REG 33.4   D1 SEGMENT
REG 33.5   C1 SEGMENT
REG 33.6   B1 SEGMENT
REG 33.7   A1 SEGMENT

REG 53.0   ERROR 01 - SAMPLE REMOVED TOO SOON OR BOTTOM SENSOR NOT SEEN
REG 53.1   ERROR 02 - SAMPLE INSERTED TOO SOON, EMPTY NOT YET FINISHED
REG 53.2   ERROR 03 - INVALID SENSOR STATUS, I.E. BOTTOM IN, TOP OUT
REG 53.3   ERROR 04 - EMPTY CELL DATA OUT OF RANGE
REG 53.4   ERROR 05 - TEMPERATURE TOO LOW
REG 53.5   ERROR 06 - DELIR DRIFT EXCESSIVE
REG 53.6   ERROR 07 - CONSTANT CKSM FAIL
REG 53.7   ERROR XX - NU

--------------------EMME FTU DISPLAY------------------------4 MAR 82

                 DIGIT SEQUENCE 8.7.6.5.4.3.2.1

          A                CHARACTER    SEGMENTS          CODE
        -----              ---------    --------          ----
    !           !                       G F A B E D C X
    !           !
  F !           ! B            0        0 1 1 1 1 1 1 0    7E
    !           !              1        0 0 0 1 0 0 1 0    12
    !           !              2        1 0 1 1 1 1 0 0    BC
```

```
 !   G   !            3     1 0 1 1 0 1 1 0     BA
 ---------            4     1 1 0 1 0 0 1 0     D2
 !       !            5     1 1 1 0 0 1 1 0     E6
 !       !            6     1 1 1 0 1 1 1 0     EE
E!       ! C          7     0 0 1 1 0 0 1 0     32
 !       !            8     1 1 1 1 1 1 1 0     FE
 !       !            9     1 1 1 1 0 1 1 0     F6
 !       !
 ---------

---------------------EMME SMT DISPLAY---                 ----------

            DIGIT SEQUENCE 4 3 2.1

        DIGIT 3           DENTBA        DIGIT 2          DENTBB
CHAR    SEGMENTS          CODE          SEGMENTS         CODE
----    --------          -----         --------         ----
     D E G F A B X X  C            B C A D E F G X

 0   1 1 0 1 1 1 0 0  1   DC 01    1 1 1 1 1 1 0 0        FC
 1   0 0 0 0 0 1 0 0  1   04 01    1 1 0 0 0 0 0 0        C0
 2   1 1 1 0 1 1 0 0  0   EC 00    1 0 1 1 1 0 1 0        BA
 3   1 0 1 0 1 1 0 0  1   AC 01    1 1 1 1 0 0 1 0        F2
 4   0 0 1 1 0 1 0 0  1   34 01    1 1 0 0 0 1 1 0        C6
 5   1 0 1 1 1 0 0 0  1   B8 01    0 1 1 1 0 1 1 0        76
 6   1 1 1 1 1 0 0 0  1   F8 01    0 1 1 1 1 1 1 0        7E
 7   0 0 0 0 1 1 0 0  1   0C 01    1 1 1 0 0 0 0 0        E0
 8   1 1 1 1 1 1 0 0  1   FC 01    1 1 1 1 1 1 1 0        FE
 9   1 0 1 1 1 1 0 0  1   BC 01    1 1 1 1 0 1 1 0        F6

        DIGIT 1           DENTBC
CHAR    SEGMENTS          CODE
----    --------          ----
     A B C D F G E X

 0   1 1 1 1 1 0 1 0       FA
 1   0 1 1 0 0 0 0 0       60
 2   1 1 0 1 0 1 1 0       D6
 3   1 1 1 1 0 1 0 0       F4
 4   0 1 1 0 1 1 0 0       6C
 5   1 0 1 1 1 1 0 0       BC
 6   1 0 1 1 1 1 1 0       BE
 7   1 1 1 0 0 0 0 0       E0
 8   1 1 1 1 1 1 1 0       FE
 9   1 1 1 1 1 1 0 0       FC

------------------------EMME SMT/FTU MATH SUBROUTINES -----------4 MAR 82

BSUB     SUBTRACTS DATA POINTED TO BY -R0- FROM DATA POINTED TO
          BY -ISAR- AND LEAVES RESULT IN -R1-
          ISAR RETURNS AT MSB OF DIFFERENCE

BSUB3    NEGATES 16 BIT VALUE AT ISAR,ISAR+1

BTOD     CONVERTS # POINTED TO BY -ISAR+ISAR+1- TO BCD
          R0=POINTER TO CORRECT CONVERSION FACTOR
          (0=DATA  5=EMME#  10=% OR DEGREES)
          OUTPUT RETURNED IN MSD 2,3,4,5,6 LSD
```

NRMLZ LEFT JUSTIFIES 16 BIT VALUE AT ISAR,ISAR-1
NUMBER AND SIGN OF SHIFTS RECORDED IN R2

ADDEXP ADDS COUNTS IN R2 TO EXPONENT REGISTER R60

SUBEXP SUBTRACTS COUNTS IN R2 FROM EXPONENT REGISTER R60

SHRES SHIFTS RESULT IN R75,76 BY SIGN AND MAGNITUDE OF EXP REG R60

MULBIN MULTIPLIES 70,71 BY 72,73 RESULT IN 75,76

DIVBIN DIVIDES 70,71 BY 72,73 RESULT IN 75,76

LOG TAKES LOG BASE 2 OF NUMBER IN R0,R1 RESULT IN LSB R64-R66 MSB

------------------------EMME SMT MATH SEQUENCE FOR % LEAN-- ----

```
 1) INIT       EXPONENT = 9  +16,DPADJ +48,MULT -13,DIV -42,K6,K7
 2) BSUB       DR = D - R
 3) NRM14      DIVISOR DR
 4) ADDEXP
 5) BSUB       DS = DE - D
 6) NRM14      DIVIDEND DS
 7) SUBEXP
 8) DIVBIN     DS / DR
 9) LOAD       .00000001 K6,K7 CORRECTION FACTOR
10) NRMLZ      DS / DR
11) SUBEXP
12) MULBIN     DS/DR BY .00000001
13) LOAD       K6
14) NRMLZ      K6
15) SUBEXP
16) MULBIN     (DS/DR X .00000001) BY K6
17) LOAD       K7
18) NRMLZ      K7
19) SUBEXP
20) MULBIN     K6(DS/DR X .00000001) BY K7
21) SAVE       K6 K7 DS/DR (EMME #)
22) SHRES
23) STORE      EMME# FOR DISPLAY
24) INIT       EXPONENT = 3  +32,MULT -29,K5
25) NRMLZ      TEMPERATURE
26) SUBEXP
27) LOAD       K5

28) NRMLZ      K5
29) SUBEXP
30) MULBIN     TEMPERATURE BY K5
31) LOAD       .0001 K5 CORRECTION FACTOR
32) MULBIN     K5 T  BY .0001
```

```
33) SHRES
34) INIT       EXPONENT = 14  +32,MULT +14,DPADJ -32,K4
35) LOAD       4897
36) BSUB       K5 T - 4897
37) NRMLZ      K5T-4897
38) SUBEXP
39) LOAD       K4
40) NRMLZ      K4
41) SUBEXP
42) MULBIN     (K5T-4897) BY K4
43) LOAD       .00001 K4 CORRECTION FACTOR
44) MULBIN     K4(K5T-4897) BY .00001
45) SHRES
46) RESTORE    EXPONENT FROM EMME # (21)
47) ADD        1.0000 TO K4(K5T-4897)
48) NRMLZ      DIVISOR 1+K4(K5T-4897)
49) ADDEXP
50) DIVBIN     EX - EMME# BY 1+K4(K5T-4897)
51) SAVE       EX AND EXPONENT
52) LOAD       K2
53) NRMLZ      K2
54) SUBEXP
55) NRMLZ      EX
56) SUBEXP
57) ADDEXP     +32,MULT -19,K2 -15,DPADJ
58) MULBIN     EX BY K2
59) LOAD       .1 K2 CORRECTION FACTOR
60) MULBIN     K2EX BY .1
61) SHRES
62) SAVE       K2EX
63) RESTORE    EX AND EXPONENT
64) DPADJ      INCREMENT DP TO POSITION DATA FOR LOG ROUTINE
65) SHRES
66) LOG        EX  (LOG RESULT ALWAYS POSITIVE)
67) INIT       EXPONENT = -3  +32,MULT -12,LOG -23,K3,LOG TO LN
68) LOAD       .00693147 K3 AND LOG(2) TO LOG(E) CONVERSION FACTOR
69) MULBIN     EX BY .00693147
70) LOAD       K3
71) MULBIN     EX BY K3
72) SHRES
73) BSUB       M = K2(EX) - K3(LN(EX))  (POSITIVE LN)
74) INIT       EXPONENT = -3  +16,MULT -19,K1
75) LOAD       K1
76) NRMLZ      K1
77) SUBEXP
78) LOAD       .1 K1 CORECTION FACTOR
79) MULBIN     K1 BY .1
80) SHRES
81) BSUB3      NEGATE M IF M IS POSITIVE
82) BSUB       K1 - (-M)
83) STORE      % LEAN
```

While the invention has been described herein with reference to a preferred embodiment, the invention is not limited thereto. Those skilled in the art may devise various changes, alternatives and modifications upon reading the foregoing description. The invention includes such alternatives, changes and modifications insorfar as they fall within the spirit and scope of the appended claims.

The invention is claimed as follows:

1. A test apparatus for measuring the amount of at least one constituent present in a sample of material, wherein said at least one constituent bears a known relationship to the electrical conductivity of the sample, comprising: a sensor including receptacle means for receiving a sample of material therein and defining an axis, and field producing means; said field producing means including means for producing an electromagnetic field within said receptacle means, means for substantially confining said electromagnetic field to a predetermined, fixed volume within said receptacle means and substantially coaxially therewith, and means for maintaining said confined electromagnetic field substantially uniform and continuous throughout said predetermined, fixed volume to which it is confined; said predetermined, fixed volume being located such that the material of said sample extends over the entire axial length thereof when said sample is introduced into the test apparatus.

2. Apparatus according to claim 1 and further including monitoring circuit means coupled with said sensor and responsive thereto for producing an output signal which bears a predetermined relationship with the real impedance of said sensor both when empty and when the sample is received therein, said output signal thereby bearing a predetermined relationship with the conductivity of said sample, when present, said monitoring circuit means being further substantially unresponsive to the dielectric constant of either or both of said sensor or said sample.

3. Apparatus according to claim 1 wherein said receptacle means comprises means defining said predetermined, fixed volume and wherein said field producing means comprises coil means disposed for substantially coaxially surrounding said predetermined, fixed volume.

4. Apparatus according to claim 3 and further including a sample container removably insertable with respect to said sample receptacle and of similar dimensions thereto.

5. Apparatus according to claim 3 wherein said coil means comprises a plurality of windings arranged about a predetermined axis in a generally cylindrical configuration and electrically interconnected to produce a substantially continuous and uniform magnetic field along a predetermined portion of the axial length of said predetermined axis.

6. Apparatus according to claim 1 wherein said maintaining means includes means for substantially eliminating axial electric field components in said electromagnetic field.

7. Apparatus according to claim 3 or claim 5 wherein said maintaining means includes field controlling means for substantially axial electric field components in said electromagnetic field.

8. Apparatus according to claim 7 wherein said field controlling means comprises axially extending electrically conductive means coaxially aligned with said coil means.

9. Apparatus according to claim 8 wherein said field controlling means further comprises a cylinder mounted coaxially with said coil means and wherein said electrically conductive means comprises a plurality of axially extending conductors carried in a radially spaced arrangement upon said cylinder.

10. Apparatus according to claim 9 wherein said cylinder is mounted intermediate said cylindrical sample-receiving volume and said coil means.

11. Apparatus according to claim 5 wherein said plurality of windings comprises a pair of respectively axially outer windings coupled with a ground potential and a plurality of windings intermediate said axially outer windings and electrically interconnected to direct electrical currents flowing therethrough in clockwise and counterclockwise directions in a predetermined sequence so as to achieve a substantially zero net current flow along the axial length of said coil means.

12. Apparatus according to claim 11 wherein said intermediate windings comprise a plurality of equally spaced substantially cylindrical conductors arranged in an even number of groups, each group containing a like number of said conductors, all of the conductors being coupled in electrical series circuit, and successive groups thereof being coupled in circuit to direct current in clockwise and counterclockwise directions in alternating fashion from group to group.

13. Apparatus according to claim 12 wherein respective axially outermost ends of said plurality of intermediate windings and a center point thereof are coupled to a ground potential and wherein signal input/output points are provided substantially equidistant on said plurality of intermediate windings between said center point thereof and each end thereof.

14. Apparatus according to claim 13 and further including a sample container removably insertable with respect to said sample receptacle and of similar dimensions thereto.

15. Apparatus according to claim 14 wherein said sample container coaxially interfits within said coil so as to substantially position a sample of material therein within said coil, said intermediate windings substantially defining said predetermined volume.

16. Apparatus according to claim 11, claim 12 or claim 15 wherein said intermediate windings are twelve in number and arranged in four groups of three windings each.

17. Apparatus according to claim 2 or claim 13 wherein said monitoring circuit means comprises balanced modulator circuit means coupled with said sensor and responsive to the real power absorbed by said predetermined, fixed volume for producing a modulated output signal directly proportional to said real power absorbed and bearing a predetermined relationship to the conductivity of said predetermined, fixed volume both in the presence of said sample and in the absence of said sample.

18. Apparatus according to claim 17 wherein said monitoring circuit means further includes calculating means responsive to said modulated output signal for calculating said amount of said at least one constituent present in said sample and for producing a corresponding constituent content output signal.

19. Apparatus according to claim 18 and further including reference means and selector means in said monitoring circuit means for said reference means both when said sample is present and when said sample is absent for referencing said modulated output signal.

20. Apparatus according to claim 19 wherein said calibration means includes a known fixed impedance reference element and said selector means is operative for adding the impedance thereof to the impedance of said predetermined fixed volume.

21. Apparatus according to claim 20 and further including nulling means for producing a null level modulated output signal, further selector means in said monitoring circuit means for selecting said nulling means for nulling the calculating means.

22. Apparatus according to claim 17 and further including sample presence sensor means for detecting the presence or absence of said sample, said monitoring circuit means being responsive to said sample presence sensor means for controlling the sequence of calculating.

23. Apparatus according to claim 18 and further including memory means for storing a plurality of predetermined empirical constants for use by said calculating means in calculating said constituent content of said sample.

24. Apparatus according to claim 23 wherein said monitoring circuit means includes a microcomputer and wherein said memory means comprises at least one NOVRAM operatively coupled with said microcomputer.

25. Apparatus according to claim 22 and further including temperature correction means comprising temperature sensor means disposed for measuring the temperature of said sample and means operatively coupling said temperature sensor means with said calculating means, said calculating means being responsive to said temperature sensor means for calculating said constituent content further in accordance with the temperature of the sample.

26. Apparatus according to claim 1 wherein said at least one constituent content comprises the fat content of the sample.

27. Apparatus according to claim 26 wherein said material is meat.

28. A test apparatus for measuring the amount of at least one constituent in a sample of material, which constituent bears a known relationship to the electrical conductivity of the sample, comprising: a sensor including receptacle means for receiving a sample of material therein and field producing means for producing an electromagnetic field within said receptacle, and monitoring circuit means coupled with said sensor and responsive thereto for producing an output signal which bears a predetermined relationship with substantially only the real component of the impedance of said sensor and therefore with the conductivity of said sample substantially without regard for the dielectric constant of said sample, when said sample is received in said receptacle.

29. Apparatus according to claim 28 wherein said field producing means comprises coil means disposed for surrounding a predetermined portion of said receptacle means and signal generator means for driving said coil means.

30. Apparatus according to claim 29 wherein said monitoring circuit means comprises balanced modulator circuit means coupled with said signal generator means and with said coil means and responsive to the real power absorbed in the field of said coil for producing a modulated output signal directly proportional to said real power absorbed and bearing a predetermined relationship to the conductivity of a predetermined, fixed volume within said coil means both in the presence of said sample and in the absence of said sample within said predetermined fixed volume.

31. Apparatus according to claim 30 wherein said monitoring circuit means further includes calculating means responsive to said modulated output signal for calculating said amount of said at least one constituent present in said sample and for producing a corresponding constituent content output signal.

32. Apparatus according to claim 31 wherein said signal generator means comprises oscillator means for generating a sinusoidal signal at a predetermined frequency and chopper means for chopping said sinusoidal signal at a second predetermined frequency and wherein said balanced modulator means includes synchronous detector means modulated by the signal at said second predetermined frequency from said chopper means and thereby comprising a synchronous modulated and demodulated circuit.

33. Apparatus according to claim 32 wherein said balanced modulator means is coupled in circuit as a multiplier means to produce a modulated output signal proportionate with the real impedance of said predetermined fixed volume within said coil means multiplied by a function of the phase angle difference between the signal from said signal generator means received both by way of said coil means and by way of a further, fixed phase angle producing circuit.

34. Apparatus according to claim 33 wherein said monitoring circuit means further includes differential AC amplifier means coupled intermediate said balanced modulator means and said synchronous detector means and wherein said differential AC amplifier means is AC coupled with said balanced modulator means.

35. Apparatus according to claim 34 wherein said monitoring circuit means further includes low pass filter means coupled to receive the output of said synchronous detector means.

36. Apparatus according to claim 35 wherein said monitoring circuit means further comprises microcomputer means which comprises said calculating means and further comprises means for controlling a predetermined sequence of operation of said modulator circuit means for determining the real impedance of said coil means when said sample is present in said predetermined volume and again when said sample is absent from said predetermined volume.

37. Apparatus according to claim 36 wherein said monitoring circuit means further includes a fixed impedance reference element and wherein said microcomputer means is further operative to control switching of said fixed impedance reference element for adding the impedance thereof to the impedance of said coil means at predetermined times in said predetermined sequence of operation.

38. Apparatus according to claim 37 wherein said calculating means includes means for calculating the amount of said at least one constituent present in said sample based upon the modulated signals produced by said balanced modulator circuit means both in the presence and absence of said sample within said predetermined fixed volume and with said predetermined known reference impedance element both in circuit and out of circuit with said coil means.

39. A test apparatus for measuring the amount of at least one constituent present in a sample of material, wherein said at least one constituent bears a known relationship to the electrical conductivity of the sample, comprising: a sensor including receptacle means for receiving a sample of material therein and defining an axis, and field producing means, said field producing means including means for producing an electromagnetic field within said receptacle, means for substantially confining said electromagnetic field to a predetermined, fixed volume within said receptacle means and substantially coaxially therewith, means for producing a substantially constant magnitude electromagnetic field throughout said predetermined, fixed volume, and wherein said field producing means further includes means for substantially eliminating axial electric field components in said electromagnetic field.

40. A test apparatus for measuring the amount of at least one constituent in a sample of material, which constituent bears a known relationship to the electrical conductivity of the sample, comprising: a sensor including receptacle means for receiving a sample of material therein and field producing means for producing an electromagnetic field within said receptacle, and monitoring circuit means coupled with said sensor and responsive thereto for producing an output signal which bears a predetermined relationship with the real impedance of said sensor and therefore with the conductivity of said sample when said sample is received in said receptacle, and wherein said field producing means further includes means for substantially eliminating axial electric field components in said electromagnetic field.

* * * * *